US012716061B2

(12) United States Patent
Garcia Dominguez et al.

(10) Patent No.: US 12,716,061 B2
(45) Date of Patent: Aug. 25, 2026

(54) HYDRODYNAMICALLY CONTROLLED ELECTRIC FIELDS FOR HIGH THROUGHPUT TRANSFORMATION AND HIGH THROUGHPUT PARALLEL TRANSFORMATION PLATFORM

(71) Applicant: Massachusetts Institute of Technology, Cambridge, MA (US)

(72) Inventors: Paulo Andres Garcia Dominguez, Cambridge, MA (US); Zhifei Ge, Cambridge, MA (US); Rameech N. McCormack, Cambridge, MA (US); Cullen Richard Buie, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1352 days.

(21) Appl. No.: 16/306,115

(22) PCT Filed: May 31, 2017

(86) PCT No.: PCT/US2017/035270
§ 371 (c)(1),
(2) Date: Nov. 30, 2018

(87) PCT Pub. No.: WO2017/210334
PCT Pub. Date: Dec. 7, 2017

(65) Prior Publication Data

US 2019/0136224 A1 May 9, 2019

Related U.S. Application Data

(60) Provisional application No. 62/504,354, filed on May 10, 2017, provisional application No. 62/441,822,
(Continued)

(51) Int. Cl.
*C12N 13/00* (2006.01)
*B01L 3/02* (2006.01)
*C12M 1/42* (2006.01)

(52) U.S. Cl.
CPC ............ *C12N 13/00* (2013.01); *B01L 3/0275* (2013.01); *C12M 35/02* (2013.01); *B01L 2300/0832* (2013.01); *B01L 2400/0415* (2013.01)

(58) Field of Classification Search
CPC ...... C12N 13/00; C12M 35/02; B01L 3/0275; B01L 2300/0832; B01L 2400/0415
See application file for complete search history.

(56) References Cited

U.S. PATENT DOCUMENTS 6,110,332 A 8/2000 Swierkowski
7,678,564 B2 3/2010 Muller-Hartmann et al.
(Continued)

FOREIGN PATENT DOCUMENTS

EP 1329502 A2 7/2003
GB 2523579 A 9/2015
(Continued)

OTHER PUBLICATIONS

Hollon, Tom, and Fayth K. Yoshimura. “A nonuniform electrical field electroporation chamber design.” Analytical biochemistry 182.2 (1989): 253-256. (Year: 1989).*
(Continued)

*Primary Examiner* — Robert J Eom
(74) *Attorney, Agent, or Firm* — Hamilton, Brook, Smith & Reynolds, P.C.

(57) ABSTRACT

Methods and apparatuses for cell electroporation are provided. An apparatus includes a fluid transport structure, such as a pipette, that includes an electroporation structure defining a flow path having a constriction. The fluid transport
(Continued)

structure also includes at least two conductive elements configured to produce an electric field in the flow path. The conductive elements are in operative arrangement with each other and are configured to expose cells contained within a cell suspension flowing through the fluid transport structure to an electric field that is sufficient to electroporate at least a subset of the cells in the flow path.

10 Claims, 34 Drawing Sheets
(27 of 34 Drawing Sheet(s) Filed in Color)

Related U.S. Application Data filed on Jan. 3, 2017, provisional application No. 62/343,407, filed on May 31, 2016.

(56) References Cited

U.S. PATENT DOCUMENTS

| | | | | |
|---|---|---|---|---|
| 9,039,883 | B2 | 5/2015 | Guerrieri et al. | |
| 10,376,889 | B1 | 8/2019 | Masquelier et al. | |
| 10,415,058 | B2 | 9/2019 | Bernate et al. | |
| 10,450,543 | B2 | 10/2019 | Chang et al. | |
| 10,947,526 | B2 | 3/2021 | Buie et al. | |
| 2002/0079219 | A1 | 6/2002 | Zhao et al. | |
| 2004/0106189 | A1 | 6/2004 | Dodgson et al. | |
| 2005/0048651 | A1 | 3/2005 | Ryttsen et al. | |
| 2005/0282265 | A1 | 12/2005 | Vozza-Brown et al. | |
| 2006/0115888 | A1 | 6/2006 | Gamelin et al. | |
| 2007/0105206 | A1 | 5/2007 | Lu et al. | |
| 2010/0032297 | A1 | 2/2010 | Sugiyama et al. | |
| 2011/0079521 | A1* | 4/2011 | Revol-Cavalier ...... | G01N 27/07 204/403.01 |
| 2012/0048732 | A1* | 3/2012 | Hayashi ................ | G01N 33/86 204/403.02 |
| 2017/0211128 | A1 | 7/2017 | Talebpour et al. | |
| 2017/0218355 | A1 | 8/2017 | Buie et al. | |
| 2018/0179485 | A1 | 6/2018 | Borenstein et al. | |
| 2018/0362908 | A1 | 12/2018 | Borenstein et al. | |
| 2020/0332276 | A1 | 10/2020 | Buie et al. | |

FOREIGN PATENT DOCUMENTS

| | | | | |
|---|---|---|---|---|
| WO | 2006001614 | A1 | 1/2006 | |
| WO | 2006004558 | A1 | 1/2006 | |
| WO | WO-2006112870 | A1 * | 10/2006 | ............ C12M 35/02 |
| WO | WO 2009/129327 | A1 | 10/2009 | |
| WO | 2013059343 | A1 | 4/2013 | |
| WO | 2016003485 | A1 | 1/2016 | |
| WO | 2017210334 | A1 | 12/2017 | |

OTHER PUBLICATIONS

Rebersek, M., et al. "Cell membrane electroporation—Part 3: the equipment." IEEE Electrical Insulation Magazine 30.3 (2014): 8-18. (Year: 2014).*

Shin, Young Shik, et al. "Electrotransfection of mammalian cells using microchannel-type electroporation chip." Analytical chemistry 76.23 (2004): 7045-7052. (Year: 2004).*

International Preliminary Report on Patentability for Int'l Application No. PCT/US2017/035270, titled: Hydrodynamically Controlled Electric Fields For High Throughput Transformation & High Throughput Parallel Transformation Platform, Date of Issuance: Dec. 4, 2018.

Andresen et al., "Injection molded chips with integrated conducting polymer electrodes for electroporation of cells," J. Micromech. Microeng., 20: 1-9 (2010).

Kim et al., "Cell electroporation chip using multiple electric fields zones in a single channel," Applied Physics Letters, 101: 223705-1 through 223705-5 (2012).

Notification of Transmittal of the International Search Report and Written Opinion of the International Searching Authority, or the Declaration, for International Application No. PCT/US2017/035270, entitled "Hydrodynamically Controlled Electric Fields for High Throughput Transformation & High Throughput Parallel Transformation Platform", Dated: Aug. 28, 2017 (15 pgs).

Notification of Transmittal of the International Search Report and the Written Opinion of the International Searching Authority, or the Declaration, for International Application No. PCT/US2014/069615, entitled "Microfluidic Assay for Rapid Optimization of Cell Electroporation", Dated: Dec. 16, 2015 (12 pgs).

International Preliminary Report on Patentability, issued in International Application No. PCT/US2014/069615, entitled "Microfluidic Assay for Rapid Optimization of Cell Electroporation", Dated: Jan. 12, 2017 (8 pgs).

Gallo-Villanueva, R.C., et al., "Joule Heating Effects on Particle Immobilization in Insulator-Based Dielectrophoretic Devices," Eelectrophoresis, 35(0):352-361 (2014).

Wang, H-Y., et al., "A Microfluidic Flow-Through Device for High Throughput Electrical Lysis of Bacterial Cells Based on Continuous DC voltage," Biosensors and Bioelectronics, 22:582-588 (2006).

Geng, T. et al., "Microfluidic Electroporation for Cellular Analysis and Delivery," Lab Chip, 13:3803-3821 (2013).

Geng, T. et al., "Transfection of Cells Using Flow-Through Electroporation based on Constant Voltage," Nature Protocols, 6(8):1192-1208 (2011).

Garcia, P.A., et al., "Intracranial Nonthermal Irreversible Electroporation: In Vivo Analysis," J. Membrane Biol., 236:127-136 (2010).

Geng, T. et al., "Flow-through electroporation based on constant voltage for large-volume transfection of cells," Journal of Controlled Release, 144: 91-100 (2010).

Zhan, Y. et al., "Low-frequency ac electroporation shows strong frequency dependence and yields comparable transfection results to dc electroporation," Journal of Controlled Release, 160:570-576 (2012).

BTX Harvard Apparatus: Molecular Delivery Systems, "HT 96 and 25 Well Electroporation Plates," www.btxonline.com date unavailable, 2 pages.

Ziv, R., et al., "Micro-electroporation of mesenchymal stem cells with alternating electrical current pulses," Biomed Microdevices 11:95-101 (2009).

* cited by examiner

Electric Potential [V]; V = 2500 V

×10³

2.5
2
1.5
1
0.5
0

Distance [mm]

2.5
2
1.5
1
0.5
0
-0.5
-1
-1.5
-2
-2.5

0

Distance [mm]

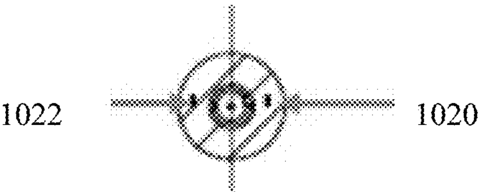
FIG. 10C
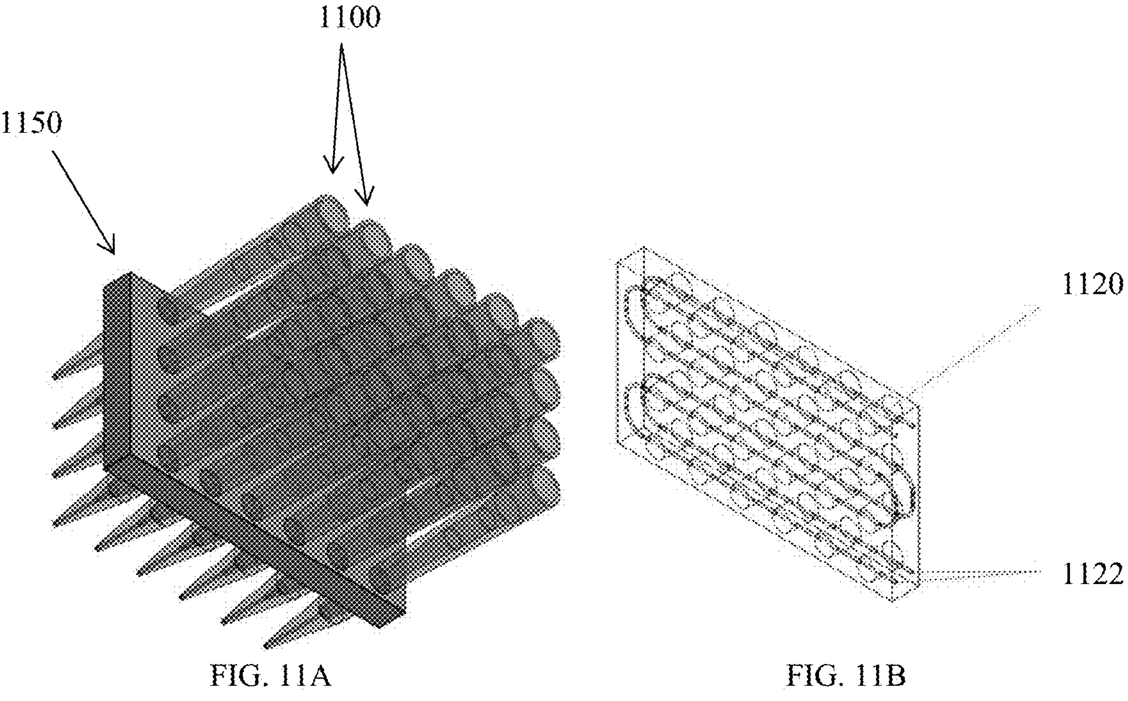
FIG. 11A
FIG. 11B

HYDRODYNAMICALLY CONTROLLED ELECTRIC FIELDS FOR HIGH THROUGHPUT TRANSFORMATION AND HIGH THROUGHPUT PARALLEL TRANSFORMATION PLATFORM

RELATED APPLICATIONS

This application is the U.S. National Stage of International Application No. PCT/US2017/035270, filed May 31, 2017, which designates the U.S., published in English, and claims the benefit of U.S. Provisional Application No. 62/504,354, filed on May 10, 2017, U.S. Provisional Application No. 62/441,822, filed on Jan. 3, 2017, and U.S. Provisional Application No. 62/343,407, filed on May 31, 2016. The entire teachings of the above applications are incorporated herein by reference.

GOVERNMENT SUPPORT

This invention was made with government support under Grant Nos. HR0011-15-9-0014 and D13AP00025 from the Defense Advanced Research Projects Agency (DARPA), Grant No. 1150615 from the National Science Foundation (NSF) Division of Chemical, Bioengineering, Environmental, and Transport (CBET) Systems, and Grant Nos. 1562925 and 1640678 from the NSF Division of Industrial Innovation and Partnerships (IIP). The government has certain rights in the invention.

BACKGROUND

Genetic engineering and synthetic biology hold great potential to develop microbiome therapeutics, artificial photosynthesis, biomolecular manufacturing, in vivo diagnostics, and targeted cancer treatments. A key step in genetic engineering is delivering genetic materials into cells. However, there is no single technology that solves all problems in intracellular delivery of genetic materials. Delivery of genetic material through viral vectors, for example, is very efficient in both bacterial and mammalian cells, but this procedure is cell-type specific, and has problems with immunogenicity and random insertion when moving into clinical applications. Cell squeezing is a new invention in intracellular delivery of large molecules, but is currently limited to mammalian cells. Conjugation is widely used among transformations of *E. coli*, Mycobacteria, and *Bacillus*, but has problems with cell-type specificity and is not scalable to other bacterial species.

Since its invention in the 1980s, electroporation (EP) has been widely used for introducing genetic materials into both mammalian and bacterial cells. Additionally, delivery of very large size plasmids, such as bacterial artificial chromosomes (BAC, typically 150-350 kbp) can be achieved. Electroporation is not species specific, but without optimization, electroporation can lead to high cell mortality, high experimental cost, low transformation efficiency, and low throughput. The low efficiency can result from cell properties (such as thick cell walls), plasmid size, and the physical and chemical conditions of the transformation process. Electroporation uses pulsed electric fields to reversibly disrupt the cell envelope for intracellular delivery of exogenous materials, such as DNA. This method is strongly dependent on the electric field strength experienced by the cells: fields that are too high cause irreversible electroporation and cell lysis causing death. While lysis has many important applications such as non-thermally treating inoperable tumors, it hinders genetic engineering. Conversely, electric fields that are too low are insufficient to introduce exogenous materials and cells cannot be engineered. As a result, the field strength has to be closely monitored and tailored to each cell type for electroporation to achieve optimal levels of viability and transformation efficiency.

SUMMARY

Systems and methods of the present invention provide for flow-through electroporation demonstrating improved transfection efficiency and higher cell viability as compared with conventional methods. Systems and methods of the present invention can be used to provide high-throughput transformation of cells, including bacterial cells, for genetic engineering applications.

In one embodiment, the present invention is an apparatus for cell electroporation that includes a fluid transport structure, such as, for example, a pipette tip, a tube fitting, or a microfluidic device. The fluid transport structure includes an electroporation structure defining a flow path having a constriction. The fluid transport structure further includes at least two conductive elements configured to produce an electric field in the flow path. The conductive elements are in operative arrangement with each other and are configured to expose cells contained within a cell suspension flowing through the fluid transport structure to an electric field that is sufficient to electroporate at least a subset of the cells in the flow path.

The electroporation structure can further define a cavity upstream of the flow path configured to reduce a volume of the cell suspension flowing through the fluid transport structure prior to the cell suspension's reaching the flow path. The electroporation structure can also optionally further define a reservoir downstream of the flow path configured to store a cell solution exiting the flow path.

The fluid transport structure can define a reservoir upstream of the flow path configured to store a cell solution prior to the cell suspension's reaching the flow path. The fluid transport structure can also optionally further define a cavity downstream of the flow path configured to aspirate the cell suspension.

The constriction within the electroporation structure can include non-uniform cross-sectional areas, such that the constriction has a bilaterally converging geometry, a converging geometry, or a diverging geometry. The constriction can also have a curved geometry. Alternatively, the constriction can be a straight constriction, such as between two tapering reservoirs on either side of the flow path. The device may also include multiple constrictions arranged in series, in parallel, or a combination of both. Furthermore, a fluid transport device can include multiple electroporation structures, for example, arranged in series, in parallel, or both.

Conductive elements, such as electrodes, electrically conductive thin film, metal foam, mesh electrodes, a liquid diffusible membrane, or any combination thereof can be included in the apparatus and, optionally, embedded within the fluid transport structure and/or the electroporation structure. For example, electrodes can be arranged axially within the fluid transport structure or transversely within the fluid transport structure.

The apparatus can further include a pump configured to deliver cell solution to the fluid transport structure at a volumetric flow rate of, for example, about 0.25 mL/min to about 5 mL/min, or about 0.5 mL/min to about 2 mL/min.

A residence time of cell solution flowing through the flow path can be about 0.5 ms to about 100 ms, or of about 5 ms to about 50 ms.

A voltage source can also be included in the apparatus and configured to deliver an applied voltage of about 0.5 kV to about 3.0 kV, for example, about 2.5 kV. A controller can be configured to deliver pulses of applied voltage having durations of, for example, about 0.001 ms to about 50 ms, about 0.5 ms to about 10 ms, or of about 1 ms to about 5 ms. The pulses can be applied at a duty cycle of about 25% to about 99.9%, or of about 50% to about 99%, for example, at 95%.

The electroporation structure can optionally define more than one flow path, such as at least two flow paths or at least eight flow paths. The flow paths can be isolated from one another, or optionally, branching and parallel to one another to provide a gradient generator.

In another embodiment, the present invention is a method of performing cell electroporation that comprises enabling flow-through delivery of a cell suspension to a flow path defined within a fluid transport structure. The method further includes applying a voltage to generate an electric field in the flow path and amplifying the electric field within the flow path to produce an amplified electric field, which is sufficient to electroporate at least a subset of cells within the cell suspension as the cells travel through the flow path. Amplifying the electric field, as used herein, refers to constricting the flow path such that the voltage within or across the flow path increases as a function of the constriction.

Flow of a cell suspension through the flow path can be continuous. Amplifying the electric field can be performed, at least in part, by constricting a flow of the suspension.

For mammalian cells, the method can further include applying a voltage of about 0.1 kV to about 0.5 kV the flow path that results in a maximum electric field of about 0.5 kV/cm to about 2.5 kV/cm as a function of the amplification.

For bacterial cells, the method can further include applying a voltage of about 1.5 kV to about 2.5 kV to the flow path that results in a maximum electric field of about 7.5 kV/cm to about 12.5 kV/cm as a function of the amplification.

Pulses of an applied voltage can be delivered, with each pulse having a duration of about 0.001 ms to about 50 ms, about 1 ms to about 10 ms, for example, about 5 ms. The pulses can be applied at a duty cycle of about 25% to about 99.9%, or of about 50% to about 95%.

Delivery of the cell suspension can be performed at a flow rate of about 0.25 mL/min to about 5 mL/min, or of about 0.5 mL/min to about 2 mL/min. A residence time of cell solution flowing through the flow path can be of about 50 ms or less, for example about 0.5 mL/min to about 2 mL/min. The cell suspension can include a conductivity buffer having a buffer concentration of about 1×10ˆ−9 M to about 1×10ˆ−4 M.

The method can further include enabling delivery of a payload to the subset of cells. The payload can be a protein or a nucleic acid, such as DNA, RNA, mRNA, siRNA, or a CRISPR-Cas construct. The subset of cells transfected with the payload can be at least about 0.001%, at least about 0.01%, 0.1%, at least about 1%, at least about 10%, at least about 20%, at least about 30%, or at least about 40% of the cells contained in the cell suspension travelling through the flow path. The percentage of the subset of cells transfected by the payload can vary depending upon the size of cells and the size of the payload.

In another embodiment, the present invention provides for an apparatus for cell electroporation that includes means for transporting fluid to an electroporation structure defining a flow path having a constriction, means for producing an electric field in the flow path, and means for exposing cells contained within a cell suspension flowing through the apparatus to an electric field that is sufficient to electroporate at least a subset of the cells in the flow path.

In yet another embodiment, the present invention provides for an electroporation system having a plurality of fluid transport structures arranged in parallel. Each fluid transport structure includes an electroporation structure defining a flow path and at least two conductive elements configured to produce an electric field in the flow path (e.g., across the flow path). The electroporation structure and the at least two conductive elements are in operative arrangement with each other and configured to expose cells contained within a cell suspension flowing through the fluid transport structure to an electric field that is sufficient to electroporate at least a subset of the cells in the flow path.

The system can also include at least one pump configured to induce a flow of cell solution through the plurality of fluid transport structures. The flow of cell solution can be at a rate of about 0.25 mL/min to about 5 mL/min.

The system can further include a controller to determine and/or apply appropriate parameters for electroporation. For example, the controller can determine a voltage and/or a pulse distribution to be applied to the conductive elements, such as based on a cell type. The controller can further apply the selected voltage with the selected pulse distribution. The pulse distribution can include pulses having durations of about 0.001 ms to about 50 ms, or of about 0.1 ms to about 10 ms, operating at a duty cycle of at about 25% to about 99.9%.

The plurality of fluid transport structures of a system can be configured to interface with a multi-well plate, such as a 96-well plate, or the like.

In another embodiment, the present invention provides for a method of performing cell electroporation that includes enabling flow-through delivery of a cell suspension to a plurality of flow paths, each flow path defined within a fluid transport structure, applying a voltage to generate an electric field in the flow paths, and amplifying the electric field within the flow paths to produce an amplified electric field in each of the fluid transport structures. The amplified electric field is sufficient to electroporate at least a subset of cells within the cell suspension as the cells travel through the flow path.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 10C is another cross-section view of the pipette tip of FIG. 10A.

FIG. 11A is sectioned, perspective view of a micropipette holder.

FIG. 11B is a transparent perspective view of the micropipette holder of FIG. 11A.

FIG. 12B is a cross-section view of the tube fitting of FIG. 12A.

FIG. 13B is a section view of the tube fitting of FIG. 13B.

DETAILED DESCRIPTION

Figure 1:
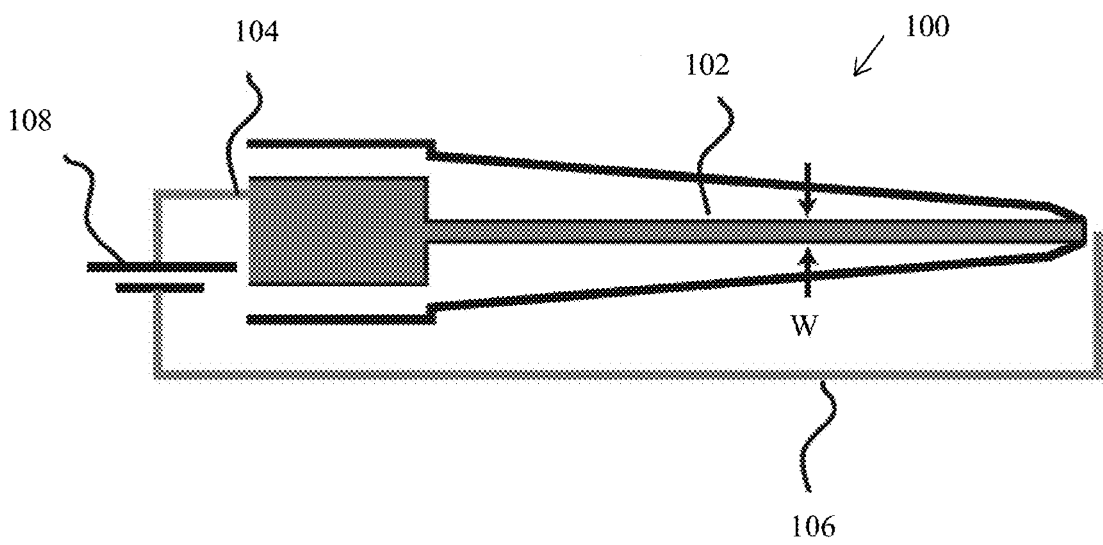
FIG. 1 is a schematic illustrating an embodiment of a pipette tip.

Conventional Electroporation Systems and Challenges for Bacterial Transformation Conventional electroporation systems for the transfection of cells generally involve the use of cuvettes, in which single batches of cells are exposed to electric fields at predetermined thresholds. Cuvette-based electroporation approaches are inefficient for transforming high volumes of cells. Systems for cuvette-based electroporation, referred to as exponential decay systems, also provide low cell viability and low transfection rates. In general, genetic engineering of eukaryotic cells is referred to as transfection while genetic engineering of prokaryotic cells is referred to as transformation. However, in several instances throughout this application transfection and transformation are used interchangeably due to the electroporation structure being agnostic to the cell type being engineered.

Microfluidic electroporation for mammalian cell applications has demonstrated significantly improved transfection efficiency and higher cell viability compared to cuvette-based electroporation. Flow-through transfections in microfluidic devices generally use a fraction of the experimental sample and lower voltages than cuvette-based electroporation, which helps to maintain high cell viability and high transfection efficiency. One type of transfection process involves immobilizing cells with channel constrictions that are smaller than the cell diameter. For example, microhole structures in silicon nitride dielectric membranes are used for initially trapping and subsequently electroporating single cells. Similarly, nanochannels, dielectrophoresis, and magnetic tweezers are used to position cells prior to transfections with electroporation, enabling single-cell dosage control. Other types of transfection processes include the uses of microfluidic chips that selectively immobilize and electroporate single cells, 2D and 3D nanochannels that deliver transfection agents into mammalian cells with electroporation, and microfluidic devices for stem cell attachment, differentiation, and subsequent transfection of neurons on chip for studying cells in their natural state. With the ability to control single-cell dosage, some microfluidic devices are able to handle 40,000-60,000 mammalian cells/cm$^2$.

Another methodology for mammalian cell transfection uses flow-through processes in which groups of cells are exposed to sufficiently high electric fields when they flow through particular regions of a microfluidic channel. Such microfluidic devices include a series of geometric constrictions with uniform cross-sectional areas for flow-through electroporation based on DC or AC signals. Vortex-assisted microfluidic applications are also used to improve transfection efficiency by increasing a fraction of a total membrane surface that is permeabilized. Sequential delivery of different molecules is performed with independent and precise dosage controllability into human cancer cells with inertial focusing. Lastly, a flow-through microfluidic device with a comb electrode layout successfully characterizes HeLa cell transfection.

Despite significant advances in microfluidic transfection of mammalian cells, transformation of bacteria requires several modifications to the techniques currently being used in mammalian cells. To transform bacteria, the devices need to be able to achieve electric fields that are approximately one order of magnitude larger than that required for mammalian cell transfection, primarily because bacteria are much smaller in size (nominally around 1 m). With these differences, significant Joule heating can occur within the device during pulse application as a result of the high electric fields required for bacterial transformation. The resulting temperature in the channel can be high enough to compromise cell viability. Also, geometric constrictions to immobilize bacteria, as has been used with mammalian cells, are generally impractical. To immobilize bacteria, the constrictions need to be in the tens-to-hundreds of nanometers in diameter, resulting in significantly higher fluidic resistance as compared with microchannels used for mammalian cells. Furthermore, such dimensions are so small that they would be challenging to fabricate at large scale with current technologies.

Recently, electroporation systems and methods for exposing cells, particularly bacteria, to a continuum of electric fields to determine optimal electromagnetic conditions for successful gene transformation have been developed and are further described in International Publication No. WO2016/003485, the entire content of which is incorporated herein by reference.

Flow-Through Electroporation Systems and Methods

A description of example embodiments follows.

Systems and methods of the present invention provide for the transformation of bacterial cells by electroporation at higher transformation efficiencies, higher throughputs, and higher cell viabilities as compared with traditional cuvette based electroporation approaches. In particular, systems and methods are provided that can perform bacterial transformation with electroporation in a flow-through and/or continuous manner.

As demonstrated in the examples of the present invention, flow-through electroporation with the use of constricted flow paths can produce significantly higher transfections rates while handling higher volumes of cells, as compared with cuvette-based systems. For example, about 600 samples per hour can be processed with example embodiments of the present invention, as compared with about 20 samples per hour for cuvette-based methods. For various types of cells, such as prokaryotic and eukaryotic cells, embodiments of the present invention can produce significantly higher transfection rates than conventional methods. For example, embodiments of the present invention can produce transfection rates of about 20-50% for eukaryotic cells, as compared with about 5-10% transfection rates for eukaryotic cells in cuvette-based methods (Example 14).

An example of an apparatus for cell electroporation is illustrated in FIG. 1. A pipette tip 100 includes a transformation region 102. A first electrode 104 is in operative arrangement with a second electrode 106 and a voltage source 108 to produce an electric field in the transformation region 102 (e.g., across the transformation region). The transformation region 102 includes a macrofluidic or microfluidic flow path (e.g., a channel, a tubular duct, or other passage structure) having a width w. The transformation region 102 of FIG. 1 is for illustrative purposes and is not drawn to scale. As will be explained further below, the width w of the flow path within the transformation region can vary across a length of the region. For example, a flow path in the transformation region can be a channel having non-uniform cross-sectional areas, such that bacteria contained in a cell solution travelling through the channel experience time-dependent electric fields.

Figure 2:
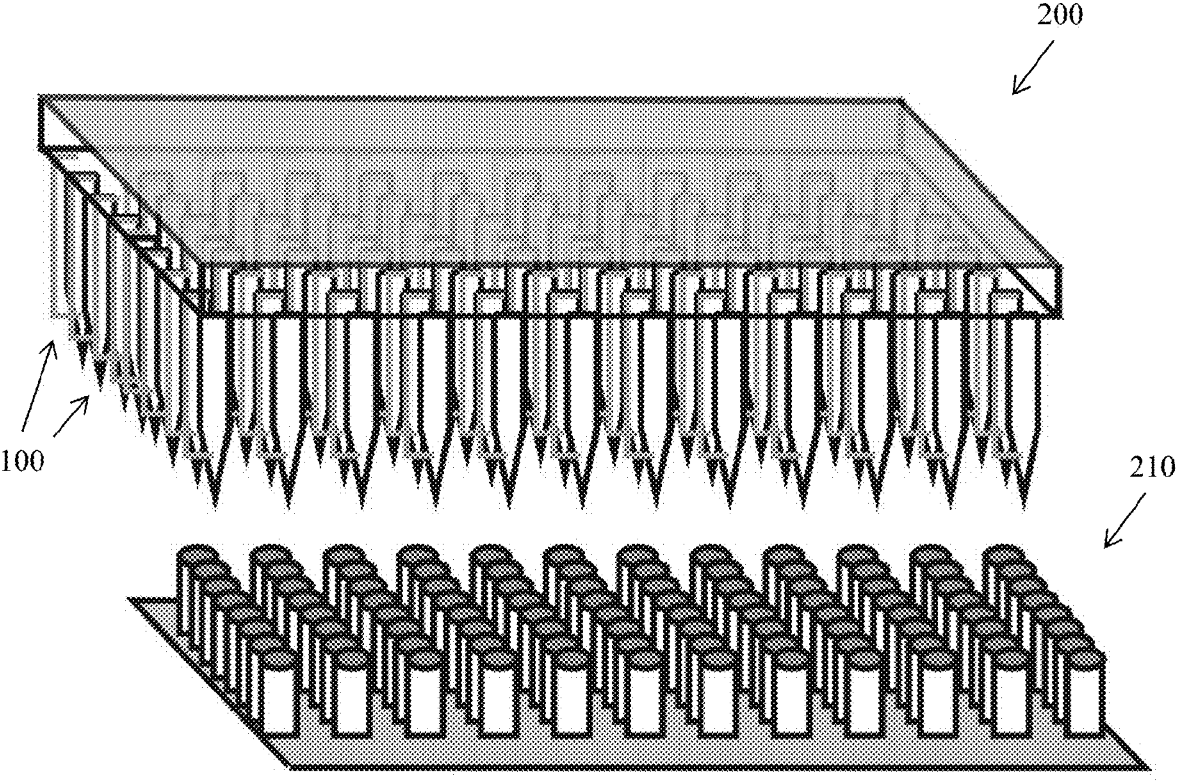
FIG. 2 is a schematic illustrating an embodiment of a liquid handling unit.

Pipette tips 100 can be configured to interface with existing liquid handling or fluid transport apparatuses, such as conventional pipettes or large-scale liquid handling systems. For example, as shown in FIG. 2, a plurality of pipette tips 100 can be arranged in a liquid handling apparatus 200, such as a robotic liquid handling system. The liquid handling apparatus 200 can be, for example, a 96-well liquid handling unit configured to interface with a 96-well plate 210. Alternative arrangements are possible. For example, a number of pipette tips included in a liquid handling system can be reduced to interface with 6-well plates, 8-well plates, 12-well plates, or 48-well plates, or expanded to interface with 384-well plates, 1536-well plates, or other sized plates.

Figure 3:
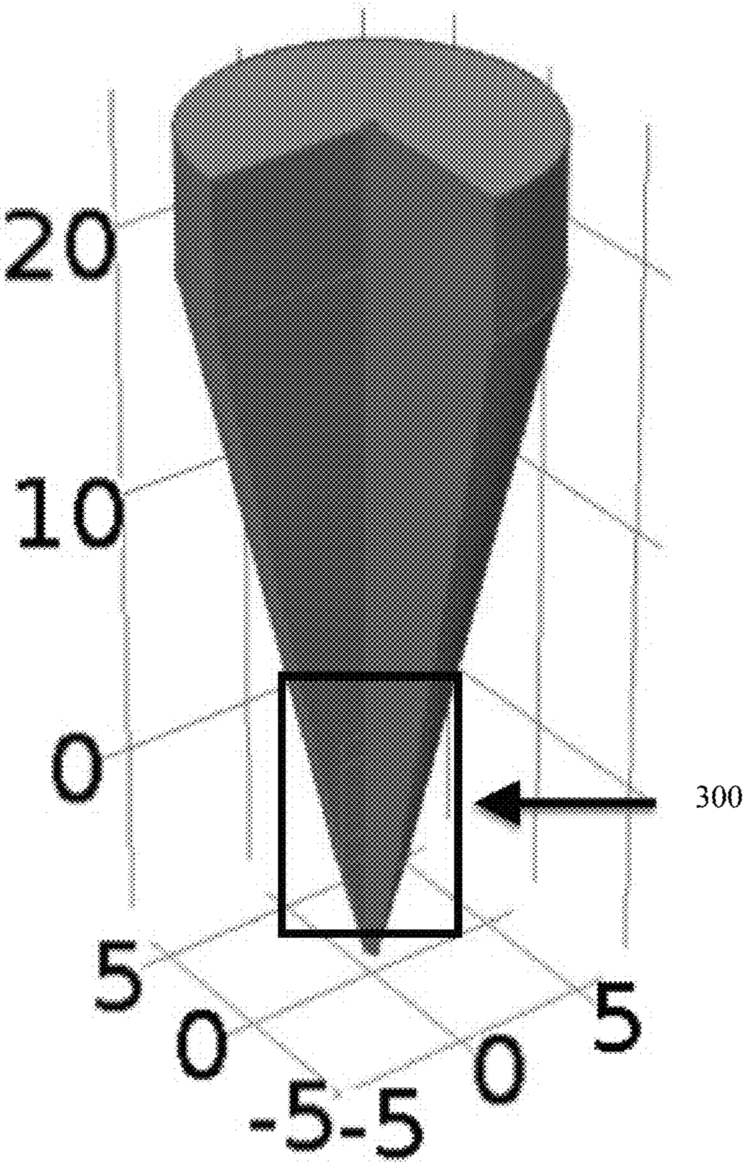
FIG. 3 is a cut-away view of an embodiment of a pipette tip with dimensions in millimeters scale.
Figure 23A:
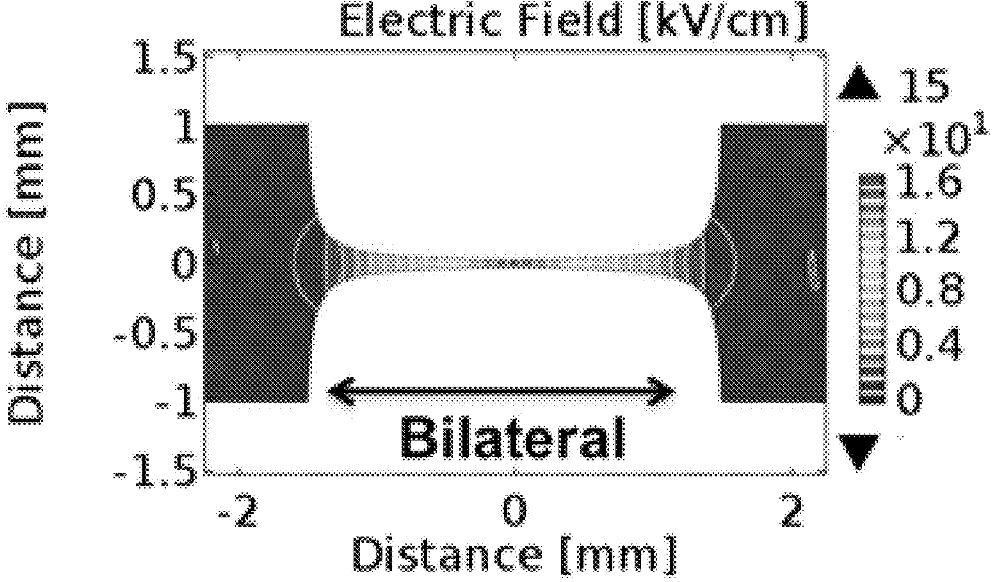
FIG. 23A is a graph illustrating electric field distribution in a microchannel with a bilaterally converging constriction geometry.
Figure 23B:
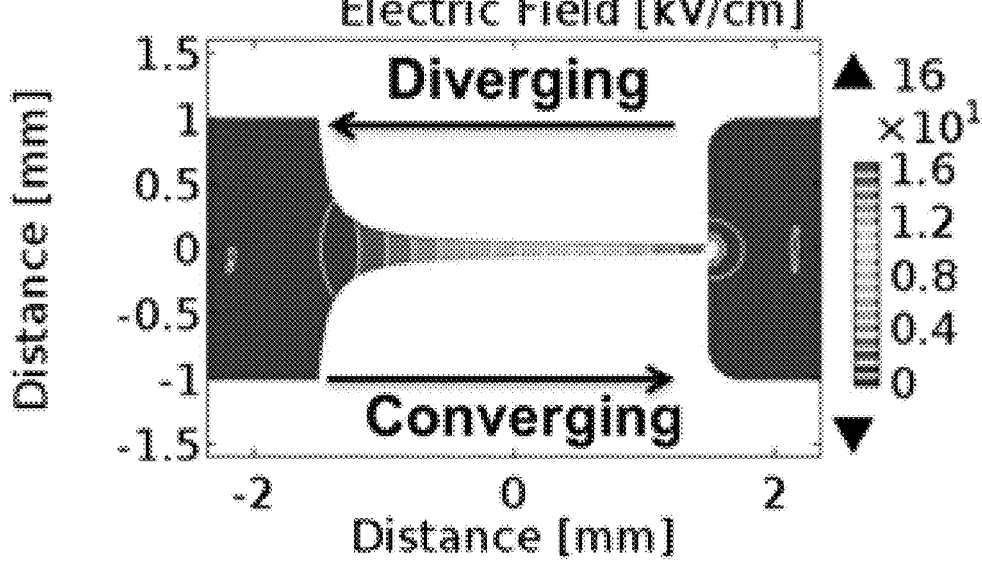
FIG. 23B is a graph illustrating electric field distribution in a microchannel with a diverging/converging constriction geometry.
Figure 23C:
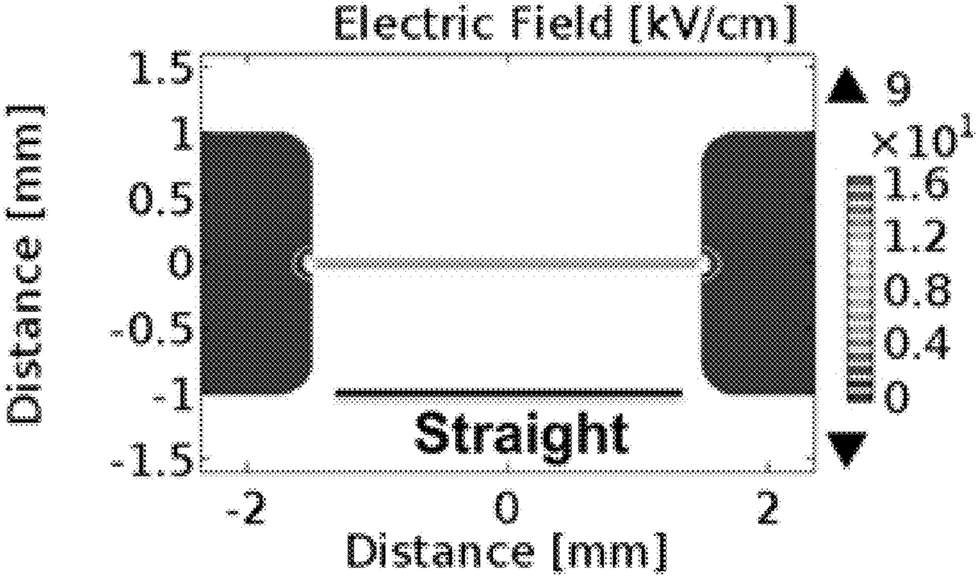
FIG. 23C is a graph illustrating electric field distribution in a microchannel with a straight constriction geometry.

As shown in FIG. 3, a transformation region of a pipette tip includes an electroporation structure 300. The electroporation structure 300 includes a flow path having a constriction, such as the flow path illustrated in FIGS. 4-7, which includes a bilaterally converging constriction. Other configurations of flow paths for electroporation structures are possible, such as a diverging constriction, a converging constriction, or a straight constriction (FIGS. 23A-23C).

Figures 4, 5:
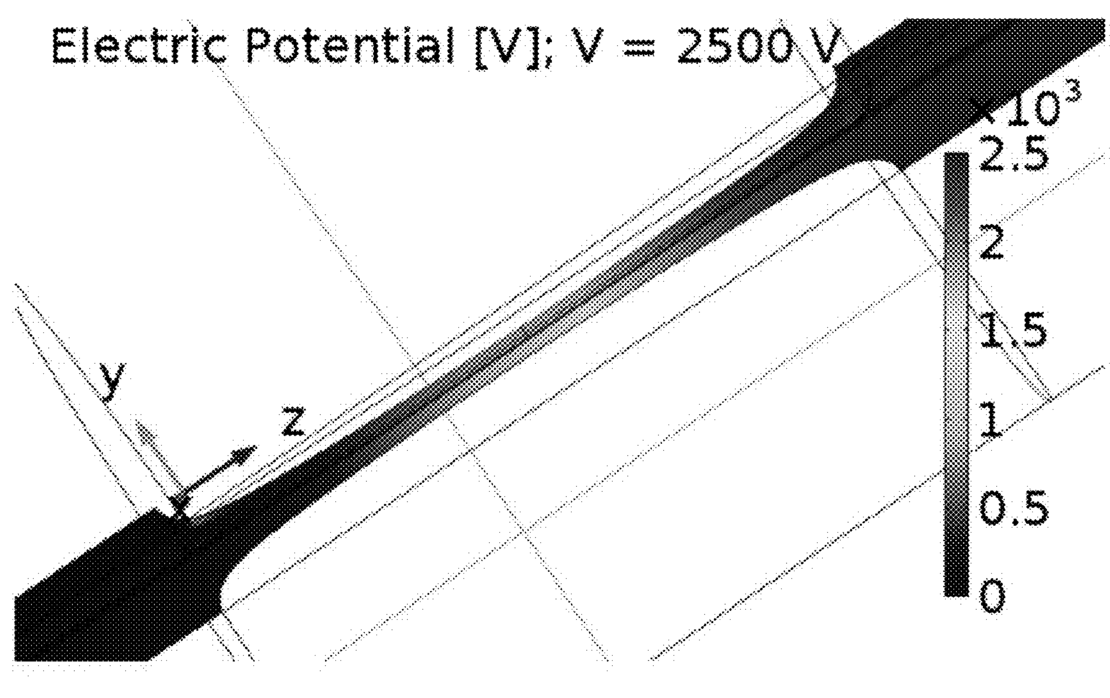
FIG. 4 is a graph illustrating electric potential distribution within a flow path.
FIG. 5 is a graph illustrating electric potential distribution within a cross section of the flow path of FIG. 4.
Figure 6:
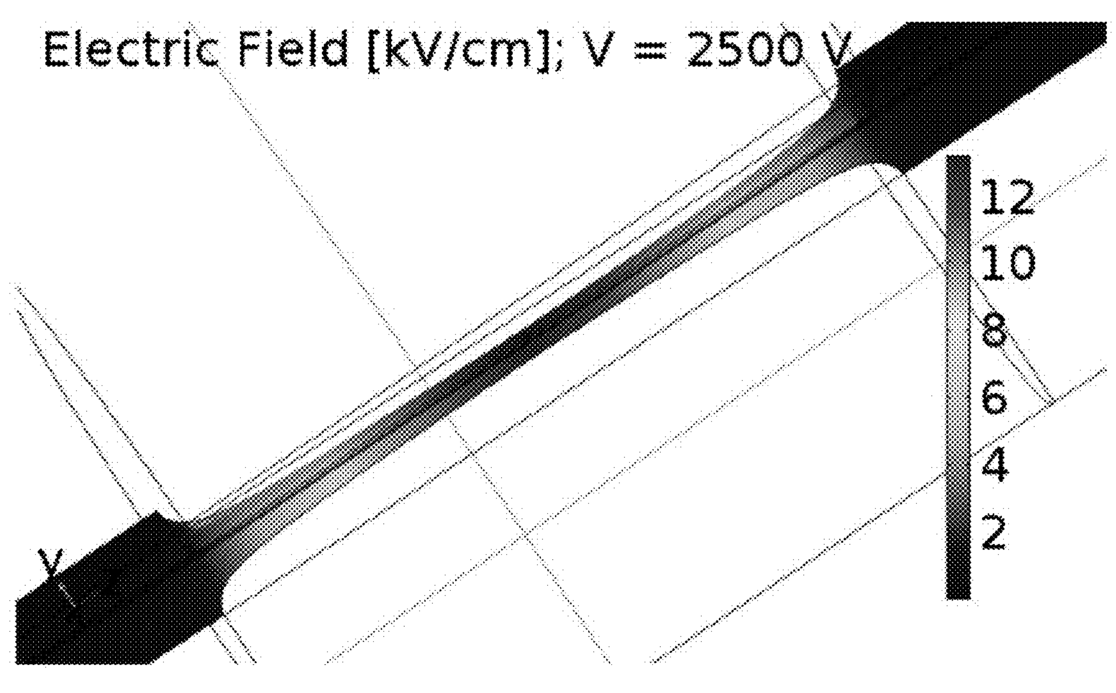
FIG. 6 is a graph illustrating electric field distribution within a flow path.
Figure 7:
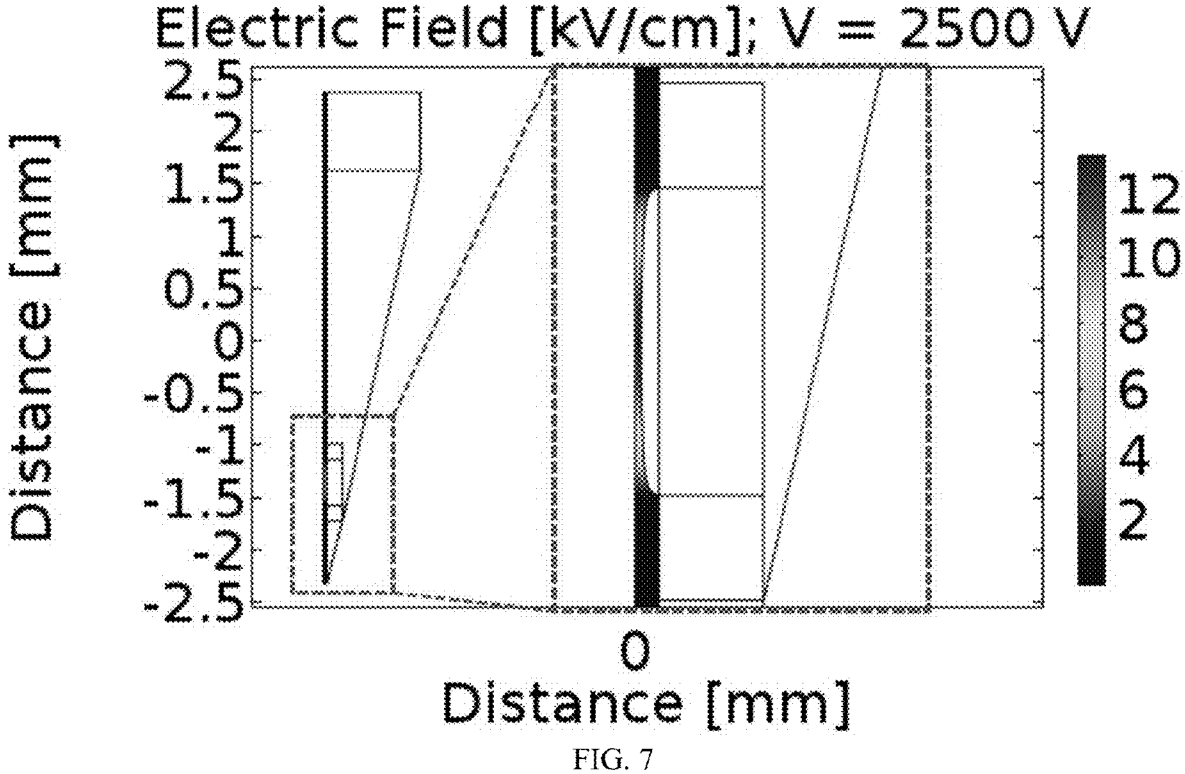
FIG. 7 is a graph illustrating electric field distribution within a cross section of the flow path of FIG. 6.

The electric potential distribution for an example of a flow path having a bilaterally converging constriction is shown in FIGS. 4 and 5. As a cell contained in a cell solution flowing through a pipette tip enters and exits the electroporation structure, it experiences a varying electric field, as illustrated in FIGS. 6 and 7. In particular, local channel geometry (e.g., a bilaterally converging flow path) alters electric field magnitude, providing a hydrodynamic scheme to manipulate an electric pulse as seen by flowing cells. With a bilaterally converging flow path, the highest intensity is seen at the center of the constriction, and the center of the constriction is the location at which electroporation most frequently occurs for cells flowing through the structure.

Figures 8A, 8B:
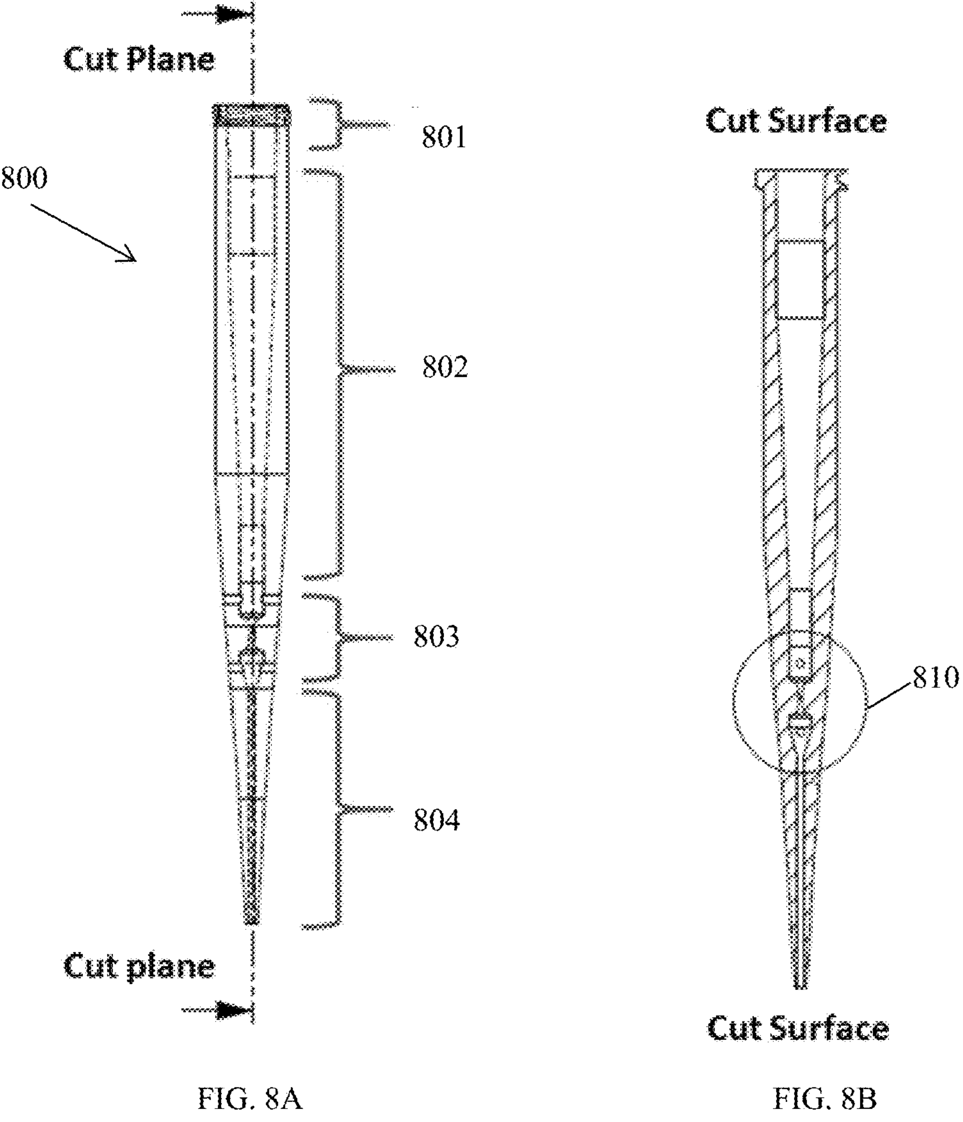
FIG. 8A is a schematic of another embodiment of a pipette tip.
FIG. 8B is a cross-section view of the pipette tip of FIG. 8A.
Figure 8C:
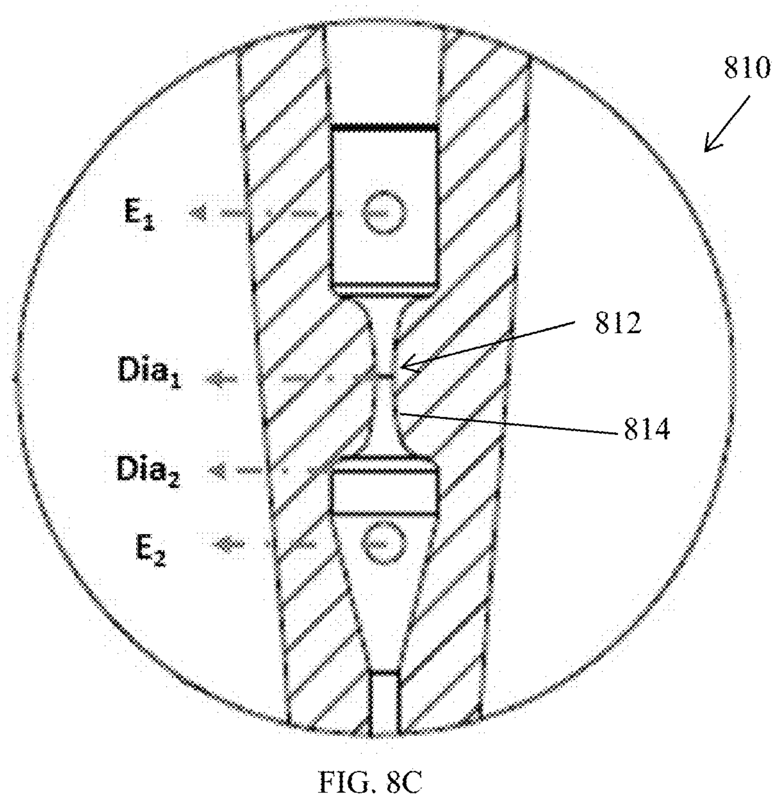
FIG. 8C is a section view of the pipette tip of FIG. 8A.

An example of a fluid transport structure (e.g., a pipette tip) for microorganisms transformation or mammalian cell transfection is shown in more detail in FIGS. 8A-8C. As shown in FIG. 8A, the fluid transport structure 800, shown as a pipette tip, includes a connecting section 801, a reservoir section 802, a constriction region 803, and a dispensing section 804. Connecting section 801 is shown in FIG. 8A as including a luer lock for connection to a fluid-handling manifold. However, the pipette tip 800 can be altered to accommodate a variety of leak free connections (e.g., luer lock, luer slip, quick connects, interference fitting, or other connection types). The pipette tip 800 can be connected to syringes or fluid dispensing devices that enable individuals to precisely monitor flow rate via syringe, pressure, peristaltic and/or vacuum pumps, and/or any other types of fluid displacement devices or mechanisms. Reservoir section 802 can include a flow channel and/or a temporary reservoir for cell storage prior to electroporation.

Constriction region 803 includes a geometric configuration to optimize cell transformation. A more detailed view of constriction region 803, including electroporation structure 810, is shown in FIG. 8C. As used herein, electroporation structure refers to any structure in which an electric field is applied and/or amplified to electroporate at least a subset of cells contained within the structure. The electroporation structure 810 can be characterized by parameters including curvature, minimum diameter $Dia_1$, maximum diameter $Dia_2$, and spacing between at least two conductive elements $E_1$, $E_2$ (e.g., distance between a first electrode $E_1$ and a second electrode $E_2$). While pipette tip 800 is illustrated as having a bilaterally converging constriction 812 in the flow path 814 of region 803, the tip can include alternate geometric shapes. Manipulating the geometric configuration of the constriction of the device can cause various hydrodynamic variations that subject flowing microorganisms to specific pulse waveforms. These variations can be used to tailor the pipette tip's geometric constriction to optimize electroporation conditions for specific microorganisms. The geometric shape of the constriction is not limited to axially symmetric geometries along the pipette tips. The implementation of a microfluidic channel that is similar to a helical or serpentine channel is also within the scope of implementation in the pipette tips' design. Furthermore, channel size can be scaled up or down. For example, macrofluidic channels contained in pipette tips or other fluid transport structures are also within scope of the design. Modifications of the constriction's geometry from an axis may induce additional hydrodynamic phenomena that can increase genetic transformation efficiency during electroporation. Additionally, the microfluidic channel can contain multiple identical or different constrictions arranged in series or in parallel such that cells experience multiple regions of high electric field during transformation.

In the electroporation structure 810 illustrated in FIG. 8C, the electric field is generated via metallic wire electrodes $E_1$, $E_2$, each at one end of the constriction 812, energized from an external electrical power source. Downstream from the electroporation region 803 is a dispensing section 804 that can allow for precise aspiration and dispensation of stored, suspended cells.

Another example of a pipette tip is shown in FIGS. 9A-9H. Modular pipette tip 900 includes an upper portion 901 and a lower portion 902. Upper portion 910 stores a cell suspension prior to electroporation. As illustrated, an electroporation structure 910 is included in the upper portion 901, however electroporation structure 910 could instead be included in lower portion 902. Upper portion 910 can include a series of channels and/or cavities upstream of the electroporation structure 910 to reduce a volume of cell solution travelling through the pipette tip 900 prior to the cell solution reaching the electroporation structure 910. For example, as illustrated, upper portion 910 includes a first cavity 940 in fluid connection with a tapering channel 942, which is, in turn, in fluid connection with a second cavity 944 followed by a second tapering channel 946. Any configuration of cavities, straight channels, and/or tapering channels can be included in pipette tip 900 to enable delivery of a cell solution to electroporation structure 910. By reducing the volume of the cavity prior to constriction, transformation efficiency can be improved by reducing a volume of untransformed cells.

Figures 9A, 9B:
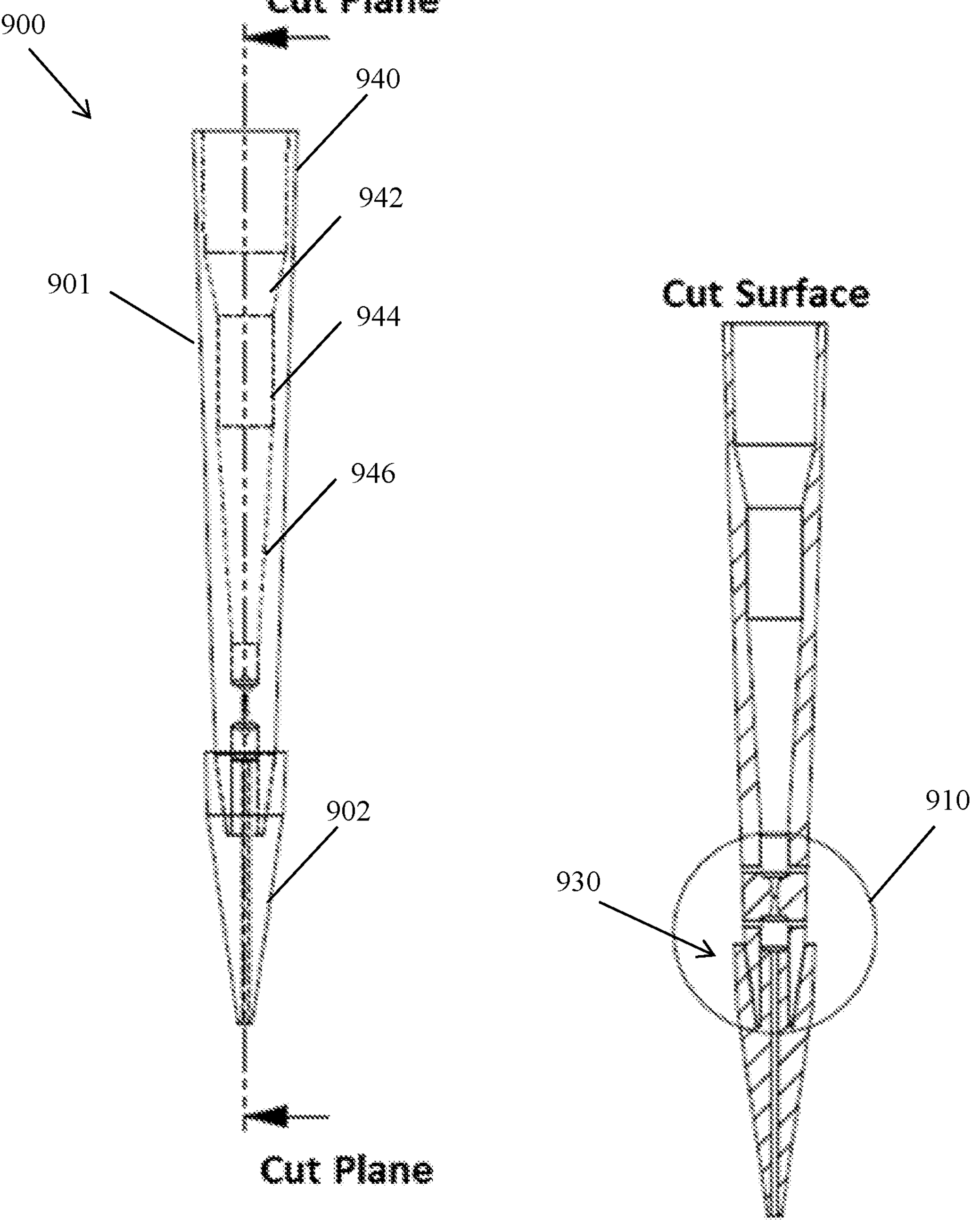
FIG. 9A is a schematic of an embodiment of a modular pipette tip.
FIG. 9B is a cross-section view of the modular pipette tip of FIG. 9A
Figure 9C:
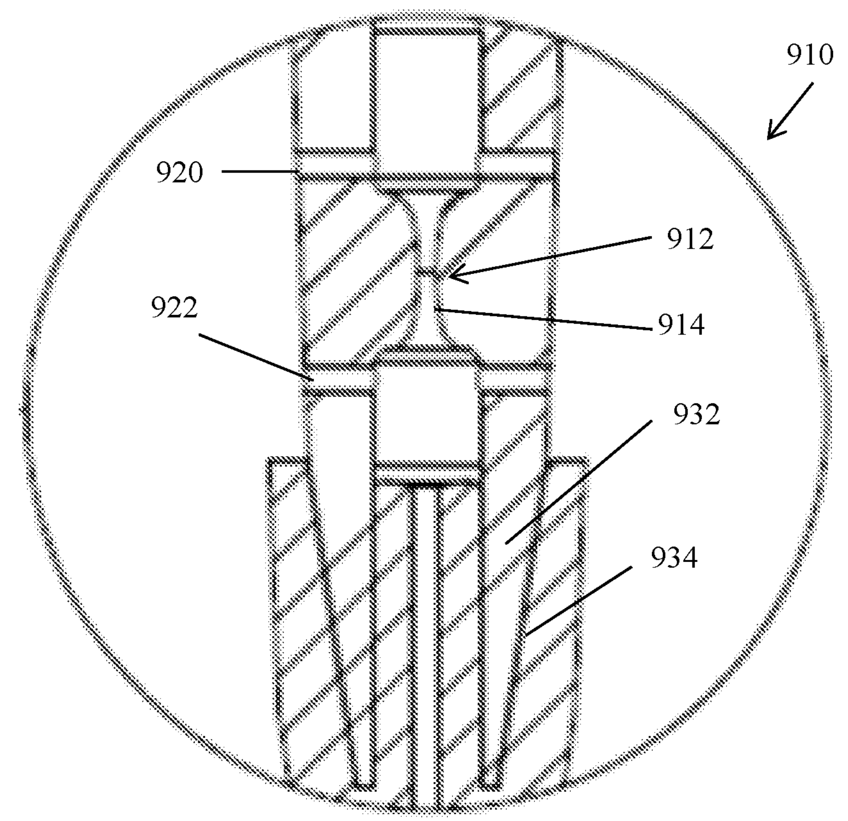
FIG. 9C is a section view of the modular pipette tip of a FIG. 9A.
Figures 9D, 9E:
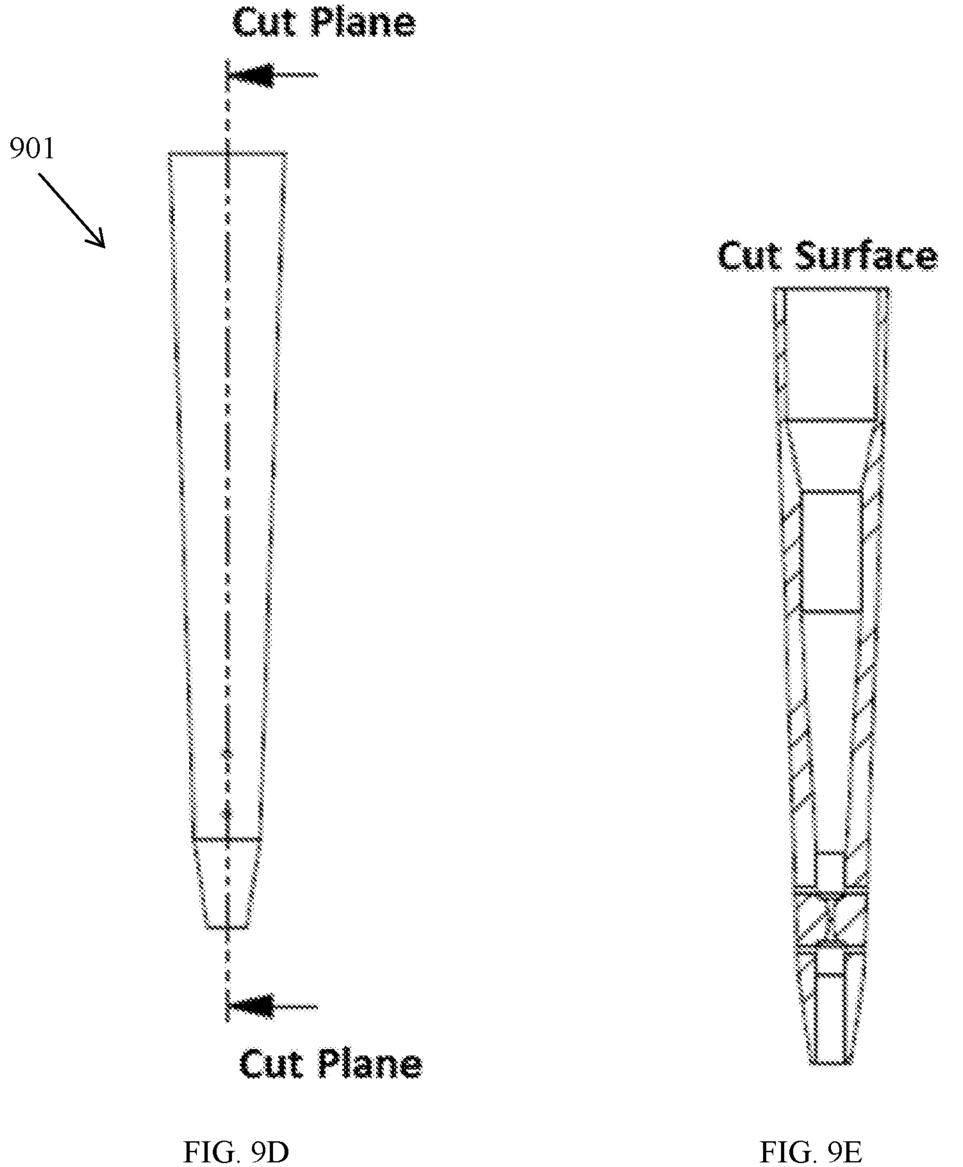
FIG. 9D is a schematic of a modular component of the pipette tip of FIG. 9A.
FIG. 9E is a cross-section view of the modular component of FIG. 9D.
Figure 9F:
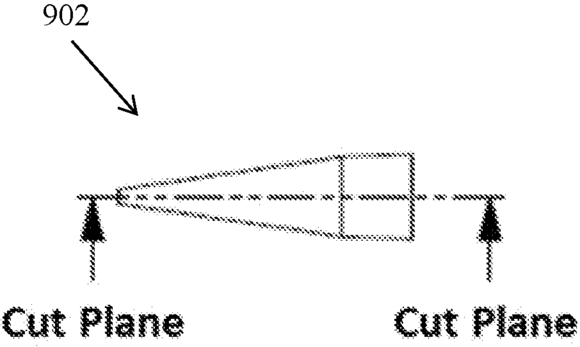
FIG. 9F is a schematic of another modular component of the pipette tip of FIG. 9A.
Figure 9G:
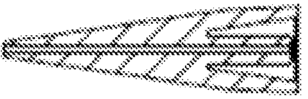
FIG. 9G is a cross-section view of the modular component of FIG. 9F.
Figure 9H:
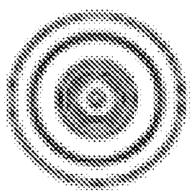
FIG. 9H is a top view of the modular pipette tip of FIG. 9A.

A modular pipette tip, such as pipette tip 900, can be manufactured as individual parts and then assembled with the use of an interference fitting to provide a leak-free interface. A more detailed view of the electroporation structure 910 and interference fitting 930 are shown in FIG. 9C. As illustrated, the conductive regions of the pipette tip 900 can be metallic wires 920, 922 that traverse the pipette tip on either side of the constriction 912 of the flow path 914. For ease of alignment, projections 932 of upper portion 901 can be configured to engage with guide cavities 934 of lower portion 902. The upper and lower portions 901, 902 of the pipette tip can be constructed from any material compatible with the biological cells of interest, such as polypropylene or another acceptable polymer that can support a sufficient vacuum to enable the aspiration and dispensation of fluids without significant loss of accuracy.

Figures 10A, 10B:
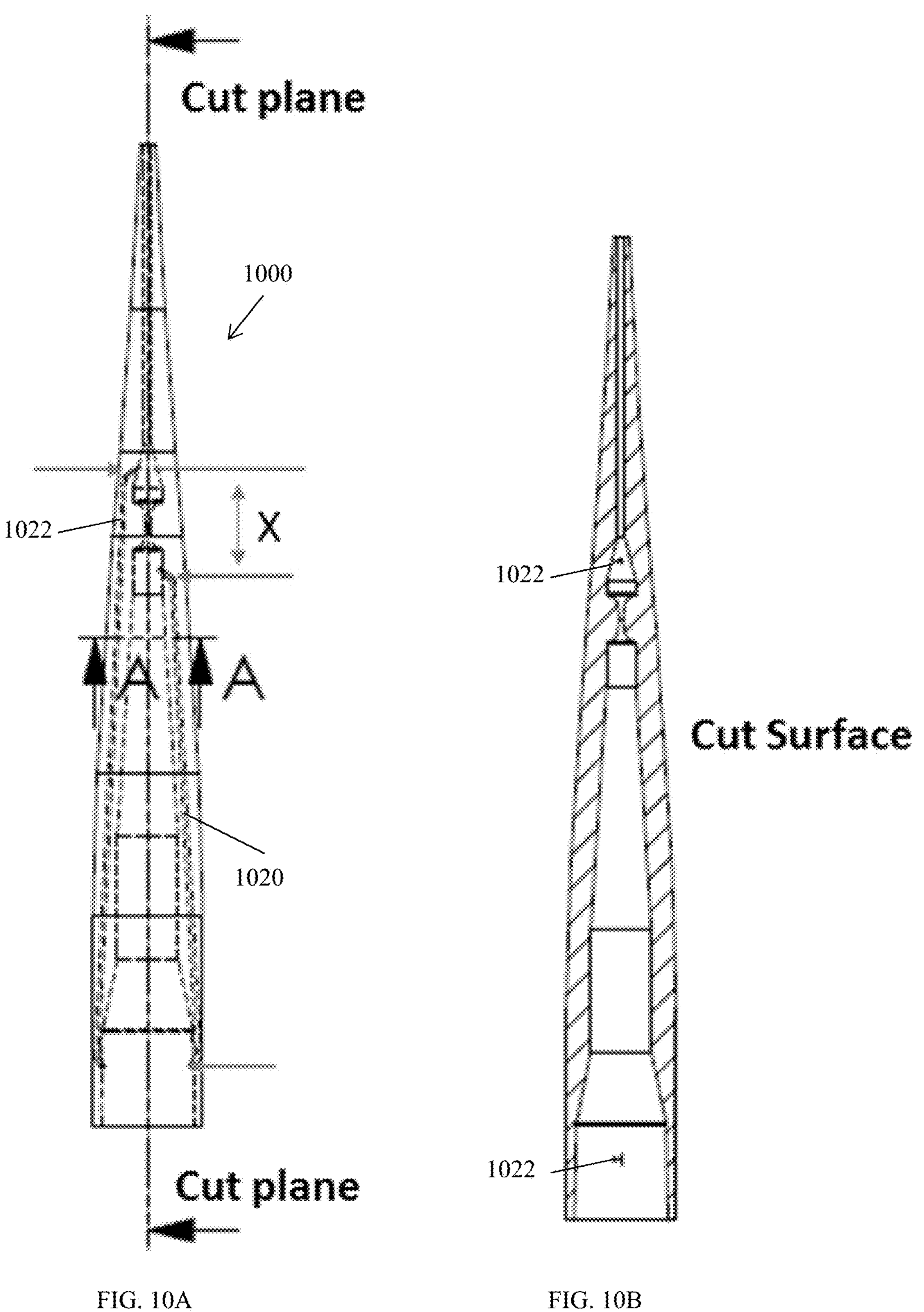
FIG. 10A is a schematic of another embodiment of a pipette tip.
FIG. 10B is a cross-section view of the pipette tip of FIG. 10A
Figures 12, 12A:
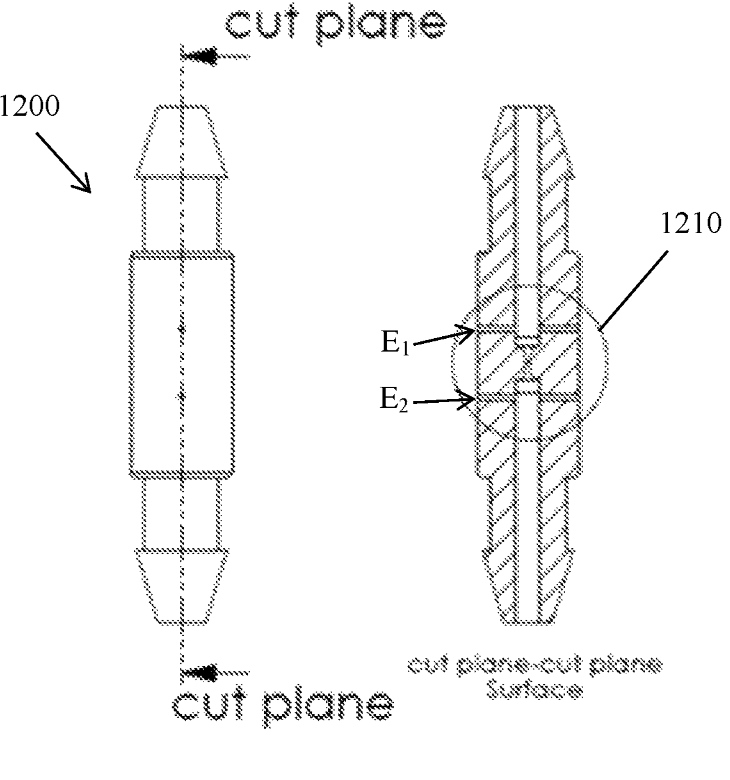
FIG. 12A is a schematic of an embodiment of a tube fitting.
Figure 12C:
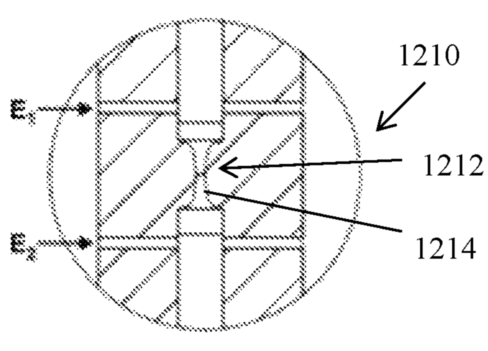
FIG. 12C is a section view of the tube fitting of FIG. 12A.
Figure 12D:
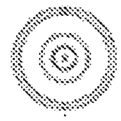
FIG. 12D is a top view of the tube fitting of FIG. 12A.

An example of an electrode configuration within a pipette tip is shown in FIGS. 10A-10C, with axial electrodes incorporated into the pipette tip using electrically conductive material. Pipette tip 1000 includes a first electrode 1020 connected to a flow path upstream of a constriction and a second electrode 1022 connected to the flow path downstream of the construction. A cross-sectional view normal to the flow path of pipette tip 1000 is shown in FIG. 10C with electrodes 1020, 1022 shown embedded within the pipette tip 1000.

The electrode configuration can be modified to include any design that matches the specific geometrical area or pipette tip perimeter in contact with the suspended cells in the reservoir section and constriction region of the pipette tip. For example, the pipette tip may include semi-circular or radial geometries of conductive elements that are in operative contact with a volume of suspended cells. Additionally, any number of electrodes can be included in a device, including at least one signal electrode and at least one reference electrode. Furthermore, multiple electrodes can compose a given signal or reference electrode. Alternative conductive elements to electrodes include, for example, electrically conductive thin films, high porosity metal foams, mesh electrodes, or any liquid diffusible membrane that can act as a conductor within the pipette tip. The electrodes, or other types of conductive elements, can be placed at any variation of a distance X, as shown in FIG. 10A. Additionally, conductive elements can be in physical isolation from the sample but in electrical contact. For example, high frequency electric fields can be used that can penetrate into the constriction region, even when electrodes are not in physical contact with a cell solution. As such, conductive elements can be placed in any configuration in which the elements are in operative arrangement with each other such that an electric field can be applied to a flow path. In the example configuration shown in FIGS. 10A-10C, the electrodes 1020, 1022 are physically embedded alongside the length of the pipette tip. The electrodes 1020, 1022 are isolated from each other and are connected to an external power supply that can be automatically connected upon the pipette tip being placed onto a liquid handler or handheld pipette device. Conductive elements can also be positioned, in part or entirely, external to a flow path. For example, electrodes, such as 1020, 1022, rather than being embedded within the material comprising the pipette tip, can be placed along an external length or an external perimeter of the pipette tip.

FIGS. 11A-11B illustrate an example of pipette tips used in conjunction with an automated liquid handling robot. A plurality of pipette tips 1100 are placed within a holder 1150. Holder 1150 can provide easy storage and distribution of the pipette devices for interfacing with, for example, a 24-well plate. Holder 1150 can optionally include electrodes arranged continuously from a first end 1120 to a second end 1122 to apply a voltage to the electroporation regions included in each of the pipette tips 1100. A nonconductive material can separate the conductive regions from one another within the holder 1150. Additionally, the electrodes can be positioned at a height at which aspiration and ejection into standard or custom multi-well plates is unobstructed. The compact design can incorporate electrodes across each micropipette device to deliver applied voltages, pulses of varying number and shape, and duty cycles in parallel. The design is scalable and can be easily reduced to 6-well plates or 12 well plates, or expanded to 384-well plates, 1536-well plates, or other sizes.

In other embodiments, electroporation devices are adapted to fit within other fluid handling or fluid transport structures. As used herein, fluid transport structure refers to any structure used to contain and transport fluid, such as pipette tips, tube fittings, and other flow-through devices. Fluid transport structures can enable flow through delivery of a cell suspension to a flow path of an electroporation structure contained therein. For example, electroporation structures can be included in tube fittings, as illustrated in FIGS. 12A-12D and 13A-13C. A barbed tube fitting 1200 is illustrated in FIGS. 12A-12D that can be configured to engage with rigid or flexible tubing, such as Tygon® tubing, for continuous flow genetic engineering applications involving large volumes of cells. As illustrated in more detail in FIG. 12C, the tube fitting 1200 can include transverse, wire-type electrodes $E_1$, $E_2$ arranged on either end of a construction 1212 of a flow path 1214 defined in the electroporation structure 1210.

Figures 13, 13A:
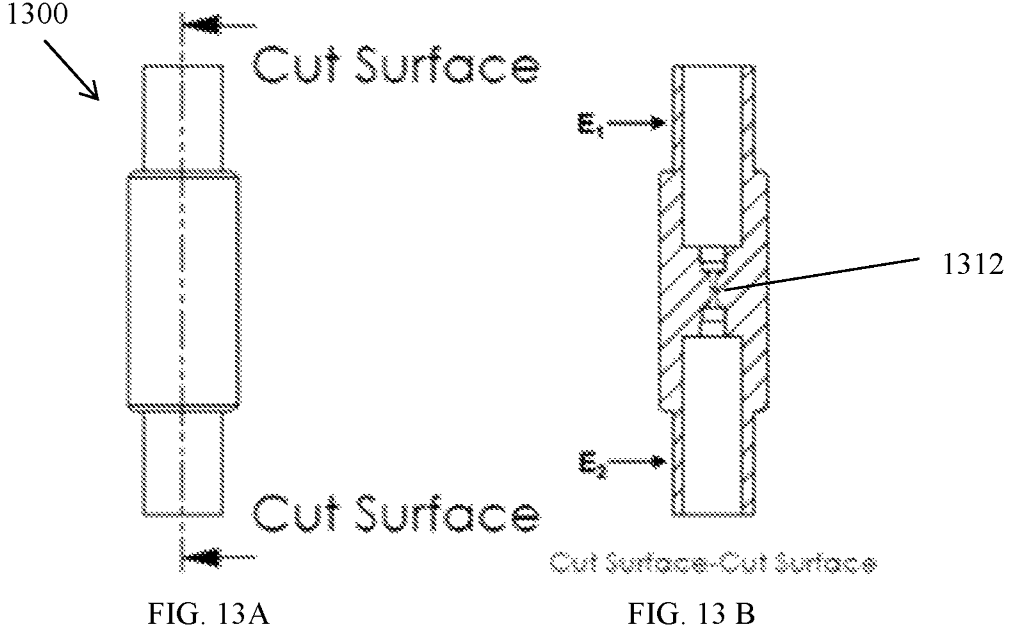
FIG. 13A is a schematic of anther embodiment of a tube fitting.
Figure 13C:
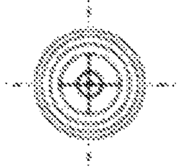
FIG. 13C is a top view of the tube fitting of FIG. 13A.
Figure 14:
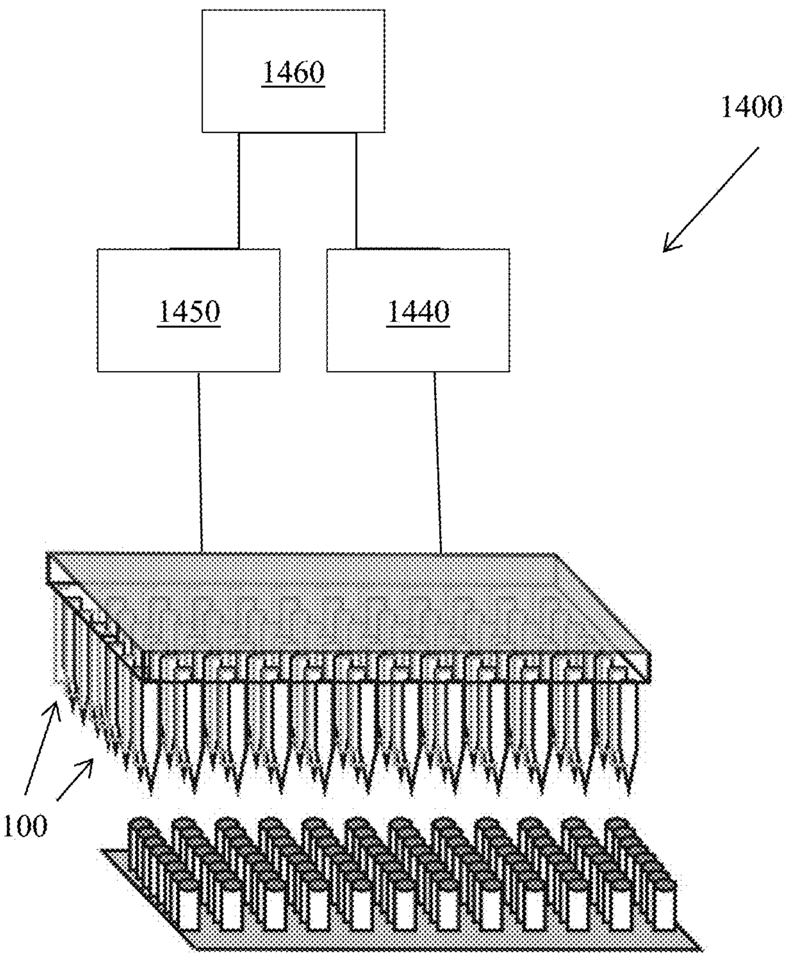
FIG. 14 is a schematic of an example of an electroporation system.

In another example, illustrated in FIGS. 13A-13C, tube fitting 1300 configured for a slip-fit engagement with tubing includes axially symmetric cylindrical electrodes $E_1$, $E_2$ arranged on either end of a constriction 1312.

While the example embodiments of electroporation devices shown in FIGS. 8A-13C generally include two electrodes $E_1$, $E_2$, additional electrodes can be included in any of the configurations. For example, the pipette tip 1000 of FIGS. 10A-10C could include three, four, five or more electrodes running axially along a length of the pipette tip.

In another embodiment, electroporation systems are provided. As illustrated in FIG. 1400, an electroporation system 1400 includes a plurality of fluid transport structures (e.g., pipette tips 100, 800, 900, or tube fittings 1200, 1300), which can be arranged in parallel and connected to a pump 1450 configured to induce a flow of cell solution to each of the fluid transport structures. A controller 1460 can optionally be connected to the pump 1450 and/or to a voltage source 1440. Controller 1460 can be configured to determine a flow rate, an applied voltage, a pulse distribution, and/or a duty cycle to be applied in an electroporation process. For example, through consultation with a look-up table or by manual user entry, controller 1460 can determine optimal electroporation parameters for a given cell type and can further control voltage source 1440 and/or pump 1450 to produce the desired electric field and flow rate in the fluid transport structures 100.

Amplifying the electric field, as used herein, refers to constricting the flow path such that the voltage within or across the flow path increases as a function of the constriction. It should be understood that different flow paths may have different constrictions, thus different amplifications; therefore, respective sources that produce adjustable voltages, duty cycles, or other electric parameters for the flow paths may be adjusted or pre-set such that each flow path has applied thereto substantially the same electric field (e.g., +/−0.1%, +/−1%, +/−5%, +/−10%) or selected different electric fields. In one embodiment, a controller may be employed to apply a calibration table to the respective sources to produce the electric fields customized per individual physical cell characteristic (e.g. size, type, growth phase) and buffer composition (e.g. ionic concentration).

Figures 15, 16:
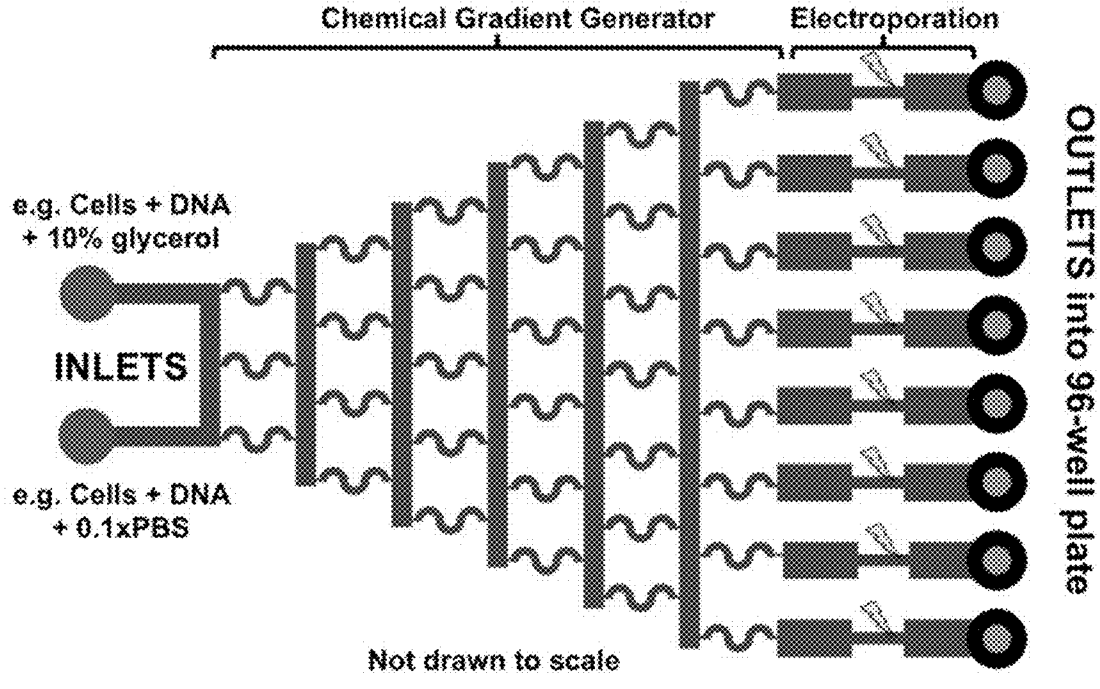
FIG. 15 is a schematic of an example of a multi-channel parallel microfluidic electroporation system.
FIG. 16 is perspective view of an example of a multi-channel parallel microfluidic electroporation system.

In another embodiment, electroporation devices include branched, multi-channel parallel microfluidic structures, as shown in FIGS. 15 and 16. The multi-channel devices can be used to generate a chemical gradient or concentration gradient across the eight outlets. As shown in FIG. 16, mixing between cell solutions provided at the inputs of the device occurs to produce cell solutions with a gradient of conditions. The chemical/concentration gradient generator provides the added functionality of testing varying media conditions in a rapid manner. However, the system can be easily modified such that a single electroporation media is used and all eight channels, such that identical experimental conditions are experienced at each outlet. This system can be used to screen electroporation conditions for novel organisms, or to simply produce a large number of transformed cells with organisms having known electroporation protocols (e.g., *E. coli* BL21 or *E. coli* DH5α).

Electroporation devices (e.g., pipette tips 100, 800, 900, and tube fittings 1200, 1300) and systems (e.g., system 1400) can be configured to operate at varying flow rates. Flow rates of, for example, about 0.25 mL/min to about 5 mL/min, or of about 0.5 mL to about 2 mL, can be provided. When arranged in parallel, such as in the gradient generator of FIGS. 15-16, each channel can operate at, for example, 125 μL/min, which in parallel, corresponds to processing eight 100 μL samples in 48 s. At such a flow rate, an entire 96-well plate can be processed within 10 minutes. This translates to more than 600 electroporation samples per hour, which, as compared with 20 samples per hour under the current cuvette paradigm, provides a significant improvement to processing times. The system can be adapted to operate at other flow rates, such as flow rates of 1 mL/min or more per channel, which, in turn, can result in 4800 samples processed per hour for sample volumes of 100 μL each.

Electroporation devices can also be configured to operate at varying applied voltages, pulse distributions, and duty cycles. For example, voltages of about 0.1 kV to about 3 kV (e.g., 0.1 kV, 0.25 kV, 0.4 kV, 0.5 kV, 1 kV, 1.5 kV, 2.0 kV, 2.5 kV, 3.0 kV, 3.1 kV), or of about 1.5 kV to about 2.5 kV can be applied. With regard to pulse distributions, pulses (e.g., symmetric square, symmetric rectangular, asymmetric square, asymmetric rectangular, triangular, sawtooth, and/or oscillating waveforms) can be provided with durations of about 0.001 ms to about 50 ms (e.g., 0.0099 ms 0.001 ms, 50 ms, 52 ms), about 0.1 ms to about 10 ms (e.g., 0.09 ms, 0.1 ms, 0.25 ms, 0.5 ms, 0.9 ms, 1 ms, 2 ms, 5 ms, 7 ms, 10 ms, 10.1 ms), or of about 5 ms to about 50 ms. A pulse duration of about 1 s can be of about the charging time of a cell membrane, when electroporation first appears. The pulses can be delivered at a duty cycle of about 25% to about 100% (e.g., 25%, 50%, 80%, 90%, 95%, 98%, 99%, 99.9%), or of about 50% to about 90%.

The applied voltage, channel geometry, and flow rate can be customized to each specific cell type. For example, large mammalian cells of about 10-50 μm may require an electric field ranging from about 0.5 kV/cm to about 2.5 kV/cm. In that case an applied voltage of 0.5 kV may be sufficient to maximize transfection rates and minimize cell death. However, if the cell type is a 1-2 μm bacterial cell, then an electroporation process may require an electric field ranging from about 5.0 kV/cm or about 7.5 kV/cm to about 12.5 kV/cm for successful genetic transformation. In this scenario, it can be beneficial to deliver an applied voltage of 2.0 kV or 2.5 kV (e.g., to a bilaterally converging flow path) to reach the electric fields needed for bacterial transformation.

The geometry and dimensions of a constricted flow path can also be adjusted to provide narrower or broader ranges of electric fields. Additionally, the constriction length can be increased in order to modulate the separation distance between conductive elements in order to achieve comparable electric fields with other applied voltages.

Flow paths having converging, diverging, bilaterally converging, or straight constrictions can have varying dimensions. An overall length of a constricted region of a flow path can be about 500 μm to about 5,000 μm. A maximum diameter of a flow path can be of about 500 μm to about 5,000 μm. A minimum diameter of a flow path can be of about 10 μm to about 500 μm.

Additionally, as high buffer concentrations can reduce transformation efficiency (e.g., due to deleterious heating and cell death), cell suspensions can include a conductivity buffer having a low buffer concentration, for example, of less than 1×10^−4 M, or of about 1×10^−9 M to about 1×10^−4 M (e.g., 1×10^−4 M, 1×10^−5 M, 1×10^−6 M, 1×10^−7 M, 1×10^−8 M, 1×10^−9 M).

Various transformation efficiencies can be achieved that are dependent, at least in part, on payload size and cell type or size. Transfection/transformation efficiencies can be of at least about 0.001%, at least about 0.01%, at least about 0.1%, at least about 1.0%, at least about 10%, at least about 20%, at least about 30%, at least about 50%, or at least about 90%.

Example embodiments of the present invention demonstrate successful transformation of prokaryotic and eukaryotic cells at higher efficiencies than conventional cuvette-based approaches, as further described in Examples 1-16 herein. Electroporation devices and systems of the present invention are scalable to accelerate genetic engineering of cells and help bring high value products to market such as new therapeutics and new materials. Currently, electroporation is the most robust method of genetic modification but is primarily performed manually leading to slow, unreliable, and low throughput genetic engineering. Embodiments of the present invention disclosed herein can perform genetic modification of cells nearly 10,000 times faster than the current state of the art while maintaining separation of samples to avoid cross-contamination. It is further estimated that embodiments of the present invention, enabling parallel, flow-through electroporation of large cell volumes, can outperform the state of the art electroporation techniques, based on 1000× increase in throughput and up to 10× increase in transformation efficiency as compared to cuvette based electroporation approaches. This innovation enables continuous flow genetic manipulation of cells in a platform that can be easily automated through integration with liquid handling robots for fast, reliable, and scalable cell engineering.

Cell transformation is an essential part of many fields of scientific research, including for example, the study of microbial pathogens, metabolic engineering, synthetic biology, and the human microbiome. Improved methods for cell transformation provide researchers a tool to more effectively leverage biology to tackle many of the scientific challenges of our day. As demonstrated by the results shown in the Examples herein (Examples 1-16), microfluidic flow-through electroporation can be an ideal method for genetic transformation of microbes due to its high transformation efficiency and small sample volume required.

Eukaryotic Cells

Eukaryotic cells present additional challenges for successful electroporation, as compared with prokaryotic cells, such as bacteria. As described above, critical parameters in electroporation include electric field magnitude and pulse characteristics, such as shape, duration, and number. However, other parameters also affect electroporation outcome, including, for example, DNA concentration in the sample and electrical conductivity (salt concentration) of the medium surrounding the cells (e.g., electroporation buffer). Buffers with lower ionic concentrations reduce arcing potential (electrical charges that occur due to high or excess salt concentration), reduce deleterious heating, and generally increase transfection efficiency. Notably, eukaryotic cells (including many protists) are highly sensitive to the experimental conditions that are optimal for electroporation, such as lower ionic concentrations. The low efficiency of electroporation resulting from the myriad of technical challenges has hindered progress in developing electroporation-based methods appropriate for various eukaryotic cells, such as aquatic protists.

Aquatic protists interact with other microbes to mediate nutrient flow in the sea. Development of genetically tractable model representatives can enable the systematic deciphering of gene-gene and gene-environment interactions, and can further enable an understanding of the processes underlying the roles of certain protists in biogeochemical cycling and evolution and ecology of the microbial Eukarya. Genetic manipulation of marine protists can make it possible to link genes of unknown function to cell behavior (e.g., colony formation, morphogenesis, cell-cell interactions), physiology (e.g., life cycle and reproduction type), particular biogeochemical cycles, and processes of interest, such as, nitrogen and carbon cycling, and production of climate active trace gases or initiation of harmful algal blooms. Development of successful transfection protocols for marine protists will enable advances in our understanding of their ecology.

In Example 14 herein, embodiments of the present invention demonstrate successful transformation of *Parabo caudatus*, a type of protist cell, with three differeng DNA plasmids (pEF-GFP, pUB-GFP, and pEYFP-Mitotrap) and enable the further refinement of conditions appropriate for electroporation of such cells. The ability to efficiently test a wide range of electroporation parameters, or to quickly transfect a target (or a collection of targets) with a range of genetic elements has significant advantages over cuvette-based methods for the field of genome editing. High-throughput transfection systems of the present invention offer processing of multiple samples (cultures or environmental samples), making effective investigations into the ecological roles of protists possible.

Another example of a eukaryotic cell, for which successful electroporation presents additional challenges, is *Plasmodium falciparum*. Malaria causes around 660,000 deaths per year, and *Plasmodium falciparum* is the protozoan parasite responsible for the most severe form of malaria in humans. It remains as one of the leading infectious causes of mortality and morbidity in humans with potentially 40% of the world population (3.4 billion) potentially exposed to infection and 207 million estimated clinical cases in 2012. There are many drugs that are available to clear the *Plasmodium* species infections but resistance has emerged to the majority of them. Therefore, there exists a critical need to develop new antimalarial compounds and significantly improved vaccine candidates. To advance the fundamental understanding of the molecular basis of drug resistance, it is imperative to genetically manipulate the malaria parasite (e.g., by knocking out or mutating genes, or introducing transgenes) to assess gene function. One of the main limitations in manipulating the *Plasmodium falciparum* genome has been the extremely low transfection efficiency of about one successful transfection per million cells with the best electroporation protocols available.

In Example 15 herein, embodiments of the present invention demonstrate successful transformation of *Plasmodium falciparum* at significantly higher transfection efficiencies, and enable the further refinement of conditions appropriate for electroporation of such cells.

EXEMPLIFICATION

Example 1: Transformation Efficiency of Pipette Tip Prototype

Figure 17:
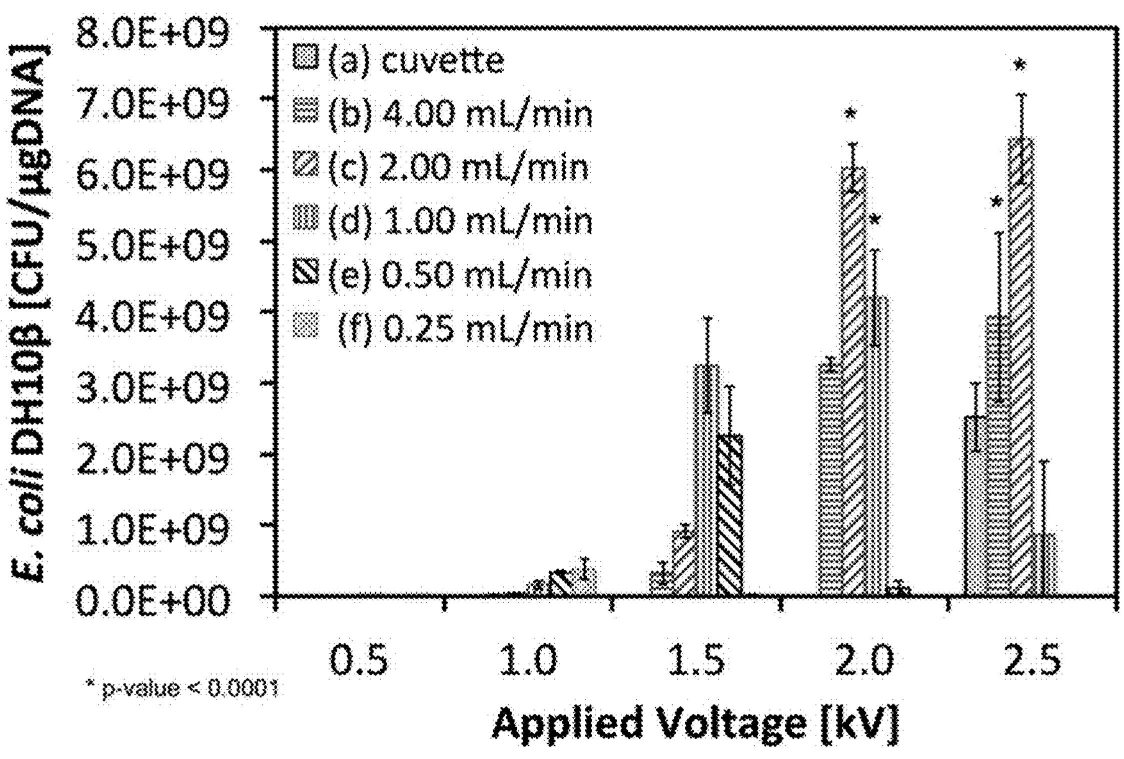
FIG. 17 is a graph displaying electroporation efficiency as a function of flow rate and applied voltage for continuous flow pipette tip devices compared to 2 mm cuvettes.

A prototype pipette tip (as illustrated in FIGS. 8A-8C) was fabricated in an EMBER 3D printer (Autodesk, Inc., Boston, MA). The pipette tip included a 3.0 mm long constriction that decreased bilaterally from 2.05 mm to 400 m in diameter. Performance of the pipette tip was characterized via continuous flow transformation of *Escherichia coli* DH10β ($OD_{600}$=0.5 at 1:20 dilution) with DNA (Parts Registry K176011) coding for green fluorescent protein (GFP) and ampicillin resistance. Specifically, the effect of applied voltage (0.5-2.5 kV) and flow rate (0.25-4.0 mL/min) on transformation efficiency was evaluated in triplicate. The results of electroporation efficiency as a function of flow rate and applied voltage, as compared with the results of electroporation using 2-mm cuvettes (VWR Signature™ Disposable Electroporation Cuvettes Catalog Number 89047-208), are shown FIG. 17. As shown in FIG. 17, flow rates of 1.0 mL/min (2.0 kV), 2.0 mL/min (2.0 and 2.5 kV), and 4.0 mL/min (2.5 kV) resulted in statistically significant (student's t-test) higher transformation efficiency than the traditional cuvette electroporation as denoted by the bolded stars (*).

Figure 18:
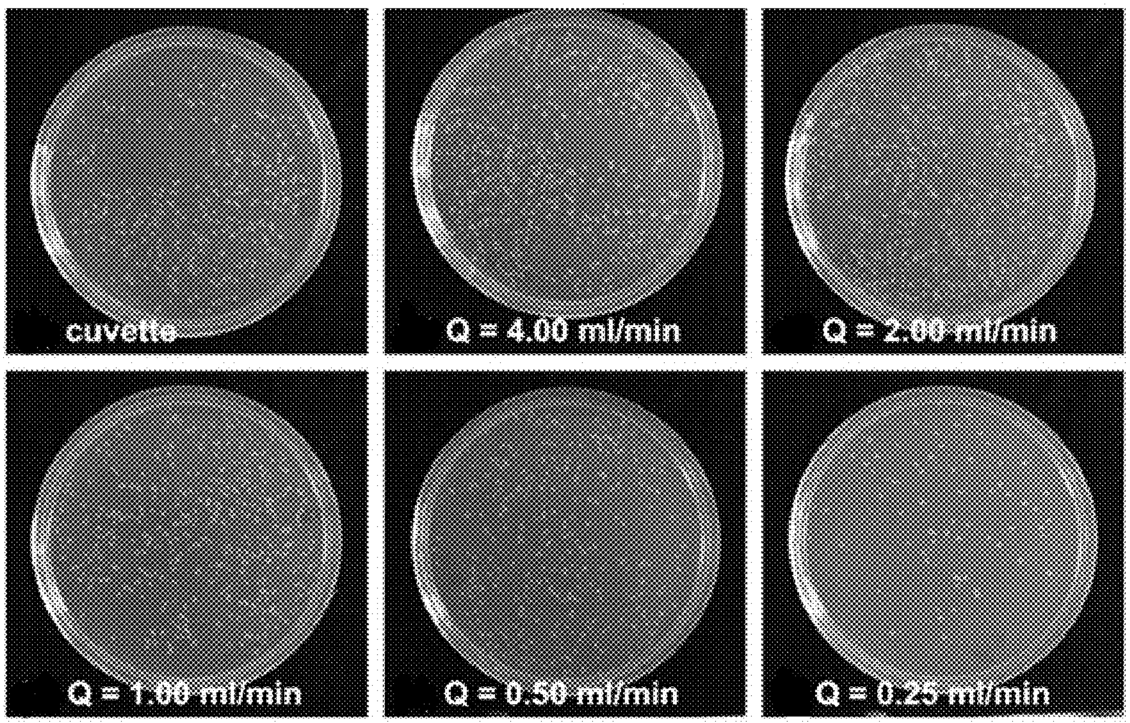
FIG. 18 is a photograph of Colony Forming Units (CFU) demonstrating successful transformation of bacterial cells in prototype pipette tips.

A photograph of the Colony Forming Units (CFU) in LB+Agar+Ampicillin plates resulting from the experiment is shown in FIG. 18, demonstrates successful transformation in *E. coli* DH10β. The highest delivered voltages per flow rate demonstrated superiority to the standard cuvette electroporation. The highest transformation efficiency was achieved by driving the sample at 2.0 mL/min (2.5 kV) and resulted in 7×10^9 colony forming units (CFU)/μgDNA after growth selection in Luria Broth (LB), Agar gel, and 50 μg/ml ampicillin plates, which is a 3× improvement over the standard cuvette electroporation. These results confirm that the prototype pipette tips have the capability of increasing transformation efficiency of microbial genetic modification versus the standard cuvette electroporation. In addition, due to the high flow rates, the experiment demonstrated the capability of processing large volume amounts in a relatively short amount of time. For example, operating at 2 mL/min equates to a total processing of 10 mL in 5 min, per each pipette tip. More importantly, by operating in parallel, in 5 minutes one can process large total volumes of 100 mL with 10 channels or even 1,000 mL (1 L) with 100 channels. The representative colony forming units (CFU) on the agar plates confirm that cells are indeed genetically engineered since they are expressing green fluorescent protein (GFP) and survive exposure to ampicillin, indicating that the cells have acquired antibiotic resistance.

Example 2: Modeling of Electric Field within Flow Channels of Pipette Tip Prototypes FIGS. 19-22 represent data from theoretical studies performed in COMSOL Multiphysics® Modeling Software (COMSOL, Burlington, MA) demonstrating that high electric fields are achieved within the constriction embedded in the flow path of Example 1.

Figure 19:
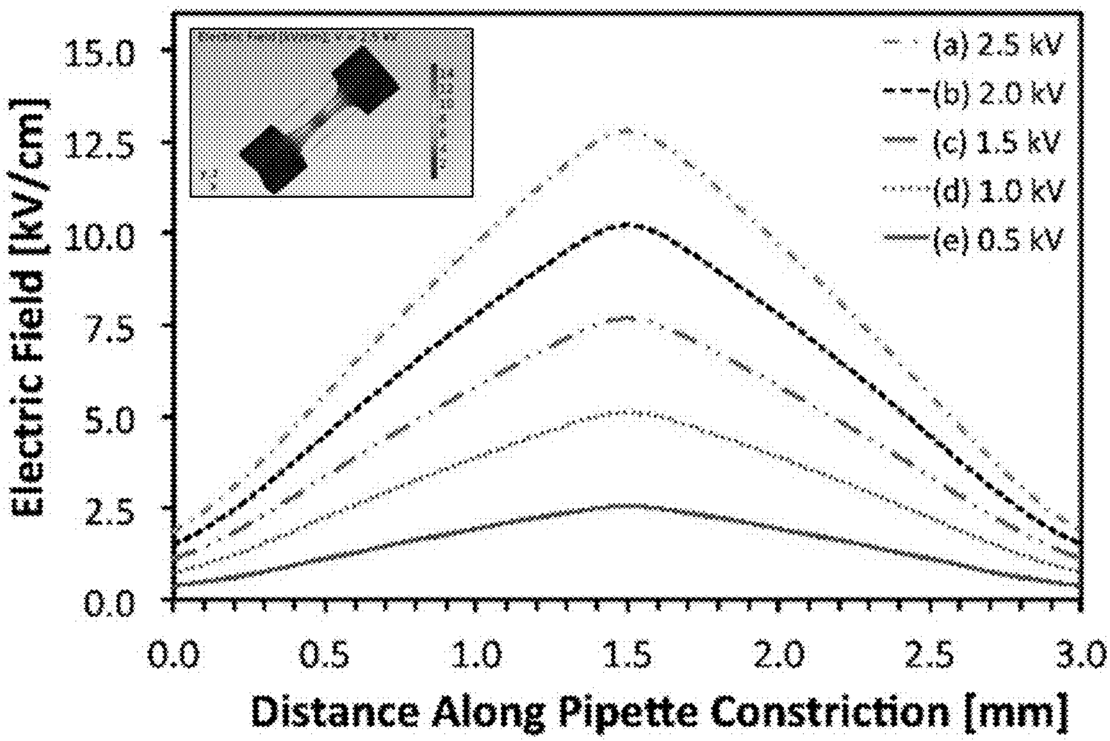
FIG. 19 is a graph displaying spatial electric field distribution along a longitudinal access of a constriction of a modeled flow path.

FIG. 19 illustrates spatial electric field distribution along a longitudinal axis of the constriction within the flow path. The simulated electric field curves for applied voltages ranging between 0.5 kV and 2.5 kV are shown and demonstrate a linear gradient along the centerline of the pipette tip channel. The geometric constriction linearly amplifies the electric field experienced by the cells. An applied voltage of 2.5 kV resulted in $E_{max}$=12.5 kV/cm. The inset shows the computed electric field distribution along the internal walls of the constrictions and confirms that the highest electric field occurs at the narrowest part of the constriction where the amplification factor is highest.

Figure 20:
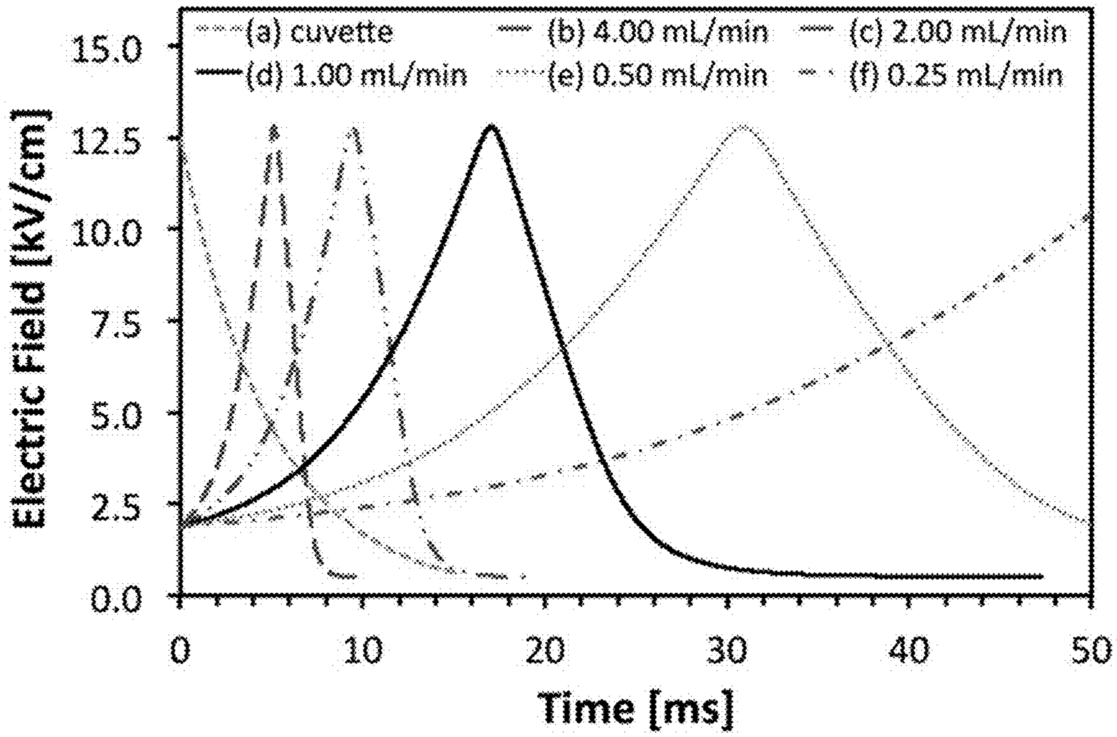
FIG. 20 is a graph displaying time-dependent electric field as experienced by cells flowing through a constriction of a modeled flow path.

Time dependent electric fields as experienced by cells as they flow through the geometric constriction with an applied voltage of 2.5 kV are shown in FIG. 20. The 2.0 mL/min and 4.0 mL/min flow rates have time traces comparable to that of conventional cuvette electroporation using an exponential decay waveform.

The electric field experienced by flowing cells along the centerline of the constriction demonstrates the impact of flow rate at an applied voltage of 2.5 kV (FIG. 20). The simulated conditions were identical to the experimental data shown in FIG. 17 in which cuvette electroporation was compared with pipette tip electroporation with applied voltages ranging between 0.5 kV and 2.5 kV and flow rates ranging between 0.25 mL/min and 4.00 mL/min. The static cuvette experiments used an applied voltage of 2.5 kV over a 2.0 mm electrode gap with an exponentially decaying electric pulse with a 5.0 ms decay constant (z=5.0 ms). Conversely, the pipette tip electroporation experiments were dynamic and coupled fluid flow with electric field exposure. Specifically, the flow rate determines the residence time that cells remain within the constriction region of high electric field. The lowest flow rate of 0.25 mL/min resulted in a residence time within the constriction of approximately 100 ms. Conversely, the highest flow rate of 4.0 mL/min resulted in residence time of approximately 7 ms. The other flow rates evaluated resulted in residence times within the constriction of approximately 50 ms (0.5 mL/min), 25 ms (1.0 mL/min), and 13 ms (2.0 mL/min). As demonstrated by the electric field versus residence time curves, in the bilaterally constricting geometry the cells are exposed to an increasing electric field that reaches a maximum at the narrowest part of the constriction and then decreases until the cells exit the constriction.

Figure 21:
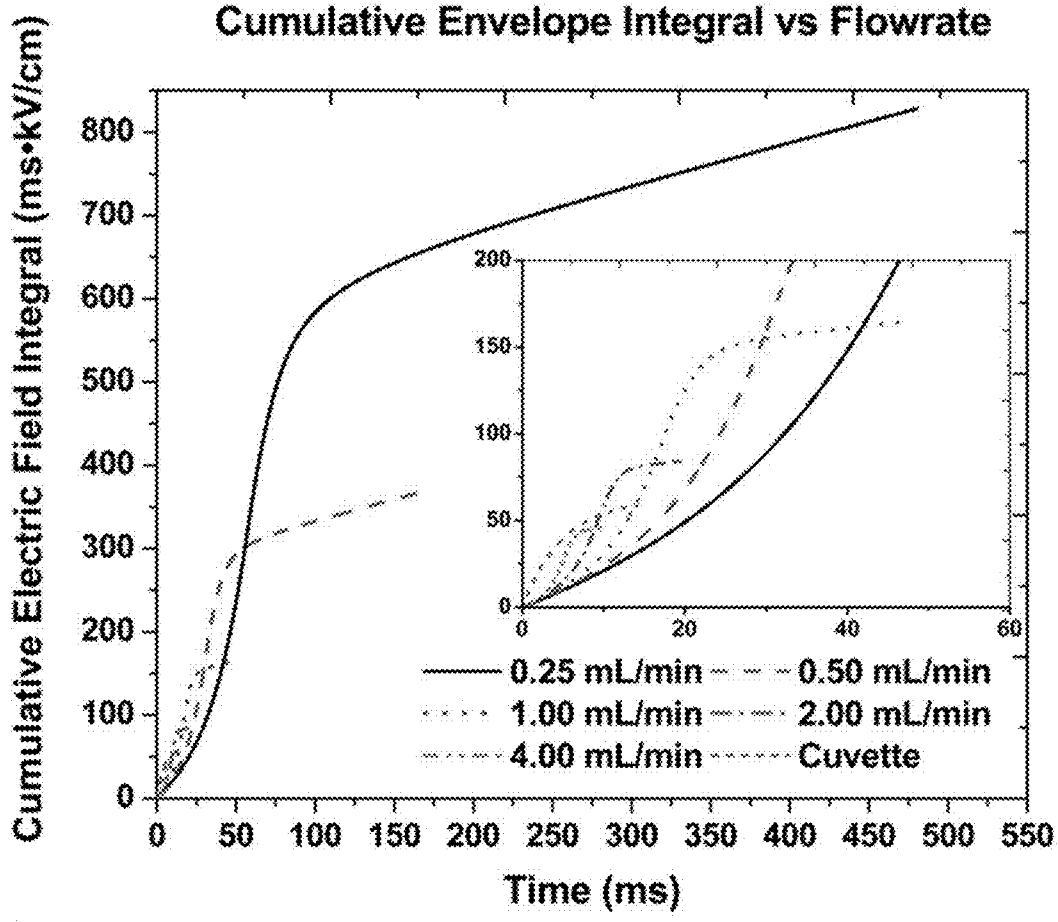
FIG. 21 is a graph displaying cumulative electric field versus time as experienced by a cell flowing through a constriction of a modeled flow path.

The cumulative electric field integral (e.g., area under the curve) of the time dependent electric field curves (FIG. 20), as experienced by a flowing cell through the centerline of the channel geometry were computed and are shown in FIG. 21. The cumulative electric field provides insight as to the amount of energy that flowing cells experienced as they flow through the constriction. As expected, the slowest flow rate had the largest energy transfer to each cell since the residence time was the longest. The lowest energy transfer occurred with the highest flow rate, as can be seen in the FIG. 21 inset since these samples had the lowest residence times. Interestingly, the energy deposited in the cuvette electroporation sample (2.5 kV) was higher than the 4.0 mL/min case (2.5 kV) but lower than the 2.0 mL/min (2.5 kV). However, both of the dynamically flowing samples resulted in statistically significant higher transformation efficiency than the cuvettes. This confirms that flow is beneficial for achieving favorable genetic engineering rates at least due to the ability to dissipate heat more efficiently than in static cuvette electroporation experiments.

Figure 22:
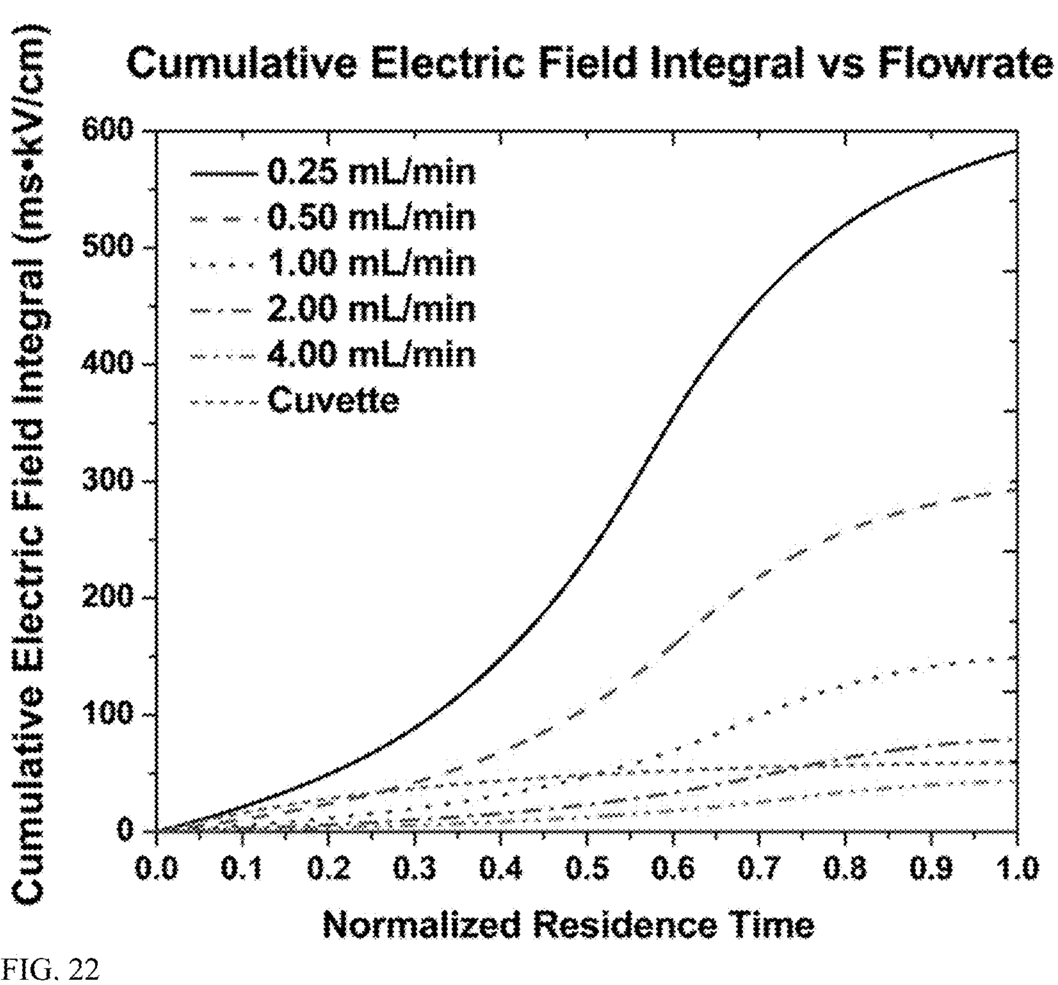
FIG. 22 is a graph displaying cumulative electric field versus normalized residence time as experienced by a cell flowing through a constriction of a modeled flow path.

FIG. 22 shows the cumulative electric field integral normalized by the residence time of cells for each of the flow rates evaluated. Similar to the results shown in FIG. 21, the slowest flow rate of 0.25 mL/min resulted in the highest energy transfer to the sample and lowest transformation efficiency. Conversely, the fastest flow rate of 4.0 mL/min resulted in the lowest energy transfer and highest transformation efficiency. Importantly, the normalized energy transferred in the standard cuvette electroporation is between the 2.0 mL/min and 4.0 mL/min flow rate cases evaluated experimentally and computationally. As depicted in FIG. 17, the transformation efficiencies for the 2.0 mL/min (2.5 kV) and 4.0 mL/min (2.5 kV) resulted in higher transformation efficiencies versus the static cuvette electroporation. This result confirms the benefit of dynamically flowing cells in order to achieve higher transformation efficiencies than those achieved in static cuvette experiments.

Example 3: Modeling of Electric Field within Flow Channels of Varying Geometries A computational model was developed to determine channel geometries and experimental conditions that can result in increased throughput and increased transformation efficiency. The computational models coupled electric, hydrodynamic, and thermal responses in COMSOL Multiphysics® Modeling Software v5.1 (COMSOL, Burlington, MA) for bilateral, converging, diverging, and straight constriction geometries studied. The goal was to operate with experimental conditions that are favorable for bacterial transformation without significantly compromising cell viability due to extremely high electric fields or exposure to lethal temperatures. Specifically, the electric field distribution within the microfluidic devices was computed by solving the Laplace equation:

$$-\nabla \cdot (\sigma \nabla \varphi) = 0 \tag{1}$$

where σ is the electric conductivity of the electroporation buffer and φ the electric potential (Table 1). An electric conductivity of 0.002 S/m was measured for 10% (v/v) glycerol; however, it was assumed that the conductivity of the entire sample increased 5× in order to conservatively incorporate the increase in conductivity that occurs during electroporation. The fluid flow was computed by solving 3D steady-state Navier-Stokes and continuity equations. Additionally, the temperature distribution was determined by coupling the Joule heating term and fluid velocity distributions within the Heat Transfer in Fluids module, using similar numerical techniques to those described by Gallo-Villanueva et al., Electrophoresis, 2014, 35, 352-361, the entire content of which is incorporated herein by reference. The following assumptions were made in the model: a) electrical insulation at every boundary except for the electrodes with $\varphi = V_0$ and $\varphi = 0$; b) specific flow rates at the inlet and no pressure at the outlet; c) no-slip conditions at the channel walls; d) incompressible fluid; and e) thermal insulation on the channel walls.

TABLE 1

Physical parameters used in numerical simulations

| Symbol | Quantity | Value | Units |
|---|---|---|---|
| σ | Electric Conductivity | 0.01 | S/m |
| ρ | Density | 1000 | kg/m$^3$ |
| μ | Dynamic Viscosity | 1e−3 | Pa · S |
| k | Thermal Conductivity | 0.58 | W/(m · K) |
| $c_p$ | Heat Capacity | 4184.4 | J/(kg · K) |
| $T_i$ | Initial Temperature | 294.15 | K |

Figure 24:
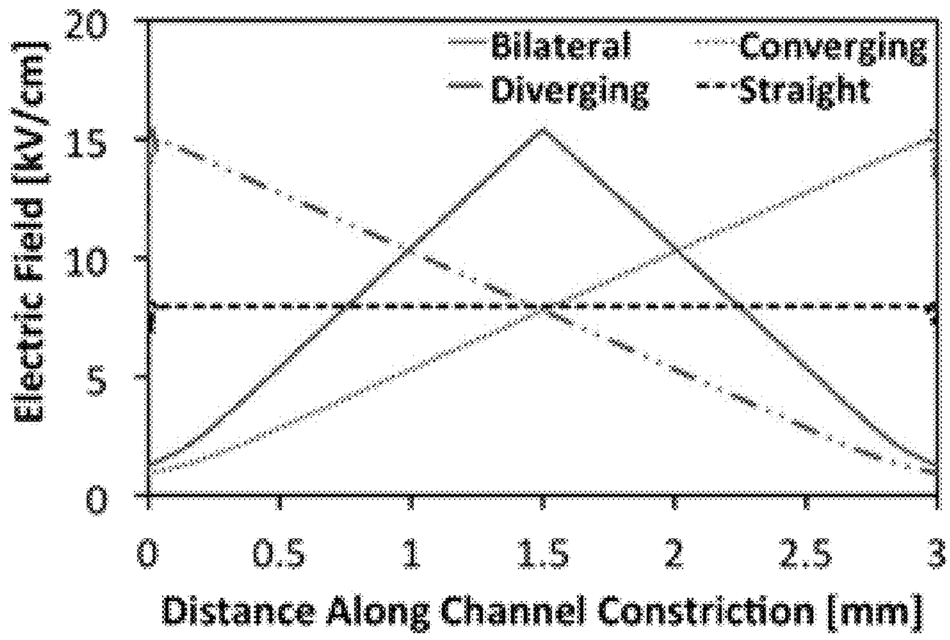
FIG. 24 is a graph illustrating electric field strength along a centerline of the constriction regions in each of the microchannels of FIGS. 23A-23C when a voltage of 2.5 kV is applied.

To evaluate the effect of channel geometry on transformation efficiency, four unique designs were compared with traditional 2 mm electroporation cuvettes, as shown in FIG. 23A-C. The first geometry is bilaterally converging (FIG. 23A) with a minimum channel width of 50 μm at the center of the constriction. A minimum channel width of 50 μm is assigned for both the converging and diverging constrictions to maintain consistency across the channel geometries (FIG. 23B). The straight microchannel (FIG. 23C) is 50 μm in width, with a constant cross-sectional area along its entire 3 mm length. All four microfluidic channel geometries were 100 μm in depth. Additionally, FIGS. 23A-C show the electric field distributions corresponding to the four constriction geometries that were evaluated experimentally for inducing genetic transformation of the electrocompetent *Escherichia coli* DH10β and *Escherichia coli* K12 wildtype (WT) (see Example 7). *E. coli* DH10β was selected for transformation because it has been widely used in molecular biology as a model organism. Additionally, the transformation efficiency of *E. coli* K12 wildtype was evaluated because it contains native restriction and modification systems for DNA methylation and degradation, making it more challenging to engineer. From these numerical simulations at an applied voltage of 2.5 kV, it can be appreciated that the constrictions with non-uniform cross-sectional areas ($E_{max}$=15-17 kV/cm) are able to amplify the electric field strength to magnitudes that are roughly two times higher than the microchannel with a uniform cross-sectional area ($E_{max}$=9 kV/cm). The ability of the non-uniform designs to amplify the electric field more efficiently than straight channels is advantageous since it requires lower applied voltages to achieve the same maximum electric field. This translates into reduced deleterious effects resulting from the pulsed electric fields, such as excessive Joule heating or pH changes that could affect cell viability and prevent successful transformation. FIG. 24 plots the electric field along the centerline of each 3.0 mm constriction and further corroborates that a non-uniform geometry is advantageous to reach electric fields required for electroporation for a given applied voltage.

Figure 25:
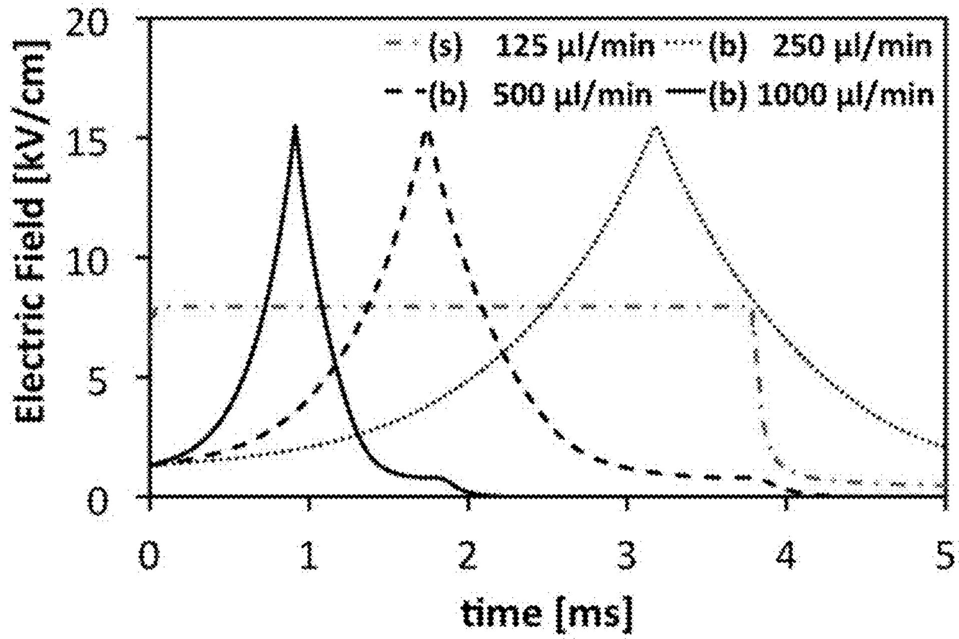
FIG. 25 is a graph illustrating time-dependent electric fields as experienced by cells flowing through the microchannels of FIGS. 23A-23C.

The simulations show that varying the channel geometry results in different time dependent electric field exposure for cells flowing through the microchannels. In particular, the time dependent electric field experienced by cells in a microchannel of non-uniform cross section can be challenging to achieve with standard electronics. FIG. 25 shows the electric field profiles that cells located at the inlet of the constriction will experience due to the flow profile during the 5-ms ON time period during which the square pulse is delivered. In this case, the microchannel geometries from FIGS. 23A-23C are identified as bilateral (b) and straight (s) for convenience. As can be seen by the curves representing the bilateral (b) geometries, the flow rate influences the exposure time for which cells will experience the electric field. Specifically, a flow rate of 250 μL/min (black—dotted)

exposes the cells to a longer time in an elevated electric field and also requires more time to reach the maximum electric field compared to higher flow rate conditions. Conversely, a flow rate of 1000 μL/min (black—solid) generates a shorter exposure of the cells to the high electric field, essentially reducing the 'pulse duration' and reaching the maximum electric field faster. The straight channel geometry (red—dash dot) exposes cells to uniform electric field strength until they exit the constriction. The ability to modulate the exposure duration and specific waveform that the cells experience in a flow-through manner allows for further optimization of electroporation protocols for prokaryotic or eukaryotic cells. Furthermore, continuous and variable electric fields allow for exposure of cells to high electric fields capable of electroporating the cell envelope. Additionally, the device has regions of low electric field to facilitate electrophoretic-assisted transport of DNA into cells.

Figure 26A:
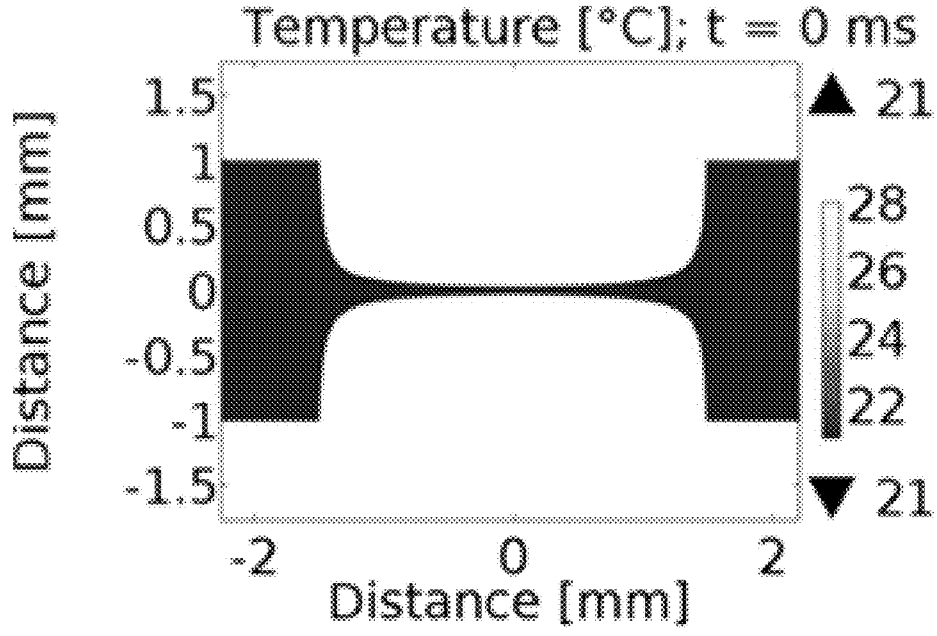
FIG. 26A is a graph illustrating temperature distribution in the bilaterally converging microfluidic channel of FIG. 23A before a pulse is applied.
Figure 26B:
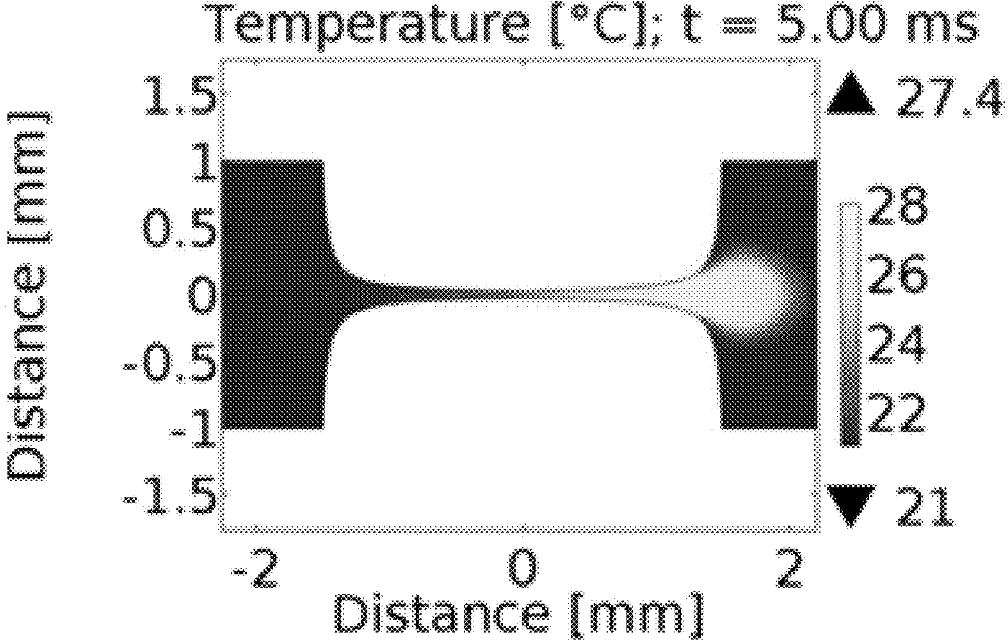
FIG. 26B is a graph illustrating temperature distribution in the bilaterally converging microfluidic channel of FIG. 23A after a first 5 ms square pulse is applied with an applied voltage of 2.5 kV in an experimental sample flowing through the device at 500 μL/min.
Figure 26C:
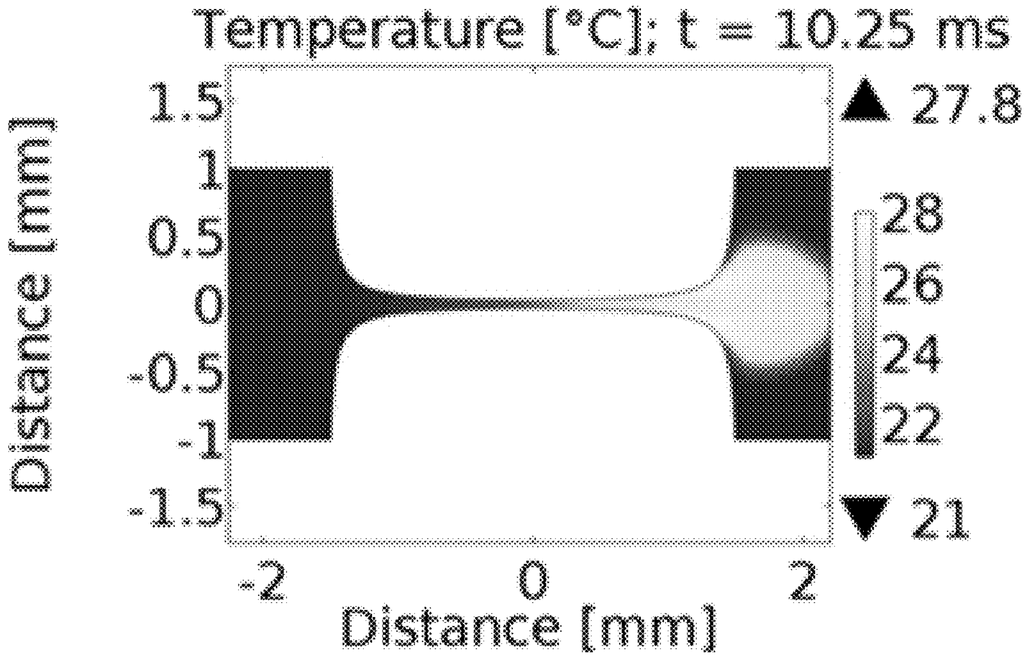
FIG. 26C is a graph illustrating temperature distribution in the bilaterally converging microfluidic channel of FIG. 23A after a second 5 ms square pulse is applied, separated by 250 μs from a first pulse, with an applied voltage of 2.5 kV in an experimental sample flowing through the device at 500 μL/min.

As opposed to applications in mammalian cells (Ø~10 μm) that require electric fields in the range of 1-2 kV/cm for successful transfection, bacteria (Ø~1 μm) require fields of 10-20 kV/cm for successful transformation. The use of higher electric fields increases the risk of deleterious Joule heating and compromised cell viability. Therefore, Joule heating generated during the 5-ms pulse delivery in the bilateral channel with a prescribed flow rate of 500 μl/min was simulated to ensure that cells would not be exposed to lethal temperatures and remain viable (FIGS. 26A-26C). FIG. 26A shows the temperature distribution at the conclusion of the 5-ms pulse and confirms a localized mild temperature increase (~6° C.) even after assuming a conservative 5× increase in electrical conductivity during electroporation due to bacterial permeabilization. The numerical results demonstrate that this flow rate is able to transport the heated fluid sample outside of the high electric field region within 250 μs after pulse completion (FIG. 26B). The 5-ms pulses were delivered 250 μs after pulse completion to maximize the fraction of electroporated cells. Implementing faster flow rates such as 1000 μL/min, 2000 μL/min, and 4000 μL/min in the bilateral microchannel are non-lethal as well since the cells experience the high electric field for a shorter duration. Therefore, the modeling results numerically confirm that a flow-through transformation protocol that requires high electric fields should employ a combination of strong pulsed electric fields, low buffer conductivity, and relatively high flow rates in order to prevent exposing cells to lethal temperatures. This combination of parameters is valid for the four geometries evaluated but can be expanded to other unique geometries as well.

Example 4: Test System Setup for Flow-Through Bacterial Electroporation

Figure 27:
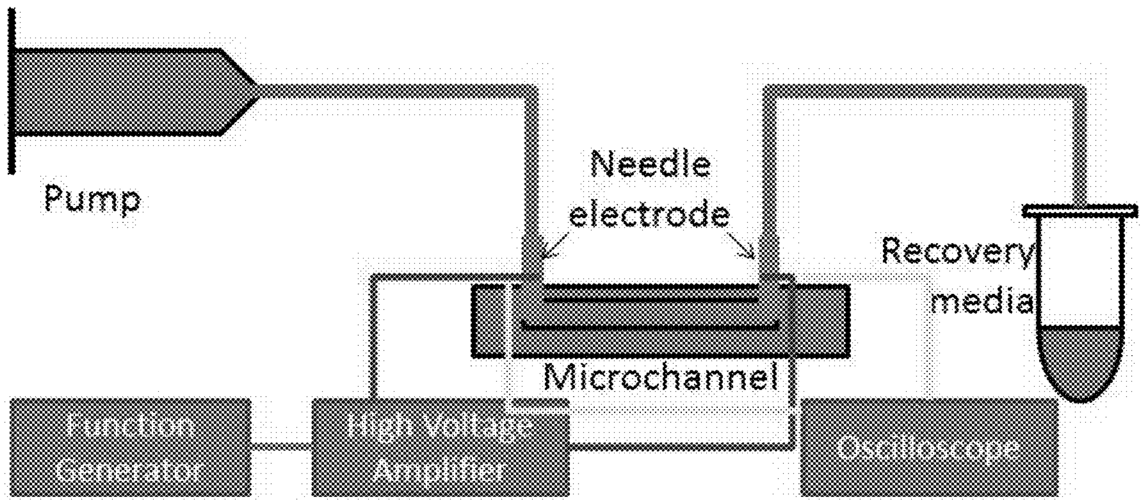
FIG. 27 is a schematic illustrating system components of an electroporation system.

FIG. 27 is a schematic illustrating test system setup. Cell suspensions (see Example 6) were driven by a syringe pump (Pump 11 Pico Plus Elite Syringe Pumps, Harvard Apparatus, Holliston, MA) at a particular flow rate for each experiment. Specifically, the samples in the straight channels were driven at 125 μL/min and the samples in the bilateral, converging, and diverging microchannels at 500 μL/min. The differences in flow rates were to ensure that the residence time within the constrictions was comparable due to a 4× volume difference between the non-uniform and uniform constriction geometries. Additional experiments were performed in the bilateral (250-4,000 μL/min) and straight (62.5-1,000 μL/min) microchannels to evaluate the influence of flow rate on transformation efficiency. The syringe pump, microchannel, and recovery media contained in Eppendorf® tubes were connected with PVC tubing (ID 1/16 inch, OD 1/8 inch, Tygon® Tubing, McMaster Carr, Elmhurst, IL). The cell suspensions were driven through the microchannel and into recovery media. The electric field was applied from a function generator (Agilent 33220A, Agilent Technologies Inc., Lexington, MA) to the microchannel with a pair of 16-gauge stainless-steel dispensing needle electrodes. Signals from the function generator were amplified about 1000× by a high voltage power amplifier (TREK Model 623B high-voltage power amplifier, Trek Inc., Lockport, NY). The amplified electric signal was verified by an oscilloscope (DSO-X 2022A, Agilent Technologies Inc., Lexington, MA) through a high-voltage differential probe (Keysight® N2891A, Keysight Technologies, Santa Rosa, CA) connected in parallel to the electrodes.

Example 5: Fabrication of Protocol Devices

The photomasks were designed in AutoCAD® 2014 (Autodesk, San Rafael, CA) with geometries as in FIG. 23A-23C and printed by Fine-Line Imaging, Inc. (Colorado Springs, CO). The microchannels were fabricated using standard soft lithography techniques described previously by Garcia et al., Scientific reports, 2016, 6:21238, the entire content of which is incorporated herein by reference. SU-8 (SU-8 2050, Micro-Chem, Westborough, MA) molds were patterned on silicon wafer using photolithography. After photolithography, the surfaces of the SU-8 master molds were treated under vacuum for 2 hours with tridecafluoro-1,1,2,2-tetrahydrooctyl-1-trichlorosilane (Sigma Aldrich, St. Louis, MO) before being used for molding. Next, the SU-8 masters were used to mold polydimethylsiloxane (PDMS) using Sylgard 184 (Dow Corning, Midland, MI) at a 10:1 ratio after 2 hour vacuum for air bubble removal. The PDMS devices were bonded to a glass slide after a 45 second plasma treatment and placed in an oven at 75° C. overnight before subsequent experiments.

Example 6: Cell Culture Preparation

*E. coli* DH10β (New England Biolabs, Ipswich, MA) and *E. coli* K12 wildtype (Yale *Coli* Genetic Storage Center, CGSC 4404) were cultured overnight in a 3-mL test tube of Luria Broth (LB) medium. The following morning, 333 μL of cell culture was transferred to 100 mL of fresh growth media and allowed to grow to exponential phase before electroporation ($OD_{600}$=0.5). Then, cell suspensions were concentrated 20× via centrifugation at 3500 rpm at 4° C. for 5 min (F0650 rotor, Allegra® 64R Benchtop Centrifuge, Beckman Coulter, Indianapolis IN). After the concentration step, the supernatant was discarded and the cells were washed three additional times with pre-chilled to 4° C. 10% (v/v) glycerol and centrifugated at 8000 rpm for 5 min each time (F1202 rotor, Allegra® 64R Benchtop Centrifuge, Beckman Coulter, Indianapolis IN). Cell concentration was confirmed via spectrophotometer measurement of $OD_{600}$=0.5 at a 1:20 dilution ratio. Immediately prior to the electric pulsing, ampicillin resistance and green fluorescent protein (GFP) encoding DNA plasmids (Parts Registry K176011) were added to the cell solution for a final concentration of 1.0 ng/μL. Plasmid DNA was extracted using a QIAgen® spin miniprep kit (QIAgen, Hilden, Germany).

Example 7: Cell Electroporation Using Protocol Devices and Cuvettes

Figure 28A:
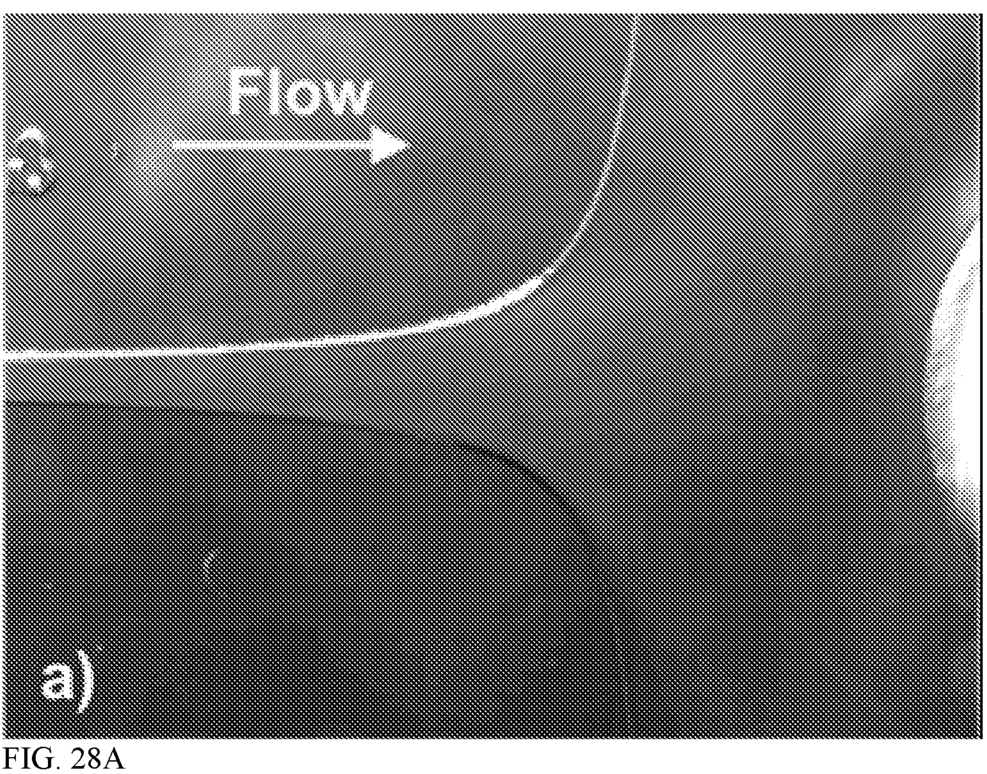
FIG. 28A is a photograph of flow-through of *E. coli* K12 wildtype cells being electroporated in a bilaterally converging microchannel at a flow rates of 500 μL/min with an applied voltage of 2.5 kV and 5-ms square electroporation pulses with a 95% duty cycle.
Figure 28B:
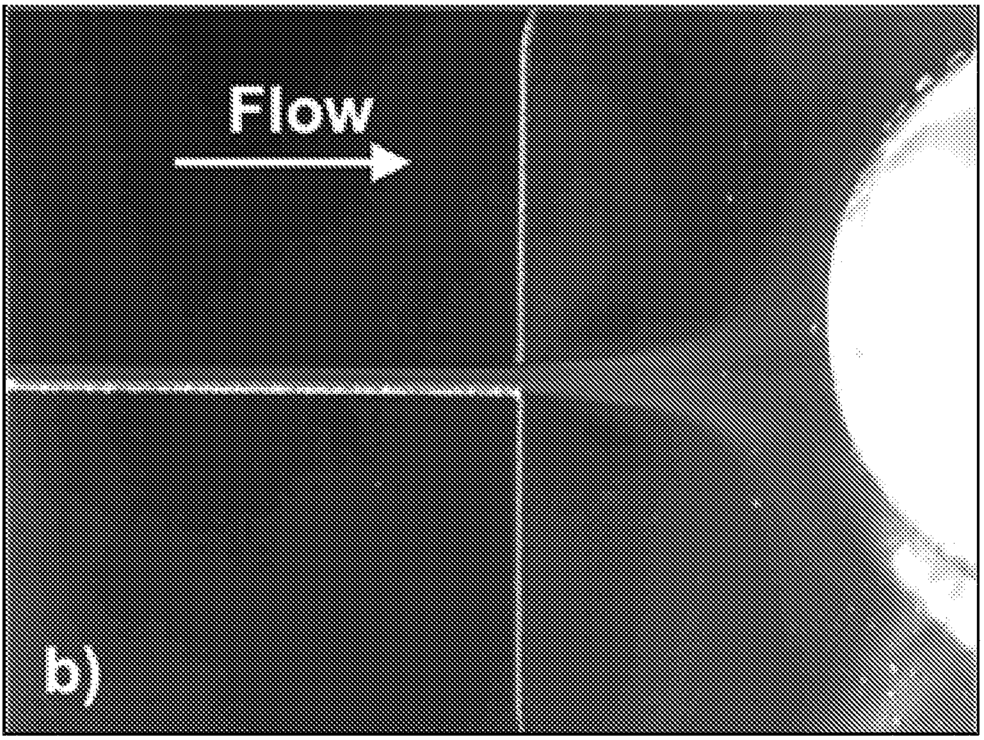
FIG. 28B is a photograph illustrating flow-through of *E. coli* K12 wildtype cells being electroporated in a straight microchannel at a flow rates of 125 μL/min with an applied voltage of 2.5 kV and 5-ms square electroporation pulses with a 95% duty cycle.

For cell electroporation in the microchannels (FIGS. 23A-23C), three independent cell samples of 100 μL with 1.0 ng/μL DNA plasmids were suctioned into the Tygon® tubing. Square wave pulses with 5-ms ON and 250-μs OFF cycles (95% duty cycle) were applied to the microchannel through the dispensing needle electrodes with alternating polarity between the pulses to reduce electrolytic effects. Photographs of cells flowing through the bilaterally converging and straight microchannels are shown in FIGS. 28A-28B. After flowing through the microchannel, each 100 μL cell sample is added to 900 μL of LB at room temperature into a 24-well plate and placed in a shaking incubator (250 rpm) at 37° C. for 1 hour recovery. The *E. coli* DH10β and *E. coli* K12 wildtype were diluted by 100,000× or 1,000×, respectively prior to selection plating. A total of 100 μL from each sample was plated on ampicillin (50 μg/ml) containing LB agar plates, and incubated overnight before colony forming units (CFU) quantification.

Positive controls were created by electrotransforming *E. coli* DH10β and *E. coli* K12 wildtype cell suspensions using traditional 2 mm electroporation cuvettes (VWR, Radnor, PA). A total cell suspension volume of 200 μL with 1.0 ng/μL DNA was pipetted into pre-chilled electroporation cuvettes from the same cell population as the experiments performed in the microchannels. A MicroPulser™ (Bio-Rad, Hercules, CA) was used to pulse the cell suspension at 2.5 kV with about 5 ms time constant. Immediately after delivering the electric pulse, 95 μL of electroporated cells was added to 900 μL of room temperature LB media into a 24-well plate. In order to maintain the number of cells constant with the microchannel experiments, an additional 5 μL of cell-DNA mixture was added into the recovery well and the plate was placed in a shaking incubator (250 rpm) at 37° C. for 1 hour. Finally, 100 μL of the diluted cell suspension was pipetted onto the ampicillin (50 μg/ml) containing LB agar plates, and incubated overnight before quantifying CFU using the same dilution ratios as the flow-through experiments.

After overnight incubation, photos of the agar plates were taken with a Nikon digital camera (Nikon, Tokyo, Japan). Colony forming units (CFUs) were counted by analyzing the photos in the software NICE (NIST's Integrated Colony Enumerator, version 1.2.1) and imageJ (NIH). Here, transformation efficiency was defined as the CFU in ampicillin containing LB agar plates per 1.0 μg DNA.

Example 8: Duty Cycle Evaluation for Maximum Sample Transformation

Figure 29:
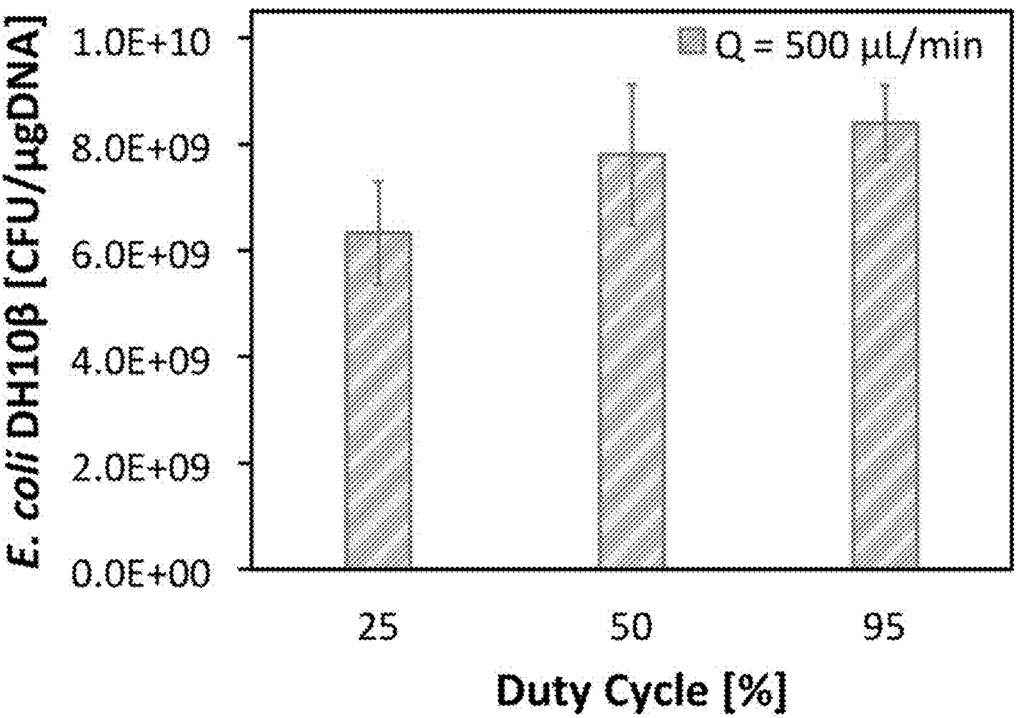
FIG. 29 is a graph illustrating *E. coli* DH10β transformation in a bilateral microfluidic device at 25%, 50%, and 95% duty cycles with an applied voltage=2.5 kV, 5-ms square electroporation pulses with alternating polarity after each pulse, and 500 μl/min flow rate.

The duty cycle of the pulses was modulated by defining the OFF time in between the 5-ms square pulses to evaluate the effect of pulse repetition frequency. The goal of characterizing the duty cycle is to maximize the relative amount of transformed sample during flow-through electroporation. Specifically, OFF time durations of 15 ms, 5 ms, and 250 μs between polarity changes correspond to 25%, 50%, and 95% duty cycles, respectively. In all the *E. coli* DH10β samples evaluated, high transformation efficiencies of ≥6×10^9 CFU/μgDNA were achieved with the flow-through techniques using a 500 μL/min flow rate, as shown in FIG. 29. A one-way ANOVA test gives p=0.113, which suggests a statistically insignificant correlation between transformation efficiency and duty cycle. For subsequent flow-through electroporation experiments (Examples 9-11) a duty cycle of 95% was selected to maximize the percentage of transformed cells.

Figure 30A:
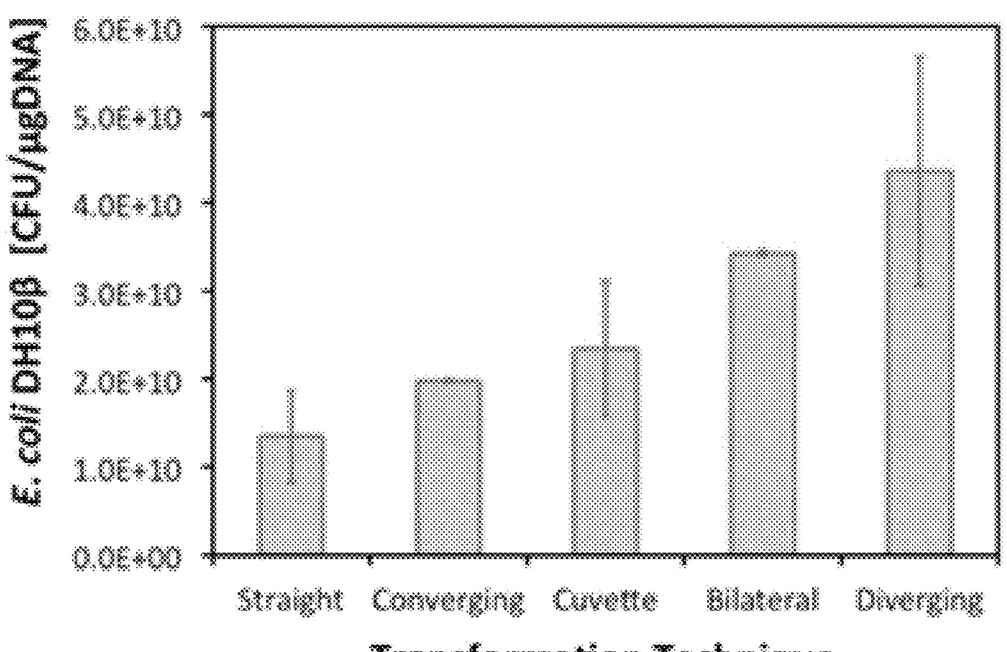
FIG. 30A is a graph illustrating transformation efficiency after flow-through electroporation of *E. coli* DH10β in straight (125 μl/min flow rate) and bilateral (500 μl/min flow rate) microchannels, with 2.5 kV applied voltage and 5-ms square electroporation pulses with a 95% duty cycle as compared with a positive control in a 2-mm cuvette, which did not experience any flow.
Figure 30B:
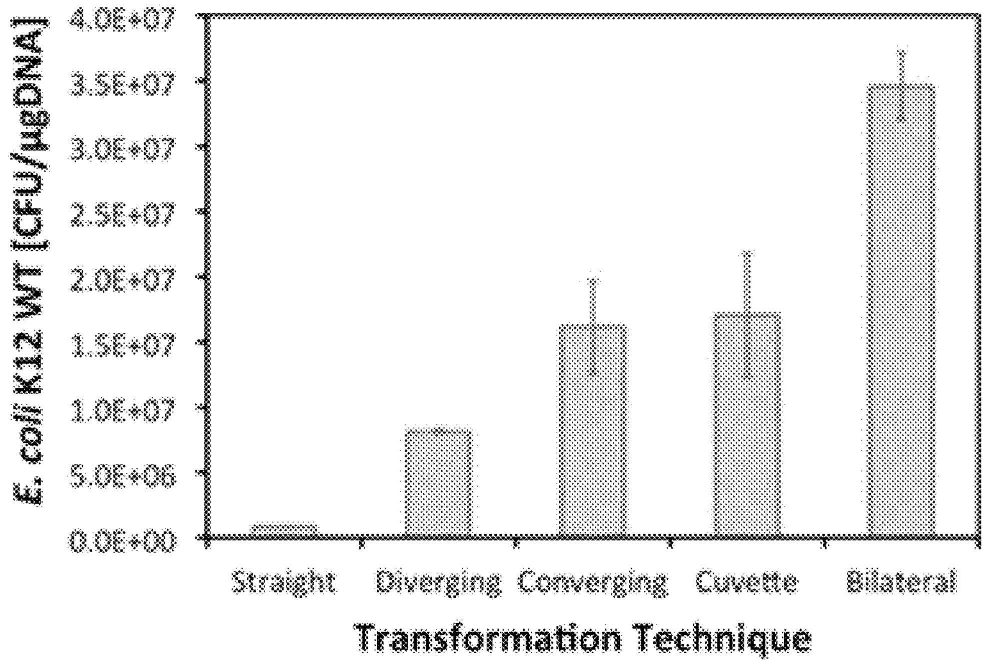
FIG. 30B is a graph illustrating transformation efficiency after flow-through electroporation of *E. coli* K12 wildtype in straight (125 μl/min flow rate) and bilateral (500 l/min flow rate) microchannels, with 2.5 kV applied voltage and 5-ms square electroporation pulses with a 95% duty cycle as compared with a positive control in a 2-mm cuvette, which did not experience any flow.

Example 9: Evaluation of Channel Geometry for Flow-Through Bacterial Transformation A single exponentially decaying electric pulse at 2.5 kV with a 5 ms time constant was applied to a 2-mm electroporation cuvette. This was used as a control to determine a base level of electrotransformation, as it is the current experimental standard. Microfluidic electroporation was performed with four different channel designs with electroporation cuvettes used as positive control (FIGS. 30A-30B). Experimentally, it was found that for *E. coli* DH10β and *E. coli* K12 wildtype, electrotransformation with the bilateral microfluidic device is superior to bulk electroporation in cuvettes (FIGS. 30A-30B). For *E. coli* K12 wildtype, the bilateral microfluidic device showed a statistically significant increase in transformation efficiency, with p-values of 0.007, <0.001, 0.010 and 0.002, compared respectively with cuvettes, straight, converging and diverging devices. For *E. coli* DH10β, the p-values were 0.070, 0.002, <0.001, and 0.283, when comparing bilateral devices with cuvettes, straight, converging and diverging devices. Even though bilateral devices did not lead to the highest transformation efficiency with DH10β, considering both *E. coli* K12 WT and DH10β data, bilateral devices showed the best and most consistent performance in terms of transformation efficiency. Therefore, in subsequent optimization with respect to flow rate and applied voltage (Examples 10 and 11), bilateral microfluidic devices were used. The experiments show that in straight microchannels, the least effective geometry tested, the electric field is insufficient to generate transformation efficiencies comparable to the cuvette experiments. These results are consistent with the simulated electric field distributions in which the straight microchannels are unable to amplify the electric fields to the levels achieved with the non-uniform geometries (Example 3).

Example 10: Effect of Volumetric Flow Rate on Bacterial Transformation

Figure 31A:
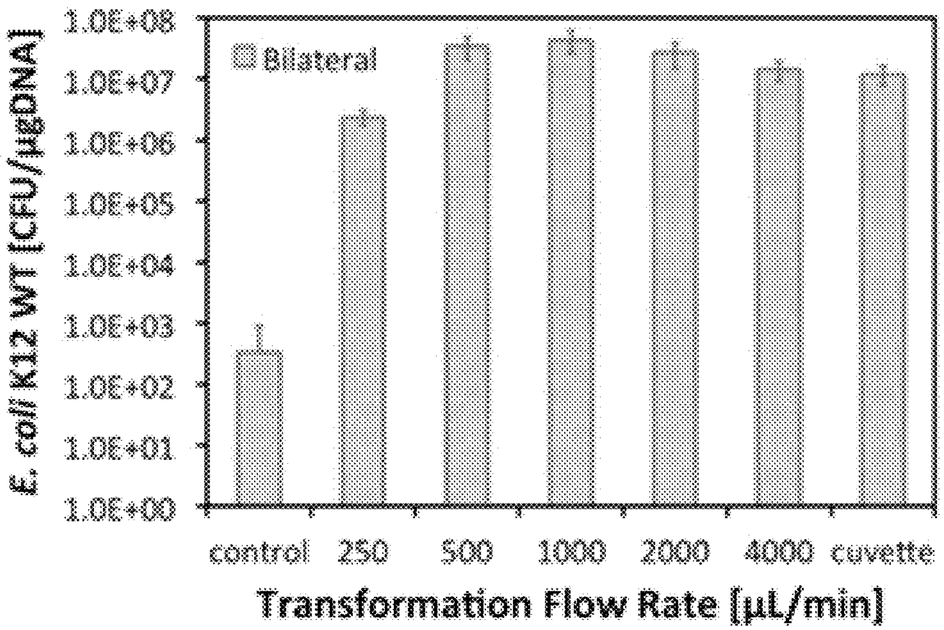
FIG. 31A is a graph illustrating transformation efficiency (in CFU/μgDNA) versus flow rate after flow-through electroporation of *E. coli* K12 wildtype in bilateral microchannels, with 2.5 kV applied, and 5-ms square electroporation pulses with a 95% duty cycle.
Figure 32A:
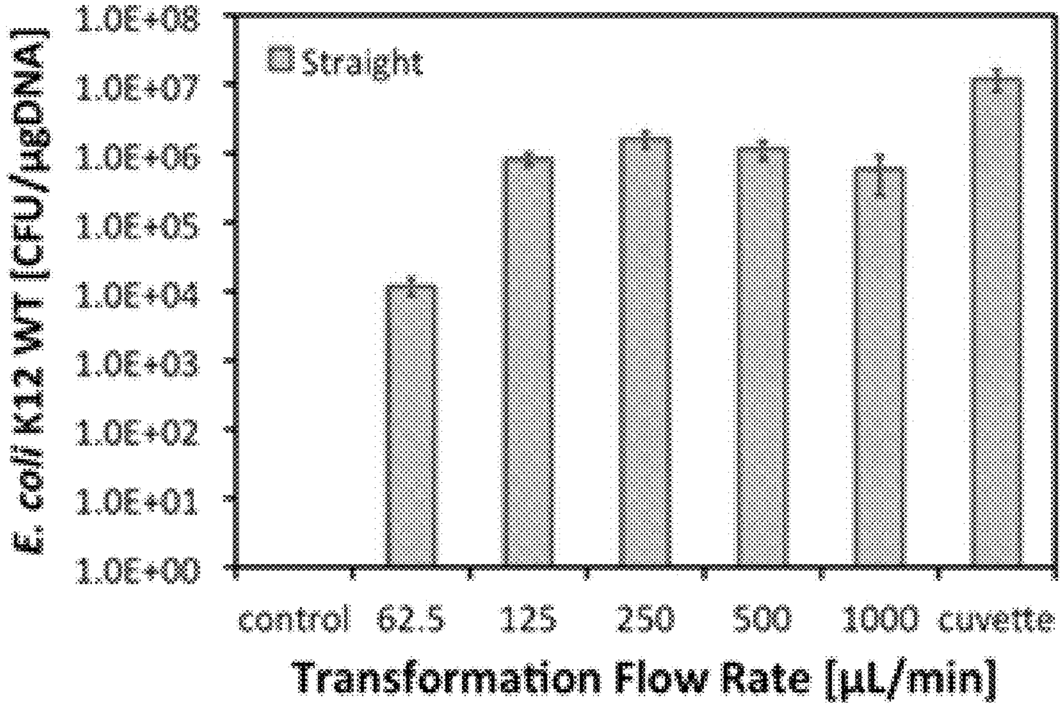
FIG. 32A is a graph illustrating transformation efficiency (in CFU/μgDNA) versus flow rate after flow-through electroporation of *E. coli* K12 wildtype in straight microchannels, with 2.5 kV applied, and 5-ms square electroporation pulses with a 95% duty cycle.

The volumetric flow rate influences the time dependent electric field experienced by cells in the microchannel geometries. This phenomenon was investigated in the bilateral (FIG. 31A) and straight (FIG. 32A) microchannels. Here, at fixed applied voltage of 2.5 kV, the volumetric flow rate was changed from 250-4000 μL/min in the bilateral microchannel (FIG. 31A) and from 62.5-1000 μL/min in the straight microchannel (FIG. 32A). When comparing 1000 μL/min with 250, 500, 2000, and 4000 μL/min in terms of transformation efficiency in the bilateral microchannel, t-test gives p-values of 0.016, 0.496, 0.241, and 0.052. Thus, on average, it is shown that a flow rate of 500-2000 μL/min leads to the highest transformation efficiency in the bilateral channel.

Consistent with the 4× difference in constriction volume, the optimal flow rate for the straight geometry was 250-500 μL/min using the same applied voltage of 2.5 kV (the p-values comparing flow of 250 μL/min with 62.5, 125, 500, 1000 μL/min are 0.003, 0.044, 0.236, 0.033). These results can be explained by the fact that lower flow rate leads to a longer residence time in the channel and thus prolonged exposure (FIG. 22) to high electric fields or deleterious thermal effects. Conversely, at some point higher flow rates limit the exposure time that the bacteria has at elevated electric fields, reducing the transformation efficiency. Of note, the highest average transformation efficiency in the straight microchannel at 250 μL/min (1.61×10^6 CFU/μgDNA) was lower than the cuvette electroporation (1.19×10^7 CFU/μgDNA) shown in FIGS. 31A and 32A due to the difference in maximum electric field that can be achieved with each technique.

Figure 31B:
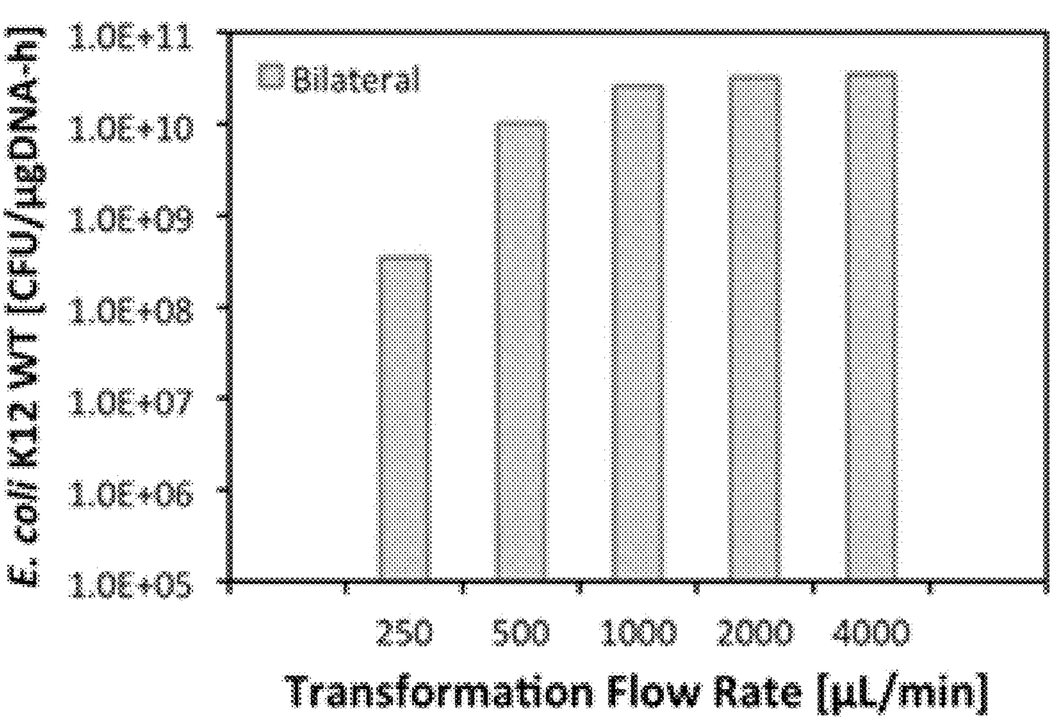
FIG. 31B is a graph illustrating transformation efficiency (in CFU/μgDNA/h) versus flow rate after flow-through electroporation of *E. coli* K12 wildtype in bilateral microchannels, with 2.5 kV applied, and 5-ms square electroporation pulses with a 95% duty cycle.
Figure 32B:
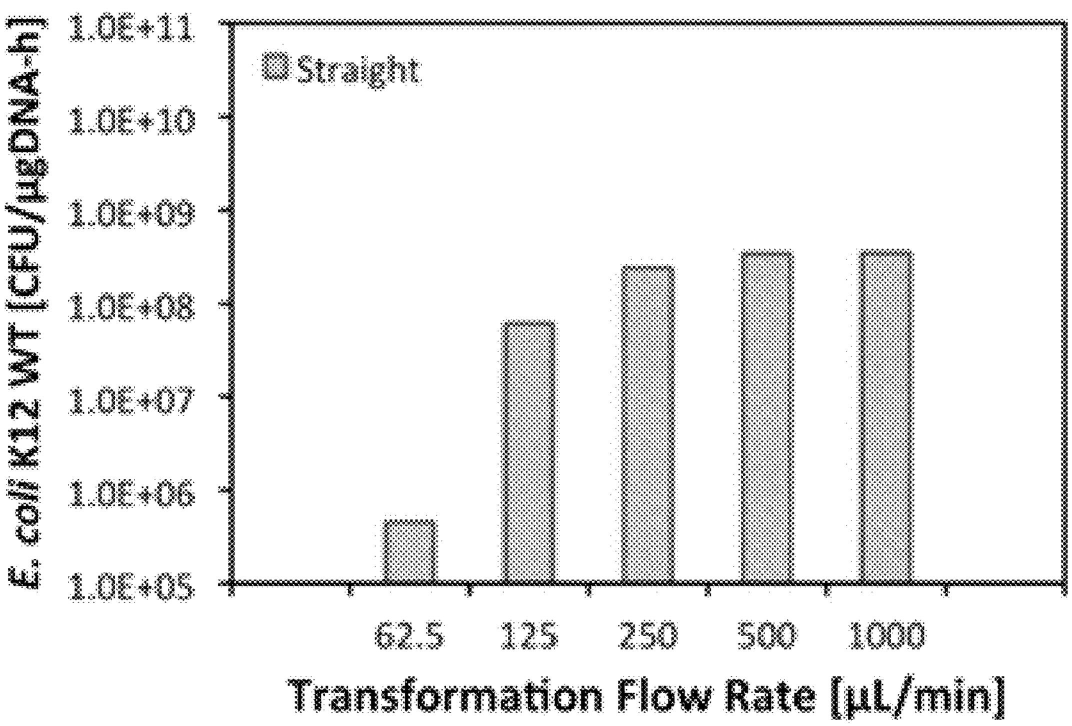
FIG. 32B is a graph illustrating transformation efficiency (in CFU/μgDNA/h) versus flow rate after flow-through electroporation of *E. coli* K12 wildtype in straight microchannels, with 2.5 kV applied, and 5-ms square electroporation pulses with a 95% duty cycle.

The ability to achieve comparable or higher transformation efficiencies in the tested microfluidic devices compared to cuvette electroporation was the initial purpose of this study. However, as the experimental parameter space was evaluated comprehensively, it was discovered that the main advantage of this technique is the potential to significantly increase throughput for certain applications. FIG. 31B demonstrates that using the bilateral channel can process up to two orders of magnitude more sample volume in a given period of time than using the batch-based cuvettes. This is relevant in applications where continuous transformation is desired, such as in the creation of a library of mutants for drug discovery or metabolic engineering. Although FIG. 32B shows an increase in the throughput with increasing flow rate in the straight geometry, increasing the electric field is required to achieve comparable CFU/μgDNA/h to those achieved in the bilateral channel. The transformation efficiency in straight channels could be improved by increasing the applied voltage and/or reducing the channel width.

Figure 33:
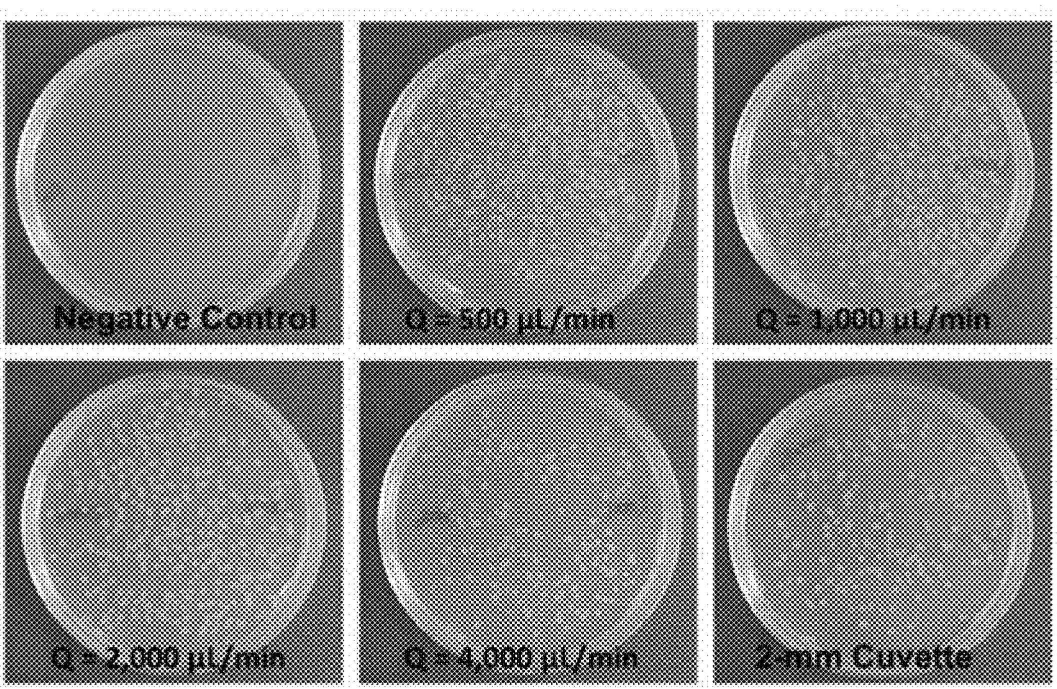
FIG. 33 is a photograph of Colony Forming Units (CFU) used to quantify transformation efficiencies after flow-through electroporation of *E. coli* K12 wildtype in bilateral microchannels. The experimental parameters involved an applied voltage of 2.5 kV, 5-ms square pulses with a 95% duty cycle, and flow rates of 500 μL/min, 1,000 μL/min, 2,000 μL/min, and 4,000 μL/min, which were compared to negative control and cuvette electroporation.

FIG. 33 displays the colony forming units (CFU) from electroporated *E. coli* K12 wildtype at an applied voltage of 2.5 kV and with 5-ms square pulses at a 95% duty cycle in the bilateral microchannel. The panels demonstrate the lack of transformed bacteria in the negative control, as well as the baseline transformation in the positive control with 2 mm cuvettes. The panels further demonstrate the improved transformation efficiencies with flow rates between 500-2000 μL/min. These cells were plated in ampicillin containing LB and agar, which was used as a selection method to isolate the successfully transformed bacterial cells.

Example 11: Effect of Applied Voltage on Flow-Through Electrotransformation

Figure 34:
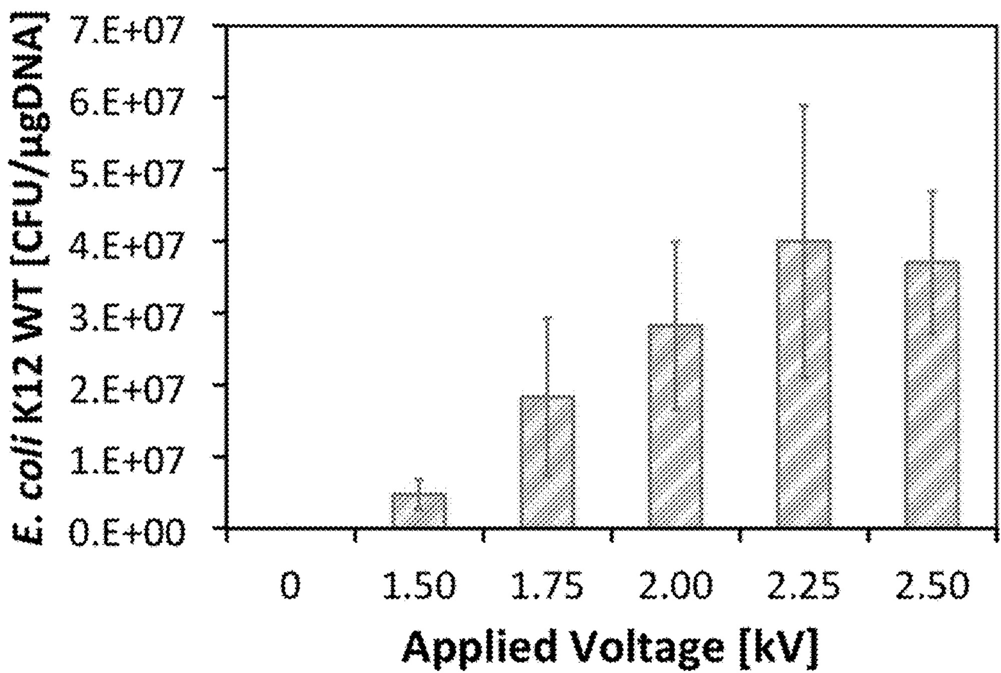
FIG. 34 is a graph illustrating transformation efficiency versus applied voltage (1.50, 1.75, 2.00, 2.25, and 2.50 kV with 5-ms square electroporation pulses at a 95% duty cycle) for flow-through electroporation of *E. coli* K12 wildtype in bilateral microchannels.

The influence of applied voltage on the transformation efficiency was tested at a fixed volumetric flow rate of 500 μL/min in the bilaterally converging microchannel. The applied voltages were 1.50, 1.75, 2.00, 2.25, and 2.50 kV (FIG. 34). In terms of transformation efficiency, comparing conditions of 2.25 kV with 1.50, 1.75, 2.00 and 2.50 kV, p-values of, respectively, 0.033, 0.158, 0.407, and 0.820 were obtained using t-test. The simulation showed that the peak electric field strength within the microchannel is ~15 kV/cm when 2.5 kV is applied (FIG. 23). The increased transformation efficiency as shown in FIG. 34 can be attributed to the increased electric field strength in the microchannel, which is still below the threshold for killing bacterial cells due to the short exposure time. The transformation efficiency achieved in the bilateral microfluidic device at 1.5 kV was comparable to the transformation efficiency achieved in the straight microchannel at 2.5 kV, demonstrating an additional advantage of the bilateral design.

Example 12: High-Throughput Transformation of LOBSTR *E. coli*

Figure 35:
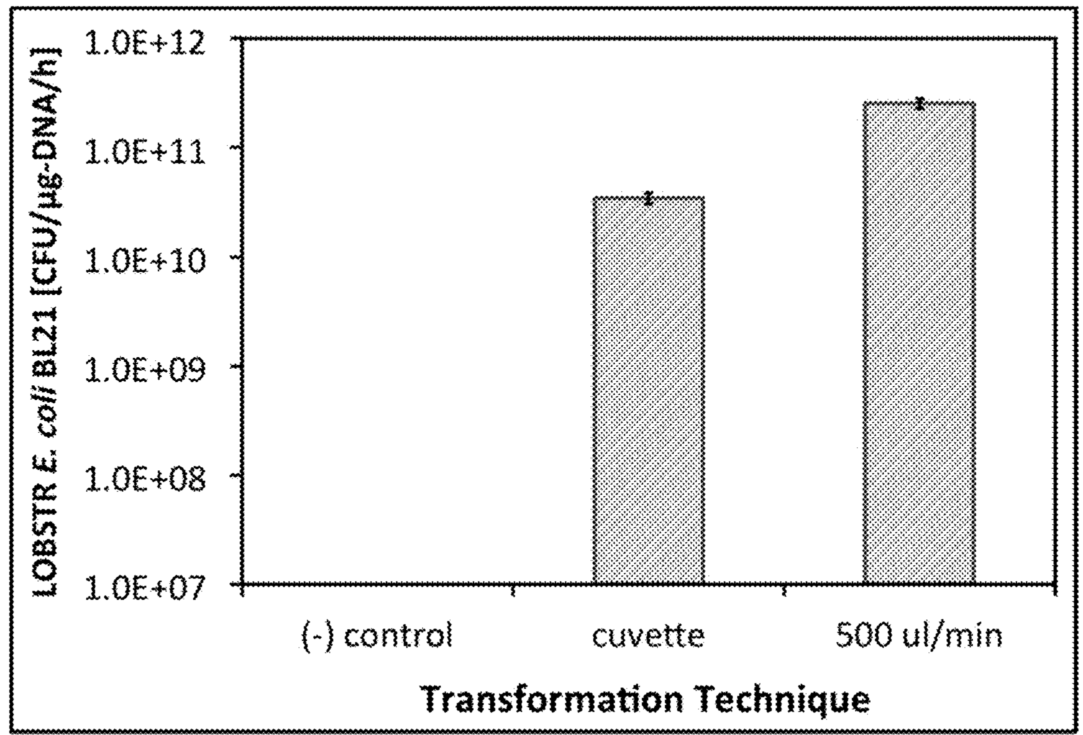
FIG. 35 is a graph illustrating transformation efficiency (in CFU/μgDNA/h) of flow-through electroporation of LOBSTR *E. coli* BL21 as compared with cuvette-based transformation.

In order to evaluate if high throughput platforms containing bilaterally converging microchannels, as shown in FIG. 23A, were able to achieve transformation efficiencies comparable to values in the literature (e.g., New England Biolabs, Ipswich, MA—www.neb.com), additional experiments were performed with cell solutions containing cell concentrations of about ~1.5×10^9 cells/mL. Specifically, LOBSTR *Escherichia coli* BL21 in exponential phase (MIT, Schwartz Lab) was used to demonstrate the high-throughput and high efficiency transformation. Electric pulses were delivered in the presence of ampicillin resistance and green fluorescent protein (GFP) encoding DNA plasmids (Parts Registry K176011) at a final concentration of 1.0 ng/μL in 10% (v/v) glycerol supplemented with 0.05% (v/v) Tween 20. The experimental samples (100 μL) were driven at 500 μL/min and resulted in bacterial residence times within the constriction of <5 ms. Results show that transformation efficiency can be increased by an order of magnitude or more, while throughput increases by one to two orders of magnitude as compared to electroporation cuvettes (FIG. 35). The cuvette transformation resulted in 3.47×10^10 CFU/μg-DNA/h while the microfluidic high throughput electroporation resulted in 2.53×10^11 CFU/μg-DNA/h. The throughput increase is calculated by assuming the continuous flow system processes 100 μL samples, resulting in 300 samples per hour. This is compared to traditional cuvettes, which can be processed by a single technician at a rate of roughly 20 samples per hour. Note that the continuous flow system can perform at even higher throughput if operated using eight or more parallel channels or smaller sample volumes such as 25-50 μL.

Example 13: High-Throughput Transformation of *E. coli* DH5α

Figure 36:
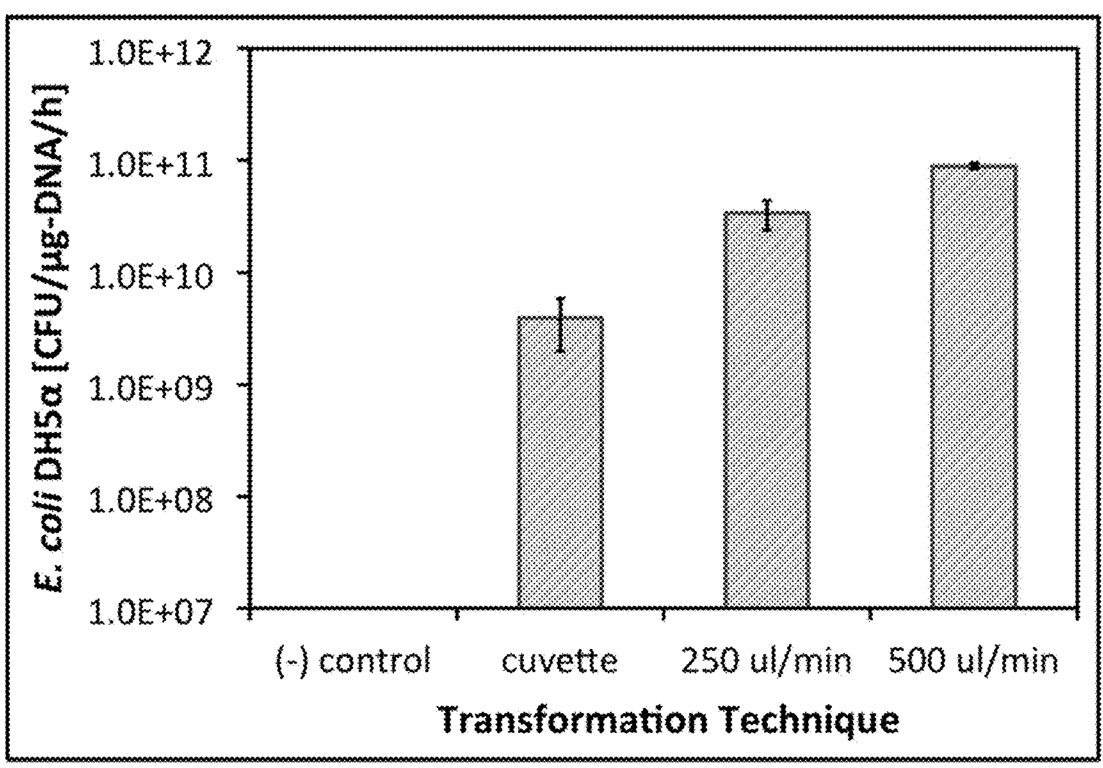
FIG. 36 is a graph illustrating transformation efficiency (in CFU/μgDNA/h) of flow-through electroporation of *E. coli* DH5α as compared with cuvette-based transformation.

In order to further evaluate high throughput platforms containing bilaterally converging microchannels, *Escherichia coli* DH5α in exponential phase (MIT, Boyer Lab) was used to demonstrate high-throughput transformation. Pulsed electric fields (2.5 kV and 5-ms square pulses with a 20% duty cycle) were delivered in the presence of DNA-coding for ampicillin resistance and GFP (Parts Registry K176011) at a final DNA concentration of C=1 ng/μL. The electroporation buffer consisted of 10% (v/v) glycerol supplemented with 0.05% (v/v) Tween 20 in order to mitigate cell-to-cell agglomeration. Each experimental sample (100 μL) was driven at 0 μL/min (3.93×10^9 CFU/μg-DNA/h in 2-mm cuvette), 250 μL/min (23.39×10^10 CFU/μg-DNA/h), or 500 μL/min (8.92×10^10 CFU/μg-DNA/h) and resulted in a residence time (pulse duration) within the constriction<5 ms. High transformation efficiencies (FIG. 36) were obtained with a throughput increase of several orders of magnitude as compared to the state-of-the-art cuvette electroporation. Overall, this work facilitates high throughput transformation of microorganisms, accelerating development of genetically engineered microbes for industrial, medical, and scientific applications.

Example 14: High-Throughput Transformation of *Parabodo caudatus*

*Parabodo caudatus* (ATCC 50361) was used in this study. Initially, *Parabodo caudatus* was grown in 50% ATCC seawater 802 media. Subsequently, seawater was replaced with distilled water in order to reduce the high electrical conductivity during the electroporation. Briefly, this is a cerophyl-based media enriched with 3.5 mM sodium phosphate dibasic (Na2HPO4) and with *Klebsiella pneumoniae* added as a food source. Cultures were incubated at 22° C. and sub-cultured weekly in fresh T-25 vented tissue culture flasks (Falcon brand, Fisher Scientific) containing 30 ml of fresh media.

Three plasmids for transfection were obtained from Addgene. In particular, pEYFP-Mitotrap (Addgene plasmid #46942), pEF-GFP (Addgene plasmid #11154), and pUB-GFP (Addgene plasmid #11155) were provided. Transfections with the pEF-GFP plasmid with the EF1 alpha promoter from mammalian cells for expression of GFP and the pUB-GFP plasmid with the mammalian Ubiquitin C promoter for expression of GFP were investigated in this study. A third plasmid, the pEYFP-Mitotrap, with the CMV mammalian and yeast promoter, was also investigated, with the Tom70p gene targeting the outer membrane of the mitochondria in yeast and mammalian cells. Plasmids were purified from 100 mL cultures grown overnight in standard Luria Bertani liquid medium with appropriate selection marker. Purification was done according to the manufacturer's protocol for the Plasmid Midi Kit (Qiagen, Germantown, MD).

*Parabodo caudatus* cells were grown to logarithmic phase (~1×10^7 cells/ml) and harvested by centrifugation at 5000×g for 30 s, re-suspended in 200 μl cytomix (50% in distilled water), mixed with 20 to 40 μg of plasmid, and then transferred into an electroporation cuvette (2.0-mm gap) for electroporation with an exponential decay system, Micro-Pulser™ Bio-Rad (CN 165-2100). For the microfluidic system, cells in cytomix buffer were aspirated into 1/16 inch Tygon® tubing (McMaster-Carr) prior to being delivered into the microchannel of a prototype device.

Figure 37:
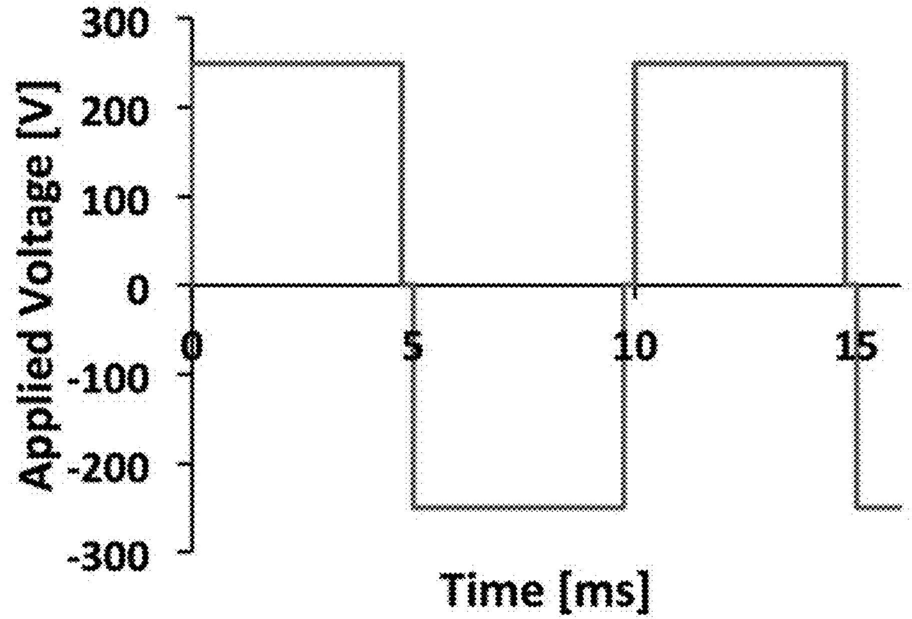
FIG. 37 is a graph illustrating a representative 5 ms square waveform delivered with alternating polarity in a microfluidic device at a 95% duty cycle.
Figure 38:
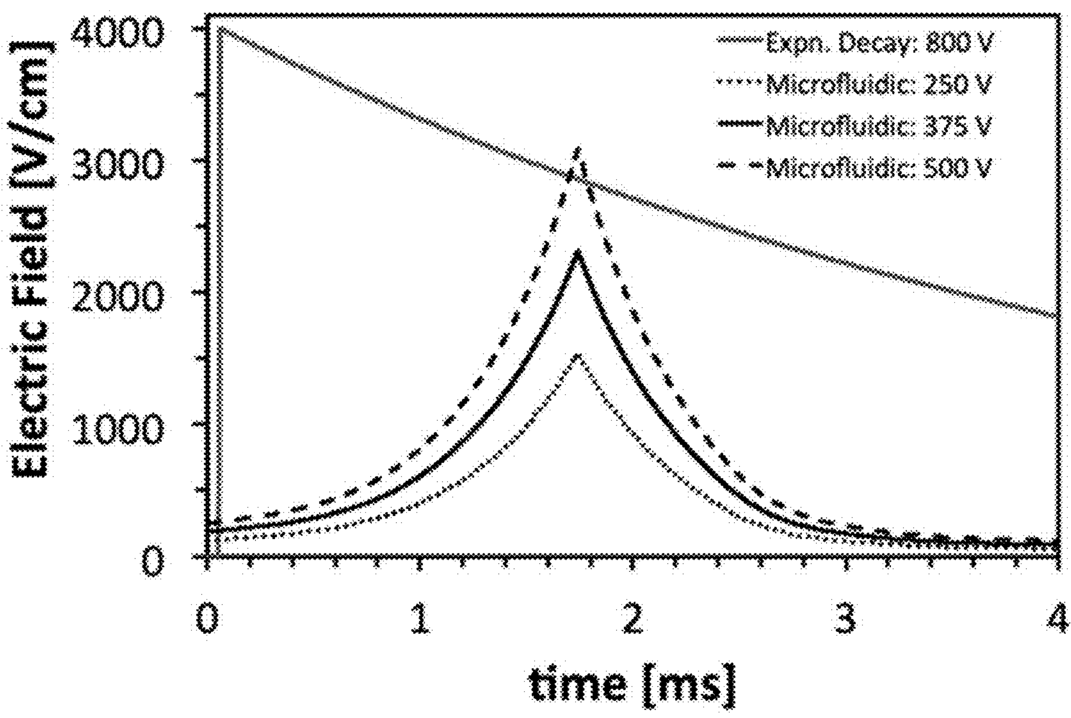
FIG. 38 is a graph illustrating electric field waveforms employed for transient and stable transfection of *Parabodo caudatus.*

Electroporation devices having microfluidic channels containing a bilateral constriction between inlet and outlet electrode connections (length=3.0 mm, $width_{min}$=50 μm, $width_{max}$=2.0 mm, and height=100 μm) were used. During *Parabodo caudatus* transfection, the cells were driven through the microfluidic device at flow rates of 50 μL/min and 500 μL/min, which correspond to residence times of 20 ms and 2 ms, respectively, through a dispensing needle. Square wave pulses with 5 ms ON and 5 ms OFF cycles (50% duty cycle) were applied. The pulses were delivered from electrodes with alternating polarity between the pulses to reduce electrolytic effects at the electrode-buffer interface. FIG. 37 is a graph illustrating pulse distribution as applied to the samples. The bilateral constriction geometry results in a ~6× amplification of the applied voltage in the narrowest portion of the constriction. Therefore, the applied voltage of 250 V presented in FIG. 37 resulted in a maximum electric field ($E_{max}$) of 1,500 V/cm in the microfluidic device, as shown in FIG. 38, which illustrates the electric field waveforms that were employed for transient and stable transfection of *Parabodo caudatus*.

After flowing through the microchannel, each 200 μL cell sample was added to a 1.5 ml Eppendorf® tube containing 1 ml of fresh growth media for cell recovery. The applied voltages had amplitudes of 250 V ($E_{max}$=1,500 V/cm), 375 V ($E_{max}$=2,250 V/cm), and 500 V ($E_{max}$=3,000 V/cm) for each polarity. The non-uniform constriction in the microfluidic devices generates a variable electric field that is capable of transfecting cells while minimizing exposure to the highest electric field.

Circular DNA plasmids pEF-GFP, pUB-GFP, and pEYFP-Mitotrap were introduced separately into *P. caudatus* using parameters presented in Table 2. All of the plasmids were expressed in the cytoplasm of *P. caudatus* cells, after they were transcribed in the host's nucleus. In all cases of successful transfection, transformants were viable and their growth rate was similar to that of wild-type cells. No morphological differences in the cell shape were detected between the transformed and wild type cells. Expression of the GFP gene, driven by either the EF1 alpha promoter or the ubiquitin C promoter, and the YFP gene, driven by the CMV promoter, was documented using a fluorescence microscope 12 hours post-electroporation. Expressed GFP signal levels decreased gradually over the 48 hours post-electroporation, but YFP expression was maintained for 5 days (the longest time that expression was monitored).

TABLE 2

Transformation Parameters

| System | Voltage (V) | $E_{max}$ (V/cm) | Pulse Length (ms) | Buffer | Plasmid | Duty Cycle % | Transfection Efficiency %* |
|---|---|---|---|---|---|---|---|
| Microfluidic | 313 | 1,000 | 20 | cytomix | pEF-GFP | 95 | 20-30 |
| Electroporation | 250 | 1,500 | 2 | $H_2O$ | Mitrotrap | 95 | 30-40 |
| | 375 | 2,250 | 2 | $H_2O$ | Mitrotrap | 95 | 40-50 |
| | 375 | 2,250 | 2 | $H_2O$ | pUB-GFP* | 50 | 20-30 |
| | 375 | 2,250 | 4 | $H_2O$ | pUB-GFP* | 50 | 20-30 |
| Exponential | 800 | 4,000 | 2 or 3 | $H_20$ | pEF-GFP | n/a | 5-10 |
| Decay | 800 | 4,000 | 2 or 3 | $H_20$ | Mitrotrap | n/a | 5-10 |

The initial successful transfections experiments used a 50% duty cycle with maximum electric fields of 750 V/cm, 1,500 V/cm, or 2,250 V/cm. These experiments conducted with a 50% duty cycle resulted in transfection efficiencies ranging between 20-30%. The duty cycle was then increased to 95% to increase the fraction of treated cells with maximum electric fields ranging between 500 V/cm and 3,000 V/cm. Transfection efficiencies ranging between 30-50% were also achieved with maximum electric fields of 1,500 V/cm and 2,250 V/cm using 5 ms pulses in MilliQ® water. Additionally, transfection efficiencies ranging between 20-30% using a maximum electric field of 1,000 V/cm with 20 ms pulses in 50% cytomix buffer in a straight channel were also achieved. The microfluidic platform was the most efficient method with 30-50% of the cells successfully transformed (Table 2). The exponential decay electroporation resulted in ≤5% transformation efficiency making it the least optimal transfection platform evaluated (Table 2).

The microfluidic electroporation system resulted in the highest transfection efficiencies ranging from 20% to 50%. Successful *P. caudatus* transfection was demonstrated employing electric fields of 1,500 V/cm, resulting in transformation efficiencies of 30-40%, and 2,250 V/cm, resulting in transformation efficiencies of 40-50% efficiency using 5 ms pulse durations in MilliQ® water and the bilaterally constricting channel geometry. Additionally, by decreasing the electric field to 1,000 V/cm and by employing longer 20 ms pulses, 20-30% transfection efficiencies in 50% cytomix buffer using the straight channel constriction were achieved. These results demonstrate that different geometric constrictions can be used successfully to modulate the electric field that the cell is exposed to for successful transfection.

Example 15: High-Throughput Transformation of *Plasmodium falciparum*

*Plasmodium falciparum* was used in this study. Very minimal sample preparation was performed. *Plasmodium falciparum* resided within a cell suspension containing red blood cells and having salt concentrations similar to blood.

Figure 39:
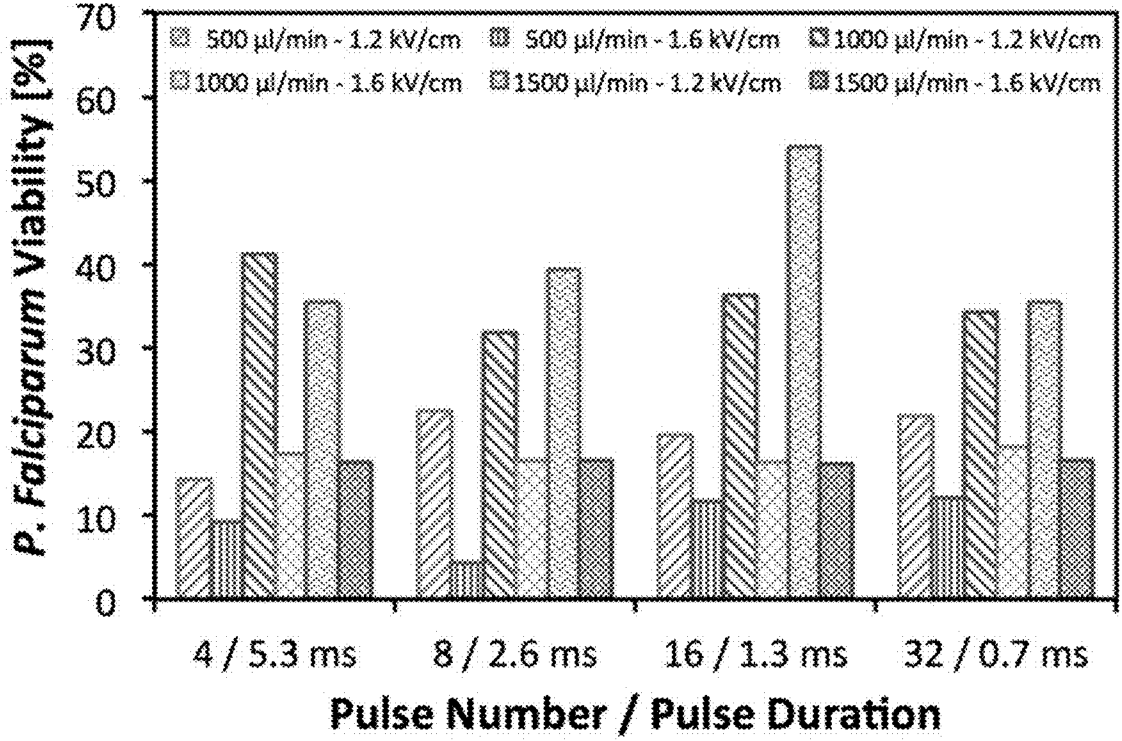
FIG. 39 is a graph illustrating viability of *Plasmodium falciparum* after flow-through electroporation in a straight channel geometry with electric fields of 1.2 kV/cm or 1.6 kV/cm, and pulses delivered with a 95% duty cycle and having durations of 5.3 ms, 2.6 ms, 1.3 ms, or 0.7 ms for each polarity. The red blood cells infected with *P. falciparum* were driven at 500 μL/min, 1,000 μL/min, or 1,500 μL/min flow rates.

The experimental results demonstrate that there is an inverse relationship between increasing electric field and cell viability at 24 hours post-microfluidic electroporation. Specifically, the use of straight constriction geometries resulted in cell viabilities ranging from approximately 5-50% when driven at 500 μL/min, 1,000 μL/min, or 1,500 μL/min flow rates with electric fields of 1.2 kV/cm or 1.6 kV/cm, as shown in FIG. 39. Similarly, in the diverging geometry (FIG. 40), the cell viability post-microfluidic electroporation was inversely proportional to the electric field with the highest viability at the 2.4 kV/cm and the lowest viability at 3.3 kV/cm. Specifically, the cell viability ranged between approximately 2.5% and 25% when driven through the diverging geometry at 1,000 μL/min or 1,250 μL/min. In summary, higher electric field exposure results in reduced cell viability. Additionally, driving cells at slower flow rates resulted in a longer residence time within the constriction channel that, in turn, generated lower cell viability.

Figure 40:
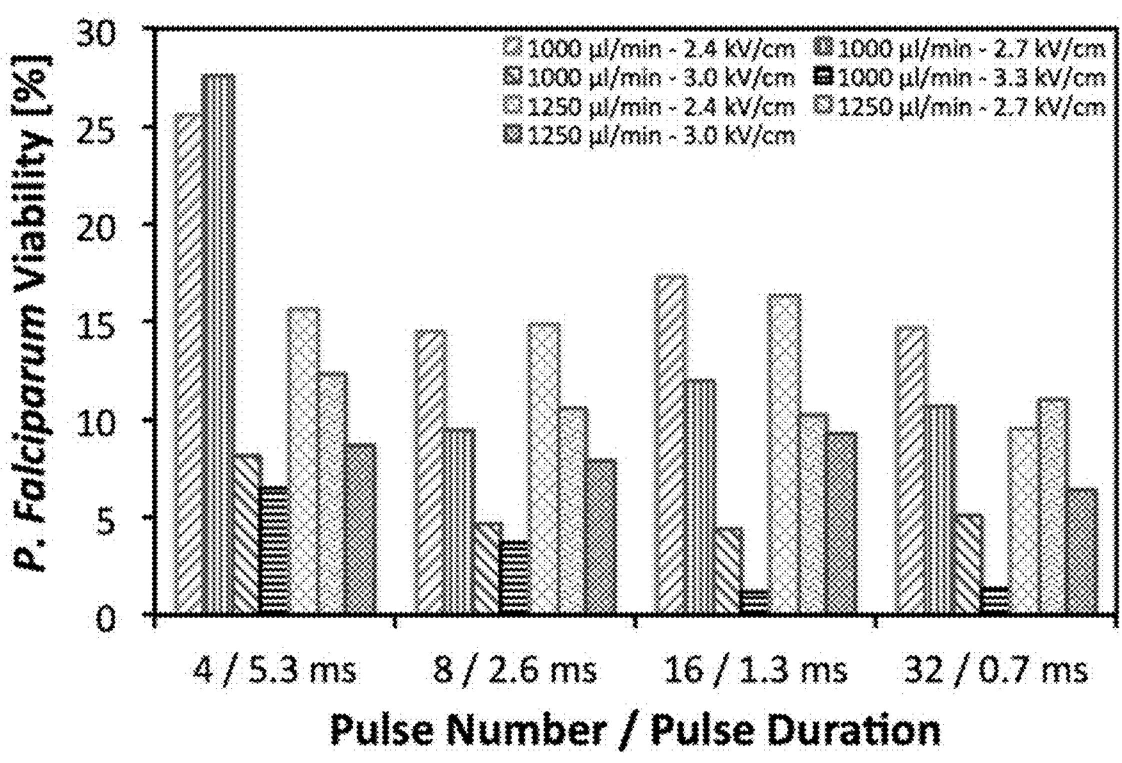
FIG. 40 is a graph illustrating viability of *Plasmodium falciparum* after flow-through electroporation in a diverging channel geometry with maximum electric fields of 2.4 kV/cm, 2.7 kV/cm, 3.0 kV/cm, or 3.3 kV/cm, and pulses delivered with a 95% duty cycle and having durations of 5.3 ms, 2.6 ms, 1.3 ms, or 0.7 ms for each polarity. The red blood cells infected with *P. falciparum* were driven at 1,000 μL/min or 1,250 μL/min flow rates.
Figure 41:
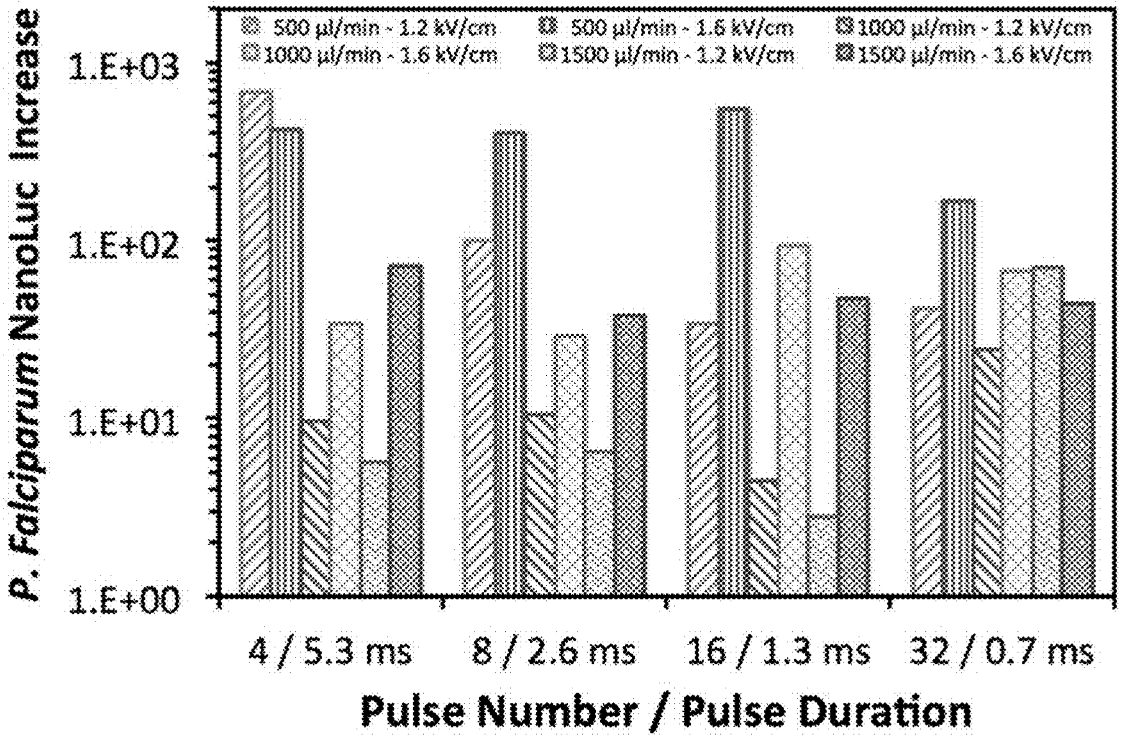
FIG. 41 is a graph illustrating *Plasmodium falciparum* increase in NanoLuc® Luciferase (Promega, Madison, Wisconsin) expression after flow-through transfection in a straight channel geometry with electric fields of 1.2 kV/cm or 1.6 kV/cm. The pulses were delivered with a 95% duty cycle and had durations of 5.3 ms, 2.6 ms, 1.3 ms, or 0.7 ms for each polarity. The red blood cells infected with *P. falciparum* were driven at 500 μL/min, 1,000 μL/min, or 1,500 μL/min flow rates.
Figure 42:
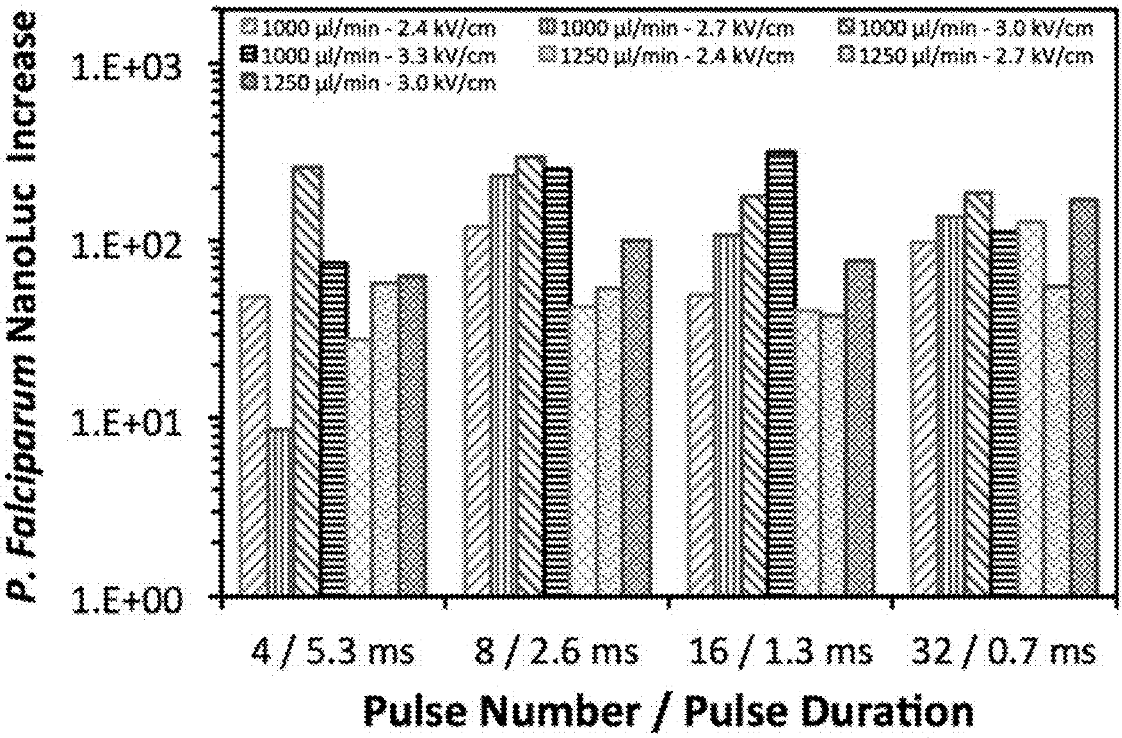
FIG. 42 is a graph illustrating *Plasmodium falciparum* viability after flow-through transfection in a diverging channel geometry with maximum electric fields of 2.4 kV/cm, 2.7 kV/cm, 3.0 kV/cm, or 3.3 kV/cm. The pulses were delivered with a 95% duty cycle and had durations of 5.3 ms, 2.6 ms, 1.3 ms, or 0.7 ms for each polarity. The red blood cells infected with *P. falciparum* were driven at 1,000 μL/min or 1,250 μL/min flow rates.

Contrary to the cell viability data presented in FIGS. 39 and 40, the slowest flow rates and higher electric fields resulted in quantifiable transient transfection of *P. falciparum* using the microfluidic transfection platform. FIG. 41 demonstrates up to a 700-fold increase in fluorescence expression post-transfection compared to the non-electroporated control samples when driven at 500 μL/min and exposed to a 1.2 kV/cm electric field in the straight channel geometry. Similarly, there was a 300-fold increase in baseline fluorescence when electroporated in the diverging channel geometry at maximum electric fields of 3.0 kV/cm-3.3 kV/cm and driven at 1,000 μL/min (FIG. 42). These results demonstrate the capabilities of the microfluidic platform to transiently transfect protozoan parasites that live within red blood cells in order to survive. All the experiments were performed in high conductivity buffer in order to maintain the viability of the red blood cells and the viability of the parasites as high as possible.

In conclusion, the flow-through transfection platform is capable of successfully delivering genetic material across the four layers (e.g., red blood cell membrane, vacuole, parasite membrane, parasite nuclear membrane) that separate the outside of the red blood cell from the *P. falciparum* nuclear membrane. The pulses were delivered at flow rates ranging from 500 μL/min to 1,500 μL/min and electric fields ranging from 1.2 kV/cm to 3.3 kV/cm in highly conductive buffer that simulated human blood. The increase in fluorescence confirms the success of the transient transfection 96 hours after electric field exposure within the straight or diverging channel constriction.

Example 16. Buffer Conductivity Characterization

Electroporation uses pulsed electric fields to transiently disrupt the cell's membrane and deliver exogenous material into the cell. However, due to the current that flows through the sample during electroporation, the temperature also increases due to resistive heating. The temperature increase during the pulse depends on the electrical conductivity of the electroporation buffer and the squared magnitude of the electric field. Therefore, the electroporation buffer must be chosen carefully in order to maximize transformation efficiency and maintain high cell viability. Here, the effect of electroporation buffer on the transformation efficiency of *E. coli* DH10β with DNA encoding for green fluorescent protein (GFP) expression and ampicillin resistance as the selection antibiotic was evaluated. Specifically, each 100 μL sample tested contained 10 ng of DNA and cells were at an $OD_{600}$=0.5 (1:20 dilution) after 3× washes in 10% glycerol to remove the majority of ions from the original LB growth media. The buffer concentration was modulated by adding 10 μL of PBS to 90 μL of cell+DNA solution for final concentrations ranging from 10% glycerol only to 1×10^−2 M PBS concentration. Experimental conditions were completed in triplicate and involved driving the cell+DNA samples through a diverging channel at 2.0 mL/min and using 2.5 kV voltages at a 95% duty cycle (period of 5.25 ms). The positive controls were completed in cuvettes containing cell+DNA solution without any PBS and with an exponential decay pulse of 2.5 kV with time constant of 5.7 ms.

Figure 43:
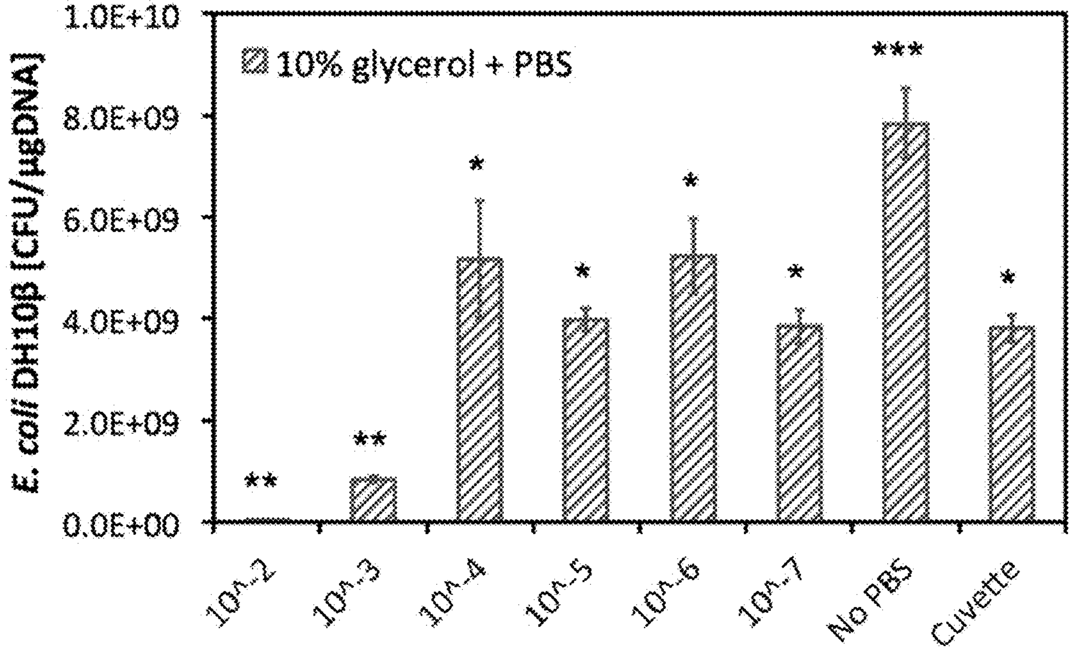
FIG. 43 is a graph illustrating transformation efficiency characterization in a microfluidic device with a diverging constriction geometry. The *E. coli* DH10β was driven at 2 mL/min and exposed to applied voltages of 2.5 kV in each polarity at a 95% duty cycle (Period 5.25 ms).

The results are shown in FIG. 43. Three statistically significant responses were detected upon data analysis. High buffer concentrations of 1×10^−2 M or 1×10^−3 M achieved the lowest transformation efficiency at 1.00×10^7 CFU/μgDNA and 8.43×10^8 CFU/μgDNA due to the highest rate of cell death that can be attributed to deleterious heating. An intermediate range of 3.81×10^9 CFU/μgDNA-5.22×10^9 CFU/μgDNA that involved buffer concentrations between 1×10^−4 M-1×10^−7 M PBS in the diverging channel or no PBS in the cuvette. The highest transformation efficiency was achieved without any PBS in the diverging channel with 7.83×10^9 CFU/μgDNA. There results confirm that in order to achieve the maximum transformation efficiency, researchers should carefully evaluate the electrical conductivity of their samples in order to minimize deleterious effects due to excessive Joule heating and maximize cell viability.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of transfecting cells, the method comprising:

flowing a mammalian cell suspension through a flow path defined within a fluid transport structure, the flowing comprising causing a flow of a plurality of cells of the mammalian cell suspension through an axial cross-section of the flow path concurrently, wherein the flow path comprises a minimum diameter of 50 μm, wherein the fluid transport structure comprises conductive elements configured to produce an electric field in the flow path, wherein the conductive elements are hollow cylindrical electrodes arranged axially at either end of the flow path; and applying a voltage to generate the electric field in the flow path, wherein the electric field is sufficient to transfect the plurality of cells flowing through the axial cross-section of the flow path.

2. The method of claim 1, wherein the flowing of the cell suspension through the flow path is continuous.

3. The method of claim 1, further comprising applying a voltage of about 0.1 kV to about 0.5 kV to the flow path that results in a maximum electric field of about 0.5 kV/cm to about 2.5 kV/cm as a function of the amplification.

4. The method of claim 1, wherein a residence time of the cell suspension flowing through the flow path is about 0.1 ms to about 100 ms, about 0.5 ms to about 50 ms, about 2.5 ms to about 75 ms, about 5 ms to about to about 50 ms, or about 7 ms to about 25 ms.

5. The method of claim 1, wherein the cell suspension comprises an electrical conductivity buffer having an ion concentration of about 1×10ˆ−9 M to about 1×10ˆ−4M.

6. The method of claim 1, wherein at least the subset of cells are transfected with a payload, wherein the payload is a nucleic acid or a protein.

7. The method of claim 1, wherein the minimum diameter of the flow path is 100 μm.

8. The method of claim 1, wherein inner diameters of the hollow cylindrical electrodes are greater than an inner diameter of the flow path.

9. The method of claim 1, wherein applying the voltage to generate the electric field comprises generating a uniform electric field in the flow path.

10. A method of performing cell transfection, the method comprising:

flowing one or more mammalian cell suspension(s) through a plurality of flow paths, each flow path defined within a fluid transport structure, the flowing comprising causing, for a given flow path of the plurality of flow paths, a flow of a plurality of cells of the mammalian cell suspension through an axial cross-section of the given flow path concurrently, wherein the flow paths each comprise a minimum diameter of 50 μm, wherein the fluid transport structure comprises conductive elements configured to produce an electric field in the flow path, wherein the conductive elements are hollow cylindrical electrodes arranged axially at either end of the flow path; and applying a voltage to generate the electric field in the flow paths;

wherein the electric field is sufficient to transfect the plurality of cells flowing through the corresponding axial cross-sections of the flow paths.

* * * * *